US007671252B2

(12) United States Patent
Qiu et al.

(10) Patent No.: US 7,671,252 B2
(45) Date of Patent: Mar. 2, 2010

(54) FAD4, FAD5, FAD5-2, AND FAD6, NOVEL FATTY ACID DESATURASE FAMILY MEMBERS AND USES THEREOF

(75) Inventors: Xiao Qiu, Saskatoon (CA); Haiping Hong, Morrisville, NC (US)

(73) Assignee: Bioriginal Food & Science Corp., Saskatoon (CA)

( * ) Notice: Subject to any disclaimer, the term of this patent is extended or adjusted under 35 U.S.C. 154(b) by 407 days.

(21) Appl. No.: 11/342,731

(22) Filed: Jan. 30, 2006

(65) Prior Publication Data
US 2006/0117414 A1 Jun. 1, 2006

Related U.S. Application Data

(62) Division of application No. 09/967,477, filed on Sep. 28, 2001, now Pat. No. 7,087,432.

(60) Provisional application No. 60/236,303, filed on Sep. 28, 2000, provisional application No. 60/297,562, filed on Jun. 12, 2001.

(51) Int. Cl.
C12N 15/82 (2006.01)
A01H 5/00 (2006.01)
(52) U.S. Cl. .................. 800/281; 800/298; 435/419
(58) Field of Classification Search ................ None
See application file for complete search history.

(56) References Cited

U.S. PATENT DOCUMENTS

| 5,246,842 | A | 9/1993 | O'Brien et al. |
| 5,614,393 | A | 3/1997 | Thomas et al. |
| 5,968,809 | A | 10/1999 | Knutzon et al. |
| 5,972,664 | A | 10/1999 | Knutzon et al. |
| 6,051,754 | A | 4/2000 | Knutzon |
| 6,897,050 | B1 | 5/2005 | Napier |

FOREIGN PATENT DOCUMENTS

| CA | 2363064 A1 | 4/2002 |
| WO | WO-93/06712 A1 | 4/1993 |
| WO | WO-96/21022 A2 | 7/1996 |
| WO | WO-98/03671 A1 | 1/1998 |
| WO | WO-98/46763 A1 | 10/1998 |
| WO | WO-98/46764 A1 | 10/1998 |
| WO | WO-98/46765 A1 | 10/1998 |
| WO | WO-99/27111 A1 | 6/1999 |
| WO | WO-99/33958 A2 | 7/1999 |
| WO | WO-99/64614 A2 | 12/1999 |
| WO | WO-00/12720 A2 | 3/2000 |
| WO | WO-00/20602 A2 | 4/2000 |
| WO | WO-00/20603 A1 | 4/2000 |
| WO | WO-00/21524 A1 | 4/2000 |
| WO | WO-00/21557 A1 | 4/2000 |
| WO | WO-00/34439 A1 | 6/2000 |
| WO | WO-00/40705 A2 | 7/2000 |
| WO | WO-00/51444 A1 | 9/2000 |
| WO | WO-00/75341 A1 | 12/2000 |
| WO | WO-02/081668 A2 | 10/2002 |
| WO | WO-03/012092 A1 | 2/2003 |
| WO | WO-03/078639 A2 | 9/2003 |
| WO | WO-2004/090123 A2 | 10/2004 |

OTHER PUBLICATIONS

Brenner, S.E., TIG 15(4): 132-133, Apr. 1999.*
Bork et al, TIG 12(10): 425-427, Oct. 1996.*
Broun et al, Science 282: 1315-1317, Nov. 13, 1998.*
Van de Loo et al, PNAS, USA 92: 6743-6747, Jul. 1995.*
Doerks et al, TIG 14(6): 248-250, Jun. 1998.*
Bork, Peer, et al., "Go hunting in sequence databases but watch out for traps," *TIG*, vol. 12(10):425-427 (1996).
Brenner, Steven E., "Errors in genome annotation," *TIG*, vol. 15(4):132-133 (1999).
Broun, Pierre, et al., "Catalytic Plasticity of Fatty Acid Modification Enzymes Underlying Chemical Diversity of Plant Lipids," *Science* vol. 282:1315-1317 (1998).
De Luca, Vincenzo, "Molecular characterization of secondary metabolic pathways," *AgBiotech News and Information*, vol. 5(6):225N-229N, (1993).
Doerks, Tobias, et al., "Protein annotation: detective work for function prediction," *TIG*, vol. 14(6):248-250 (1998).
Girke, Thomas, et al., "Identification of a novel Δ6-acyl-group desaturase by targeted gene disruption in *Physcomitrella patens*," *The Plant Journal*, vol. 15(1):39-48 (1998).
Hong, Haiping, et al., "High-Level Production of γ-Linolenic Acid in *Brassica juncea* Using a Δ6 Desaturase from *Pythium irregulare*," *Plant Physiology*, vol. 129:354-362 (2002).
Knutzon, Deborah S., et al., "Identification of Δ5-Desaturase from *Mortierella alpina* by Heterologous Expression in Bakers' Yeast and Canola," *The Journal of Biological Chemistry*, vol. 273(45):29360-29366 (1998).
Michaelson, Louise V., et al., "Functional identification of a fatty acid Δ⁵ desaturase gene from *Caenorhabditis elegans*," *FEBS*, vol. 439:215-218 (1998).
Michaelson, Louise V., et al., "Isolation of a Δ⁵-Fatty Acid Desaturase Gene from *Mortierella alpina*," *The Journal of Biological Chemistry*, vol. 273(30):19055-19059 (1998).
Napier, Johnathan A., et al., "Identification of a *Caenorhabditis elegans* Δ⁶-fatty-acid-desaturase by heterologous expression in *Saccharomyces cerevisiae*," *Biochem. J.*, vol. 330:611-614 (1998).
Qiu, Xiao, et al., "Identification of a Δ4 Fatty Acid Desaturase from *Thraustochytrium* sp. Involved in the Biosynthesis of Docosahexanoic Acid by Heterologous Expression in *Saccharomyces cerevisiae* and *Brassica juncea*," *The Journal of Biological Chemistry*, vol. 276(34):31561-31566 (2001).
Saito, Tomao, et al., "Identification of Δ⁵-fatty acid desaturase from the cellular slime mold *Dictyostelium discoideum*," *Eur. J. Biochem.*, vol. 265:809-814 (1999).

(Continued)

*Primary Examiner*—Elizabeth F McElwain
(74) *Attorney, Agent, or Firm*—Connolly Bove Lodge & Hutz LLP

(57) ABSTRACT

The invention provides isolated nucleic acid molecules which encode novel fatty acid desaturase family members. The invention also provides recombinant expression vectors containing desaturase nucleic acid molecules, host cells into which the expression vectors have been introduced, and methods for large-scale production of long chain polyunsaturated fatty acids (LCPUFAs), e.g., DHA.

13 Claims, 24 Drawing Sheets

OTHER PUBLICATIONS

Sayanova, Olga, et al., "Expression of a borage desaturase cDNA containing an N-terminal cytochrome $b_5$ domain results in the accumulation of high levels of $\Delta^6$-desaturated fatty acids in transgenic tobacco," *Proc. Natl. Acad. Sci.*, vol. 94:4211-4216(1997).

Smith, Temple F., et al., "The challenges of genome sequence annotation or, 'The devil is in the details'," *Nature Biotechnology*, vol. 15:1222-1223 (1997).

Sperling, Petra, et al., "A bifunctional $\Delta^6$-fatty acyl acetylenase/desaturase from the moss *Ceratodon purpureus*," *Eur. J. Biochem.*, vol. 267:3801-3811(2000).

van de Loo, Frank J. eta), "An oleate 12 hydroxylase from *Ricinus communis* L. is a fatty acyl desaturase homolog," *PNAS USA*, vol. 92:6743-6747 (1995).

Watts, Jennifer L., et al., "Isolation and Characterization of a $\Delta^5$-Fatty Acid Desaturase from *Caenorhabditis elegans*," *Biochemistry and Biophysics*, vol. 362(1):175-182 (1999).

Hong, Haiping et al., "Isolation and Characterization of a $\Delta 5$ FA Desaturase from *Pythium irregulare* by Heterologous Expression in *Saccharomyces cerevisiae* and Oilseed Crops," *Lipids*, vol. 37(9):863-868 (2002).

Huang, Yung-Sheng et al., "Cloning of $\Delta 12$- and $\Delta 6$-Desaturases from *Mortierella alpina* and Recombinant Production of γ-Linolenic Acid in *Saccharomyces cerevisiae*," *Lipids*, vol. 34(7):649-659 (1999).

Sakuradani, Eiji et al., "$\Delta 6$-Fatty acid desaturase from an arachidonic acid-producing *Mortierella* fungus, Gene cloning and its heterologous expression in a fungus, *Aspergillus*," *Gene*, vol. 238:445-453 (1999).

Sambrook, J. et al., Molecular Cloning, a Laboratory Manual, Second Edition, Cold Spring Harbor Laboratory Press, pp. 11.4 and 14.15 (1989).

Wu, Guohai et al., "Stepwise engineering to produce high yields of very long-chain polyunsaturated fatty acids in plants," *Nature Biotechnology*, vol. 23(8);1013-1017 (2005).

Partial European Search Report for Application No. 07019867.6-1212, dated Mar. 31, 2008.

Saito, T., et al., "A Second Functional $\Delta 5$ Fatty Acid Desaturase in the Cellular Slime Mould *Dictyostelium discoideum*", Eur. J. Biochem., 2000, vol. 267, pp. 1813-1818.

Notice of Reasons for Rejection dated Jul. 29, 2009 issued in JP Appl. No. 2009-076067 and the English translation thereof.

O'Brien, D. J., et al., "Production of Eicosapentaenoic Acid by the Filamentous Fungus *Pythium irrequlare*", Applied Microbiology and Biotechnology, 1993, vol. 40, pp. 211-214.

Pankhurst, C. E., et al., "The Usefulness of Fatty Acid Analysis in Differentiating Species of *Pythium, Rhizoctonia and Gaeumannomyces* and as a Tool for their Detection in Infected Wheat Roots", Australasian Plant Pathology, 2001, vol. 30, pp. 191-197.

Communication Pursuant to Article 94(3) EPC dated Aug. 24, 2009 Issued in European Application No. 07019867.6.

* cited by examiner

ATGACGGTCGGCTACGACGAGGAGATCCCGTTCGAGCAGGTCCGCGCGCACAACAAGCCGGA
TGACGCCTGGTGCGCGATCCACGGGCACGTGTACGATGTGACCAAGTTCGCGAGCGTGCACCC
GGGCGGCGACATTATCCTGCTGGCCGCAGGCAAGGAGGCCACCGTGCTGTACGAGACTTACC
ATGTGCGGGGCGTCTCGGACGCGGTGCTGCGCAAGTACCGCATCGGCAAGCTGCCGGACGGC
CAAGGCGGCGCGAACGAGAAGGAAAAGCGGACGCTCTCGGGCCTCTCGTCGGCCTCGTACTA
CACGTGGAACAGCGACTTTTACAGGGTAATGCGCGAGCGCGTCGTGGCTCGGCTCAAGGAGC
GCGGCAAGGCCCGCCGCGGAGGCTACGAGCTCTGGATCAAGGCGTTCCTGCTGCTCGTCGGCT
TCTGGAGCTCGCTGTACTGGATGTGCACGCTGGACCCCTCGTTCGGGGCCATCCTGGCCGCCA
TGTCGCTGGGCGTCTTTGCCGCCTTTGTGGGCACGTGCATCCAGCACGACGGCAACCACGGCG
CCTTTGCCCAGTCGCGATGGGTCAACAAGGTTGCCGGGTGGACGCTCGACATGATCGGCGCCA
GCGGCATGACGTGGGAGTTCCAGCACGTCCTGGGCCACCATCCGTACACGAACCTGATCGAG
GAGGAGAACGGCCTGCAAAAGGTGAGCGGCAAGAAGATGGACACCAAGCTGGCCGACCAGG
AGAGCGATCCGGACGTCTTTTCCACGTACCCGATGATGCGCCTGCACCCGTGGCACCAGAAGC
GCTGGTACCACCGTTTCCAGCACATTTACGGCCCCTTCATCTTTGGCTTCATGACCATCAACAA
GGTGGTCACGCAGGACGTCGGTGTGGTGCTCCGCAAGCGGCTCTTCCAGATTGACGCCGAGTG
CCGGTACGCGAGCCCAATGTACGTGGCGCGTTTCTGGATCATGAAGGCGCTCACGGTGCTCTA
CATGGTGGCCCTGCCGTGCTACATGCAGGGCCCGTGGCACGGCCTCAAGCTGTTCGCGATCGC
GCACTTTACGTGCGGCGAGGTGCTCGCAACCATGTTCATTGTGAACCACATCATCGAGGGCGT
CTCGTACGCTTCCAAGGACGCGGTCAAGGGCACGATGGCGCCGCCGAAGACGATGCACGGCG
TGACGCCCATGAACAACACGCGCAAGGAGGTGGAGGCGGAGGCGTCCAAGTCTGGCGCCGTG
GTCAAGTCAGTCCCGCTCGACGACTGGGCCGTCGTCCAGTGCCAGACCTCGGTGAACTGGAGC
GTCGGCTCGTGGTTCTGGAATCACTTTTCCGGCGGCCTCAACCACCAGATTGAGCACCACCTG
TTCCCCGGRCTCAGCCACGAGACGTACTACCACATTCAGGACGTCTTTCAGTCCACCTGCGCC
GAGTACGGCGTCCCGTACCAGCACGAGCCTTCGCTCTGGACCGCGTACTGGAAGATGCTCGAG
CACCTCCGTCAGCTCGGCAATGAGGAGACCCACGAGTCCTGGCAGCGCGCTGCCTGA

Fig. 1A

MTVGYDEEIPFEQVRAHNKPDDAWCAIHGHVYDVTKFASVHPGGDIILLAAGKEATVLYETYHV
RGVSDAVLRKYRIGKLPDGQGGANEKEKRTLSGLSSASYYTWNSDFYRVMRERVVARLKERGKA
RRGGYELWIKAFLLLVGFWSSLYWMCTLDPSFGAILAAMSLGVFAAFVGTCIQHDGNHGAFAQS
RWVNKVAGWTLDMIGASGMTWEFQHVLGHHPYTNLIEEENGLQKVSGKKMDTKLADQESDPD
VFSTYPMMRLHPWHQKRWYHRFQHIYGPFIFGFMTINKVVTQDVGVVLRKRLFQIDAECRYASP
MYVARFWIMKALTVLYMVALPCYMQGPWHGLKLFAIAHFTCGEVLATMFIVNHIIEGVSYASKD
AVKGTMAPPKTMHGVTPMNNTRKEVEAEASKSGAVVKSVPLDDWAVVQCQTSVNWSVGSWF
WNHFSGGLNHQIEHHLFPGLSHETYYHIQDVFQSTCAEYGVPYQHEPSLWTAYWKMLEHLRQLG
NEETHESWQRAA

Fig. 1B

```
ATGGGCAAGGGCAGCGAGGGCCGCAGCGCGGCGCGCGAGATGACGGCCGAGGCGAACGGCG
ACAAGCGGAAAACGATTCTGATCGAGGGCGTCCTGTACGACGCGACGAACTTTAAGCACCCG
GGCGGTTCGATCATCAACTTCTTGACCGAGGGCGAGGCCGGCGTGGACGCGACGCAGGCGTA
CCGCGAGTTTCATCAGCGGTCCGGCAAGGCCGACAAGTACCTCAAGTCGCTGCCGAAGCTGG
ATGCGTCCAAGGTGGAGTCGCGGTTCTCGGCCAAAGAGCAGGCGCGGCGCGACGCCATGACG
CGCGACTACGCGGCCTTTCGCGAGGAGCTCGTCGCCGAGGGGTACTTTGACCCGTCGATCCCG
CACATGATTTACCGCGTCGTGGAGATCGTGGCGCTCTTCGCGCTCTCGTTCTGGCTCATGTCCA
AGGCCTCGCCCACCTCGCTCGTGCTGGGCGTGGTGATGAACGGCATTGCGCAGGGCCGCTGCG
GCTGGGTCATGCACGAGATGGGCCACGGGTCGTTCACGGGCGTCATCTGGCTCGACGACCGG
ATGTGCGAGTTCTTCTACGGCGTCGGCTGCGGCATGAGCGGGCACTACTGGAAGAACCAGCA
CAGCAAGCACCACGCCGCGCCCAACCGCCTCGAGCACGATGTCGATCTCAACACGCTGCCCCT
GGTCGCCTTTAACGAGCGCGTCGTGCGCAAGGTCAAGCCGGGATCGCTGCTGGCGCTCTGGCT
GCGCGTGCAGGCGTACCTCTTTGCGCCCGTCTCGTGCCTGCTCATCGGCCTTGGCTGGACGCTC
TACCTGCACCCGCGCTACATGCTGCGCACCAAGCGGCACATGGAGTTCGTCTGGATCTTCGCG
CGCTACATTGGCTGGTTCTCGCTCATGGGCGCTCTCGGCTACTCGCCGGGCACCTCGGTCGGG
ATGTACCTGTGCTCGTTCGGCCTCGGCTGCATTTACATTTTCCTGCAGTTCGCCGTCAGCCACA
CGCACCTGCCGGTGACCAACCCGGAGGACCAGCTGCACTGGCTCGAGTACGCGGCCGACCAC
ACGGTGAACATTAGCACCAAGTCCTGGCTCGTCACGTGGTGGATGTCGAACCTGAACTTTCAG
ATCGAGCACCACCTCTTCCCCACGGCGCCGCAGTTCCGCTTCAAGGAAATCAGTCCTCGCGTC
GAGGCCCTCTTCAAGCGCCACAACCTCCCGTACTACGACCTGCCCTACACGAGCGCGGTCTCG
ACCACCTTTGCCAATCTTTATTCCGTCGGCCACTCGGTCGGCGCCGACACCAAGAAGCAGGAC
TGA
```

Fig. 2A

```
MGKGSEGRSAAREMTAEANGDKRKTILIEGVLYDATNFKHPGGSIINFLTEGEAGVDATQAYREF
HQRSGKADKYLKSLPKLDASKVESRFSAKEQARRDAMTRDYAAFREELVAEGYFDPSIPHMIYRV
VEIVALFALSFWLMSKASPTSLVLGVVMNGIAQGRCGWVMHEMGHGSFTGVIWLDDRMCEFFY
GVGCGMSGHYWKNQHSKHHAAPNRLEHDVDLNTLPLVAFNERVVRKVKPGSLLALWLRVQAY
LFAPVSCLLIGLGWTLYLHPRYMLRTKRHMEFVWIFARYIGWFSLMGALGYSPGTSVGMYLCSFG
LGCIYIFLQFAVSHTHLPVTNPEDQLHWLEYAADHTVNISTKSWLVTWWMSNLNFQIEHHLFPTA
PQFRFKEISPRVEALFKRHNLPYYDLPYTSAVSTTFANLYSVGHSVGADTKKQD
```

Fig. 2B

```
FAD4 - MTVGYDEEIPFEQVRAHNKPDDAWCAIHGHVYDVTKFASVHPGGDIIL-L      -50
           |   | |||      |      ||    |    |  |||| |||  |
FAD5 - MGKGSEGRSAAREMTAEANGDKRKTILIEGVLYDATNFK-HPGGSIINFL      -50
                                               →
FAD4 - AGKEATVLYETYHVRGVSDAVLRKYRIGKLPDGQGGANEKEKRTLSGLSS     -100
         |    |   |  |    || |     |        ||    |    |
FAD5 - EGEAGVDATQAYREFHQRSGKADKY-LKSLPKLDAS---KVESRFSAKEQ      -96

FAD4 - ASYYTWNSDFYRVMRERVVARLKERGKARRGGYELWIKAFLLLVGFWSSL     -150
        |   |    |  |      |            |     |  |    ||
FAD5 - ARRDAMTRDYAAFREELVAEGYFDPSIPHMI-----YRVVEIVALFALSF     -141

FAD4 - YWMCTLDPSFGAILAAMSLGVFAAFVGTCIQHDGNHGAFAQSRWVNKVAG     -200
         |   |      ||    |   |    ||||| ||||   |   |
FAD5 - WLMSKASPTSLVLGVVMN-G-IAQGRCGWVMHEMGHGSFTGVIWLDDRMC     -185

FAD4 - WTLDMIGASGMTWEFQHVLGHHPYTNLIEEENGLQKVSGKKMDTKLADQE     -250
         |||   |   |  ||||||| |    |
FAD5 - FYGVGCGMSGHYWKNQHSK-HHAAPNRLEHDVDLNT--------------     -226

FAD4 - SDPDVFSTYPMMRLHPWHQKRWYHRFQHIYGPFIFGFMTINKVVTQDVGV     -300
          |      |    |          |     |      |     |
FAD5 - LPLVAFNERVVRKVKPGSLLALWLRVQ------AYLFAPVSCLLIGLGWT     -270

FAD4 - VLRKRLFQIDAECRYASPMYVARFWIMKALTVLYMVALPCYMQGPWHGLK     -350
                                 ||   |
FAD5 - LYLHPRYMLRTKRHMEFVWIFARYIGWFSLMGALGYSPGT----------     -310

FAD4 - LFAIAHFTCGEVLATMFIVNHIIEGVSYASKDAVKGTMAPPKTMHGVTPM     -400
         |   |   |                              |   ||
FAD5 - --SVGMYLCSFGLGCIYIFLQF----------------AVSHTHLPVTNP     -342

FAD4 - NNTRKEVEAEASKSGAVVKSVPLDDWAVVQCQTSVNWSVGSWFWNHFSGG     -450
          |     |                              ||| ||
FAD5 - EDQLHWLEYAADHT--------------------VNISTKSWLVTWWMSN     -372

FAD4 - LNHQIEHHLFPGLSHETYYHIQDVFQSTCAEYGVPYQHEPSLWTAYWKML     -500
        |||||||||| |    |                    ||   |
FAD5 - LNFQIEHHLFPTAPQFRFKEISPRVEALFKRHNLPY-YDLPYTSAVSTTF     -421
          ←

FAD4 - EHLRQLGNEETHESWQRAA    -519
         |  |
FAD5 - ANLYSVGHSVGADT-KKQD    -439
```

Fig. 3

```
ATGACCGAGAAGGCGAGTGACGAGTTCACGTGGCAGGAGGTCGCCAAGCACAACACGGCCA
AGAGCGCGTGGGTGATCATCCGCGGCGAGGTGTACGACGTGACCGAGTGGGCGGACAAGCAC
CCGGGCGGCAGCGAGCTCATCGTCCTGCACTCCGGTCGTGAATGCACGGACACGTTCTACTCG
TACCACCCGTTCTCGAACCGCGCCGACAAGATCTTGGCCAAGTACAAGATCGGCAAGCTCGTG
GGCGGCTACGAGTTCCCGGTGTTCAAGCCGGACTCGGGCTTCTACAAGGAATGCTCGGAGCGC
GTGGCCGAGTACTTTAAGACGAACAATCTGGACCCAAAGGCGGCGTTCGCGGGTCTCTGGCG
CATGGTGTTCGTGTTCGCGGTCGCCGCGCTCGCGTACATGGGCATGAATGAGCTCATCCCTGG
AAACGTGTACGCGCAGTACGCGTGGGGCGTGGTGTTCGGTGTCTTCCAGGCGCTGCCATTGCT
GCACGTGATGCACGACTCGTCGCACGCGGCATGCTCGAGCAGCCCAGCGATGTGGCAGATCA
TCGGTCGTGGTGTGATGGACTGGTTCGCTGGCGCCAGCATGGTGTCGTGGTTGAACCAGCACG
TTGTGGGCCACCACATCTACACGAACGTCGCGGGCGCGGACCCGGATCTCCCGGTCGACTTTG
AGAGCGACGTGCGCCGCATCGTGCACCGCCAGGTGCTGCTGCCGATCTACAAGTTCCAGCACA
TCTACCTGCCACCGCTCTACGGCGTGCTGGGCCTCAAGTTCCGCATCCAGGACGTGTTCGAGA
CGTTCGTGTCGCTCACGAACGGCCCGGTGCGTGTGAACCCGCACCCGGTGTCGGACTGGGTGC
AAATGATCTTCGCCAAGGCGTTCTGGACGTTCTACCGCATCTACATCCCGTTGGCGTGGCTCA
AGATCACGCCGTCGACGTTCTGGGGCGTGTTTTTCCTCGCCGAGTTCACCACAGGTTGGTACCT
CGCGTTCAACTTCCAGGTGAGCCACGTCTCGACCGAGTGCGAGTACCCGTGCGGTGATGCGCC
GTCGGCCGAGGTCGGTGACGAGTGGGCGATCTCGCAGGTCAAGTCGTCGGTGGACTACGCGC
ACGGCTCGCCGCTCGCGGCGTTCCTCTGCGGCGCGCTCAACTACCAGGTGACCCACCACTTGT
ACCCGGGCATCTCACAGTACCACTACCCTGCGATCGCGCCGATCATCATCGACGTGTGCAAGA
AGTACAACATCAAGTACACGGTGCTGCCGACGTTCACCGAGGCGCTGCTCGCGCACTTCAAGC
ACCTGAAGAACATGGGCGAGCTCGGCAAGCCCGTGGAGATCCACATGGGTTAA
```

Fig. 4A

```
MTEKASDEFTWQEVAKHNTAKSAWVIIRGEVYDVTEWADKHPGGSELIVLHSGRECTDTFYSYH
PFSNRADKILAKYKIGKLVGGYEFPVFKPDSGFYKECSERVAEYFKTNNLDPKAAFAGLWRMVFV
FAVAALAYMGMNELIPGNVYAQYAWGVVFGVFQALPLLHVMHDSSHAACSSSPAMWQIIGRGV
MDWFAGASMVSWLNQHVVGHHIYTNVAGADPDLPVDFESDVRRIVHRQVLLPIYKFQHIYLPPL
YGVLGLKFRIQDVFETFVSLTNGPVRVNPHPVSDWVQMIFAKAFWTFYRIYIPLAWLKITPSTFWG
VFFLAEFTTGWYLAFNFQVSHVSTECEYPCGDAPSAEVGDEWAISQVKSSVDYAHGSPLAAFLCG
ALNYQVTHHLYPGISQYHYPAIAPIIIDVCKKYNIKYTVLPTFTEALLAHFKHLKNMGELGKPVEIH
MG
```

Fig. 4B

```
ATGGTGGACCTCAAGCCTGGAGTGAAGCGCCTGGTGAGCTGGAAGGAGATCCGCGAGCACGC
GACGCCCGCGACCGCGTGGATCGTGATTCACCACAAGGTCTACGACATCTCCAAGTGGGACTC
GCACCCGGGTGGCTCCGTGATGCTCACGCAGGCCGGCGAGGACGCCACGGACGCCTTCGCGG
TCTTCCACCCGTCCTCGGCGCTCAAGCTGCTCGAGCAGTTCTACGTCGGCGACGTGGACGAAA
CCTCCAAGGCCGAGATCGAGGGGGAGCCGGCGAGCGACGAGGAGCGCGCGCGCCGCGAGCG
CATCAACGAGTTCATCGCGTCCTACCGTCGTCTGCGCGTCAAGGTCAAGGGCATGGGGCTCTA
CGACGCCAGCGCGCTCTACTACGCGTGGAAGCTCGTGAGCACGTTCGGCATCGCGGTGCTCTC
GATGGCGATCTGCTTCTTCTTCAACAGTTTCGCCATGTACATGGTCGCCGGCGTGATTATGGGG
CTCTTCTACCAGCAGTCCGGATGGCTGGCGCACGACTTCTTGCACAACCAGGTGTGCGAGAAC
CGCACGCTCGGCAACCTTATCGGCTGCCTCGTGGGCAACGCCTGGCAGGGCTTCAGCGTGCAG
TGGTGGAAGAACAAGCACAACCTGCACCACGCGGTGCCGAACCTGCACAGCGCCAAGGACGA
GGGCTTCATCGGCGACCCGGACATCGACACCATGCCGCTGCTGGCGTGGTCTAAGGAGATGG
CGCGCAAGGCGTTCGAGTCGGCGCACGGCCCGTTCTTCATCCGCAACCAGGCGTTCCTATACT
TCCCGCTGCTGCTGCTCGCGCGCCTGAGCTGGCTCGCGCAGTCGTTCTTCTACGTGTTCACCGA
GTTCTCGTTCGGCATCTTCGACAAGGTCGAGTTCGACGGACCGGAGAAGGCGGGTCTGATCGT
GCACTACATCTGGCAGCTCGCGATCCCGTACTTCTGCAACATGAGCCTGTTTGAGGGCGTGGC
ATACTTCCTCATGGGCCAGGCGTCCTGCGGCTTGCTCCTGGCGCTGGTGTTCAGTATTGGCCAC
AACGGCATGTCGGTGTACGAGCGCGAAACCAAGCCGGACTTCTGGCAGCTGCAGGTGACCAC
GACGCGCAACATCCGCGCGTCGGTATTCATGGACTGGTTCACCGGTGGCTTGAACTACCAGAT
CGACCATCACCTGTTCCCGCTCGTGCCGCGCCACAACTTGCCAAAGGTCAACGTGCTCATCAA
GTCGCTATGCAAGGAGTTCGACATCCCGTTCCACGAGACCGGCTTCTGGGAGGGCATCTACGA
GGTCGTGGACCACCTGGCGGACATCAGCAAGGAATTCATCACCGAGTTCCCAGCGATGTAA
```

Fig. 5A

```
MVDLKPGVKRLVSWKEIREHATPATAWIVIHHKVYDISKWDSHPGGSVMLTQAGEDATDAFAVF
HPSSALKLLEQFYVGDVDETSKAEIEGEPASDEERARRERINEFIASYRRLRVKVKGMGLYDASAL
YYAWKLVSTFGIAVLSMAICFFFNSFAMYMVAGVIMGLFYQQSGWLAHDFLHNQVCENRTLGNL
IGCLVGNAWQGFSVQWWKNKHNLHHAVPNLHSAKDEGFIGDPDIDTMPLLAWSKEMARKAFES
AHGPFFIRNQAFLYFPLLLLARLSWLAQSFFYVFTEFSFGIFDKVEFDGPEKAGLIVHYIWQLAIPYF
CNMSLFEGVAYFLMGQASCGLLLALVFSIGHNGMSVYERETKPDFWQLQVTTTRNIRASVFMDW
FTGGLNYQIDHHLFPLVPRHNLPKVNVLIKSLCKEFDIPFHETGFWEGIYEVVDHLADISKEFITEFP
AM
```

Fig. 5B

```
Fad5-2  MTEKASDE---FTWQEVAKHNTAKSAWVIIRGEVYDVTEWAD KHPGGS EL   47
         |       |      || ||    |||       |   ||||||
Fad6    MVDLKPGVKRLVSWKEIREHATPATAWIVIHHKVYDISKW-D SHPGGS VM   49
                                                →

Fad5-2  IVLHSGRECTDTFYSYHPFSNRADKILAKYKIGKLVGGYEFPVF-KPDSG     96
          |    |||  ||   ||    |||     |   |            ||
Fad6    LT-QAGEDATDAFAVFHP--SSALKLLEQFYVGDVDETSKAEIEGEPASD     96

Fad5-2  FYKECSERVAEYFKT-NNLDPKAAFAGL---------WRMVFVFAVAALA    136
          |   |    |    |    |  ||        |   |    |||
Fad6    EERARRERINEFIASYRRLRVKVKGMGLYDASALYYAWKLVSTFGIAVLS    146

Fad5-2  YMGMNELIPGNVYAQY-AWGVVFGVFQALPLLHVM HDSSHA ACSSSPAMW   185
          |       |       ||   |     |      |||
Fad6    -MAICFFF--NSFAMYMVAGVIMGLFYQQSGW-LA HDFLHN QVCENRTLG   192

Fad5-2  QIIGRGVMDWFAGASMVSWLNQ HVVGHH IYTNVAGADPDLPVDFESDVRR   235
          ||    ||   ||       |   ||
Fad6    NLIGCLVGNAWQGFSVQWWKNK HNLHHA VPNLHSAKDEGFIGDPDIDTMP   242

Fad5-2  IVHRQVLL----------PIYKFQHIYLP-PLYGVLGLKFRIQDVFETFV    274
                             |   ||        |      |
Fad6    LLAWSKEMARKAFESAHGPFFIRNQAFLYFPLLLLARLSWLAQSFFYVFT    292

Fad5-2  SLTNGPVRVNPHPVSDWVQMIFAKAFWTFYRIYIPLAWLKITPSTFWGVF    324
              |       |         |      |   |               |
Fad6    EFSFGIFDKVEFDGPEKAGLI-VHYIWQLAIPYFCNMSL-FEGVAY---F    337

Fad5-2  FLAEFTTGWYLAFNFQVSHVSTECEYPCGDAPSAEVGDEWAISQVKSSVD    374
          |  |||  |          |           |      |       ||
Fad6    LMGQASCGLLLALVFSIGH-NGMSVYERETKP-----DFWQL-QVTTTRN    380

Fad5-2  YAHGSPLAAFLCGALNYQVT HHLYPG ISQYHYPAIAPIIIDVCKKYNIKY   424
          |         |    ||||| ||||      |         ||     |
Fad6    I-RASVFMDWFTGGLNYQID HHLFPL VPRHNLPKVNVLIKSLCKEFDIPF   429
                                ←

Fad5-2  TVLPTFTEALLAHFKHLKNMGELGKP--VEIHMG   456
          ||                    |     |
Fad6    HE-TGFGEGI---YEVVDHLADISKEFITEFPAM   459
```

Fig. 6

Table 1. Fatty Acid Profiles of *Thraustochytrium sp.* (w%)

| Fatty Acids | 18:3 (n-6) | 18:4 (n-3) | 20:4 (n-6) | 20:5 (n-3) | 22:4 (n-6) | 22:5 (n-6) | 22:5 (n-3) | DHA (n-3) |
|---|---|---|---|---|---|---|---|---|
| W% | 0.1 | 0.2 | 0.3 | 1.0 | 0.2 | 5.3 | 0.6 | 16.7 |

Fig. 23

Table 2. Fatty Acid Profiles of *Pythium irregulare* (w%)

| 16:0 | 16:1 | 18:0 | 18:1 | 18:2 (LA) | 18:3 (GLA) | 18:3 (ALA) | 20:4 (AA) | 20:5 (EPA) |
|---|---|---|---|---|---|---|---|---|
| 16.2 | 5.5 | 0.9 | 8.9 | 15.3 | <0.1 | <0.1 | 8.9 | 20.3 |

Fig. 24

Table 3. Conversion of exogenous fatty acids in yeast AMY-2αpFad5-2

| Substrate | Substrate accumulation (w%) | Product | Product accumulation (w%) |
|---|---|---|---|
| 16:1(9Z) | 24.41 | 16:2(5Z,9Z) | 0.47 |
| 18:1(9Z) | 11.88 | 18:2(5Z,9Z) | 1.26 |
| 18:1(11Z) | 6.15 | 18:2(5Z,11Z) | 0.85 |
| 18:1(11E) | 4.57 | 18:2(5Z,11E) | 0.08 |
| 18:1(12E) | 4.77 | 18:2(5Z,12E) | 0.09 |
| 18:1(15Z) | 4.55 | 18:2(5Z,15Z) | 0 |
| 18:2(9Z,12Z) | 3.59 | 18:3(5Z,9Z,12Z) | 0.09 |
| 18:3(9Z,12Z,15Z) | 30.71 | 18:4(5Z,9Z,12Z,15Z) | 0.07 |
| 20:2(11Z, 14Z) | 8.59 | 20:3(5Z,11Z,14Z) | 2.08 |
| 20:3(8Z,11Z,14Z) | 14.54 | 20:4(5Z,8Z,11Z,14Z) | 3.68 |
| 20:3(11Z,14Z,17Z) | 2.29 | 20:4(5Z,11Z,14Z,17Z) | 1.08 |

Fig. 25

Table 4. Accumulation of $\Delta 5$-UPIFAs in transgenic flaxseeds expressing *Fad5-2* under the control of the napin (Napin) and flax seed-specific (Cnl) promoters. The fatty acid levels are shown as the weight percentage of total fatty acids.

| Fatty acids | 18:1 (9) | 18:2 (5,9) | 18:2 9,12) | 18:3 (5,9,12) | 18:3 (9,12,15) | 18:4 (5,9,12,15) |
|---|---|---|---|---|---|---|
| Wild Type | 17.4 | 0 | 14.9 | 0 | 56.6 | 0 |
| Cnl-5-2 | 19.9 | 6.8 | 7.1 | 0.5 | 55.6 | 0.7 |
| Cnl-10-1 | 29.1 | 9.3 | 5.1 | 0.4 | 47.6 | 0.4 |
| Cnl-15-3 | 23.9 | 7.1 | 7.1 | 0.4 | 51.6 | 0.5 |
| Napin-5-4 | 41.0 | 0.4 | 7.5 | 0 | 42.1 | 0 |
| Napin-6-1 | 46.7 | 0.3 | 5.3 | 0 | 39.1 | 0 |
| Napin-12-3 | 46.3 | 0.6 | 5.3 | 0 | 39.3 | 0 |

Fig. 26

Table 5. Accumulation of Δ6 desaturated fatty acids in transgenic flaxseeds (Solin and Normandy) expressing *Fad6* under the control of the napin promoter. The fatty acid levels are shown as the weight percentages of the total fatty acids.

| Transgenic lines | Linoleic acid | Gamma-linolenic acid | Alpha-linolenic acid | Stearidonic acid |
|---|---|---|---|---|
| S-wild type | 71.1 | 0 | 2.1 | 0 |
| S-1-2 | 64.5 | 1.3 | 2.3 | 0.1 |
| S-2-1 | 67.1 | 4.3 | 2.5 | 0.1 |
| S-3-3 | 62.4 | 2.9 | 2.0 | 0.1 |
| N-wild type | 14.9 | 0 | 56.6 | 0 |
| N-5-3 | 7.0 | 0.6 | 51.9 | 1.4 |
| N-6-2 | 6.2 | 0.3 | 43.7 | 0.9 |
| N-7-5 | 4.5 | 0.5 | 49.9 | 0.6 |
| N-11-3 | 7.5 | 0.4 | 49.6 | 0.8 |
| N-13-1 | 5.9 | 0.3 | 41.8 | 0.5 |

Notes: S, Solin type: N, Normandy-traditional type of flax

Fig. 27

SEQUENCE LISTING

```
<160> NUMBER OF SEQ ID NOS: 10

<210> SEQ ID NO 1
<211> LENGTH: 1560
<212> TYPE: DNA
<213> ORGANISM: Thraustochytrium sp.
<220> FEATURE:
<221> NAME/KEY: CDS
<222> LOCATION: (1)...(1560)
<220> FEATURE:
<221> NAME/KEY: VARIANT
<222> LOCATION: 462
<223> OTHER INFORMATION: Xaa = Gly

<400> SEQUENCE: 1 atg acg gtc ggc tac gac gag gag atc ccg ttc gag cag gtc cgc gcg      48
Met Thr Val Gly Tyr Asp Glu Glu Ile Pro Phe Glu Gln Val Arg Ala
1               5                  10                  15 cac aac aag ccg gat gac gcc tgg tgc gcg atc cac ggg cac gtg tac      96
His Asn Lys Pro Asp Asp Ala Trp Cys Ala Ile His Gly His Val Tyr
            20                  25                  30 gat gtg acc aag ttc gcg agc gtg cac ccg ggc ggc gac att atc ctg     144
Asp Val Thr Lys Phe Ala Ser Val His Pro Gly Gly Asp Ile Ile Leu
        35                  40                  45 ctg gcc gca ggc aag gag gcc acc gtg ctg tac gag act tac cat gtg     192
Leu Ala Ala Gly Lys Glu Ala Thr Val Leu Tyr Glu Thr Tyr His Val
    50                  55                  60 cgg ggc gtc tcg gac gcg gtg ctg cgc aag tac cgc atc ggc aag ctg     240
Arg Gly Val Ser Asp Ala Val Leu Arg Lys Tyr Arg Ile Gly Lys Leu
65                  70                  75                  80 ccg gac ggc caa ggc ggc gcg aac gag aag gaa aag cgg acg ctc tcg     288
Pro Asp Gly Gln Gly Gly Ala Asn Glu Lys Glu Lys Arg Thr Leu Ser
                85                  90                  95 ggc ctc tcg tcg gcc tcg tac tac acg tgg aac agc gac ttt tac agg     336
Gly Leu Ser Ser Ala Ser Tyr Tyr Thr Trp Asn Ser Asp Phe Tyr Arg
            100                 105                 110 gta atg cgc gag cgc gtc gtg gct cgg ctc aag gag cgc ggc aag gcc     384
Val Met Arg Glu Arg Val Val Ala Arg Leu Lys Glu Arg Gly Lys Ala
        115                 120                 125 cgc cgc gga ggc tac gag ctc tgg atc aag gcg ttc ctg ctc ctc gtc     432
Arg Arg Gly Gly Tyr Glu Leu Trp Ile Lys Ala Phe Leu Leu Leu Val
    130                 135                 140 ggc ttc tgg agc tcg ctg tac tgg atg tgc acg ctg gac ccc tcg ttc     480
Gly Phe Trp Ser Ser Leu Tyr Trp Met Cys Thr Leu Asp Pro Ser Phe
145                 150                 155                 160 ggg gcc atc ctg gcc gcc atg tcg ctg ggc gtc ttt gcc gcc ttt gtg     528
Gly Ala Ile Leu Ala Ala Met Ser Leu Gly Val Phe Ala Ala Phe Val
                165                 170                 175 ggc acg tgc atc cag cac gac ggc aac cac ggc gcc ttt gcc cag tcg     576
```

|   |   |   |   |   |   |   |   |   |   |   |   |   |   |   |   |
|---|---|---|---|---|---|---|---|---|---|---|---|---|---|---|---|
| Gly | Thr | Cys | Ile | Gln | His | Asp | Gly | Asn | His | Gly | Ala | Phe | Ala | Gln | Ser |
|   |   |   | 180 |   |   |   |   | 185 |   |   |   |   | 190 |   |   |

```
cga tgg gtc aac aag gtt gcc ggg tgg acg ctc gac atg atc ggc gcc      624
Arg Trp Val Asn Lys Val Ala Gly Trp Thr Leu Asp Met Ile Gly Ala
        195                 200                 205 agc ggc atg acg tgg gag ttc cag cac gtc ctg ggc cac cat ccg tac      672
Ser Gly Met Thr Trp Glu Phe Gln His Val Leu Gly His His Pro Tyr
    210                 215                 220 acg aac ctg atc gag gag gag aac ggc ctg caa aag gtg agc ggc aag      720
Thr Asn Leu Ile Glu Glu Glu Asn Gly Leu Gln Lys Val Ser Gly Lys
225                 230                 235                 240 aag atg gac acc aag ctg gcc gac cag gag agc gat ccg gac gtc ttt      768
Lys Met Asp Thr Lys Leu Ala Asp Gln Glu Ser Asp Pro Asp Val Phe
                245                 250                 255 tcc acg tac ccg atg atg cgc ctg cac ccg tgg cac cag aag cgc tgg      816
Ser Thr Tyr Pro Met Met Arg Leu His Pro Trp His Gln Lys Arg Trp
            260                 265                 270 tac cac cgt ttc cag cac att tac ggc ccc ttc atc ttt ggc ttc atg      864
Tyr His Arg Phe Gln His Ile Tyr Gly Pro Phe Ile Phe Gly Phe Met
        275                 280                 285 acc atc aac aag gtg gtc acg cag gac gtc ggt gtg gtg ctc cgc aag      912
Thr Ile Asn Lys Val Val Thr Gln Asp Val Gly Val Val Leu Arg Lys
    290                 295                 300 cgg ctc ttc cag att gac gcc gag tgc cgg tac gcg agc cca atg tac      960
Arg Leu Phe Gln Ile Asp Ala Glu Cys Arg Tyr Ala Ser Pro Met Tyr
305                 310                 315                 320 gtg gcg cgt ttc tgg atc atg aag gcg ctc acg gtg ctc tac atg gtg     1008
Val Ala Arg Phe Trp Ile Met Lys Ala Leu Thr Val Leu Tyr Met Val
                325                 330                 335 gcc ctg ccg tgc tac atg cag ggc ccg tgg cac ggc ctc aag ctg ttc     1056
Ala Leu Pro Cys Tyr Met Gln Gly Pro Trp His Gly Leu Lys Leu Phe
            340                 345                 350 gcg atc gcg cac ttt acg tgc ggc gag gtg ctc gca acc atg ttc att     1104
Ala Ile Ala His Phe Thr Cys Gly Glu Val Leu Ala Thr Met Phe Ile
        355                 360                 365 gtg aac cac atc atc gag ggc gtc tcg tac gct tcc aag gac gcg gtc     1152
Val Asn His Ile Ile Glu Gly Val Ser Tyr Ala Ser Lys Asp Ala Val
    370                 375                 380 aag ggc acg atg gcg ccg ccg aag acg atg cac ggc gtg acg ccc atg     1200
Lys Gly Thr Met Ala Pro Pro Lys Thr Met His Gly Val Thr Pro Met
385                 390                 395                 400 aac aac acg cgc aag gag gtg gag gcg gag gcg tcc aag tct ggc gcc     1248
Asn Asn Thr Arg Lys Glu Val Glu Ala Glu Ala Ser Lys Ser Gly Ala
                405                 410                 415 gtg gtc aag tca gtc ccg ctc gac gac tgg gcc gtc gtc cag tgc cag     1296
Val Val Lys Ser Val Pro Leu Asp Asp Trp Ala Val Val Gln Cys Gln
            420                 425                 430 acc tcg gtg aac tgg agc gtc ggc tcg tgg ttc tgg aat cac ttt tcc     1344
Thr Ser Val Asn Trp Ser Val Gly Ser Trp Phe Trp Asn His Phe Ser
        435                 440                 445 ggc ggc ctc aac cac cag att gag cac cac ctg ttc ccc ggr ctc agc     1392
Gly Gly Leu Asn His Gln Ile Glu His His Leu Phe Pro Xaa Leu Ser
    450                 455                 460 cac gag acg tac tac cac att cag gac gtc ttt cag tcc acc tgc gcc     1440
His Glu Thr Tyr Tyr His Ile Gln Asp Val Phe Gln Ser Thr Cys Ala
465                 470                 475                 480 gag tac ggc gtc ccg tac cag cac gag cct tcg ctc tgg acc gcg tac     1488
Glu Tyr Gly Val Pro Tyr Gln His Glu Pro Ser Leu Trp Thr Ala Tyr
                485                 490                 495
```

```
tgg aag atg ctc gag cac ctc cgt cag ctc ggc aat gag gag acc cac    1536
Trp Lys Met Leu Glu His Leu Arg Gln Leu Gly Asn Glu Glu Thr His
        500                 505                 510 gag tcc tgg cag cgc gct gcc tga                                    1560
Glu Ser Trp Gln Arg Ala Ala *
        515

<210> SEQ ID NO 2
<211> LENGTH: 519
<212> TYPE: PRT
<213> ORGANISM: Thraustochytrium sp.
<220> FEATURE:
<221> NAME/KEY: VARIANT
<222> LOCATION: 462
<223> OTHER INFORMATION: Xaa = Gly

<400> SEQUENCE: 2

Met Thr Val Gly Tyr Asp Glu Glu Ile Pro Phe Glu Gln Val Arg Ala
  1               5                  10                  15

His Asn Lys Pro Asp Asp Ala Trp Cys Ala Ile His Gly His Val Tyr
             20                  25                  30

Asp Val Thr Lys Phe Ala Ser Val His Pro Gly Gly Asp Ile Ile Leu
         35                  40                  45

Leu Ala Ala Gly Lys Glu Ala Thr Val Leu Tyr Glu Thr Tyr His Val
 50                  55                  60

Arg Gly Val Ser Asp Ala Val Leu Arg Lys Tyr Arg Ile Gly Lys Leu
 65                  70                  75                  80

Pro Asp Gly Gln Gly Gly Ala Asn Glu Lys Glu Lys Arg Thr Leu Ser
                 85                  90                  95

Gly Leu Ser Ser Ala Ser Tyr Tyr Thr Trp Asn Ser Asp Phe Tyr Arg
            100                 105                 110

Val Met Arg Glu Arg Val Val Ala Arg Leu Lys Glu Arg Gly Lys Ala
        115                 120                 125

Arg Arg Gly Gly Tyr Glu Leu Trp Ile Lys Ala Phe Leu Leu Leu Val
130                 135                 140

Gly Phe Trp Ser Ser Leu Tyr Trp Met Cys Thr Leu Asp Pro Ser Phe
145                 150                 155                 160

Gly Ala Ile Leu Ala Ala Met Ser Leu Gly Val Phe Ala Ala Phe Val
                165                 170                 175

Gly Thr Cys Ile Gln His Asp Gly Asn His Gly Ala Phe Ala Gln Ser
            180                 185                 190

Arg Trp Val Asn Lys Val Ala Gly Trp Thr Leu Asp Met Ile Gly Ala
        195                 200                 205

Ser Gly Met Thr Trp Glu Phe Gln His Val Leu Gly His His Pro Tyr
210                 215                 220

Thr Asn Leu Ile Glu Glu Asn Gly Leu Gln Lys Val Ser Gly Lys
225                 230                 235                 240

Lys Met Asp Thr Lys Leu Ala Asp Gln Glu Ser Asp Pro Asp Val Phe
                245                 250                 255

Ser Thr Tyr Pro Met Met Arg Leu His Pro Trp His Gln Lys Arg Trp
            260                 265                 270

Tyr His Arg Phe Gln His Ile Tyr Gly Pro Phe Ile Phe Gly Phe Met
        275                 280                 285

Thr Ile Asn Lys Val Val Thr Gln Asp Val Gly Val Val Leu Arg Lys
290                 295                 300

Arg Leu Phe Gln Ile Asp Ala Glu Cys Arg Tyr Ala Ser Pro Met Tyr
305                 310                 315                 320
```

```
Val Ala Arg Phe Trp Ile Met Lys Ala Leu Thr Val Leu Tyr Met Val
                325                 330                 335

Ala Leu Pro Cys Tyr Met Gln Gly Pro Trp His Gly Leu Lys Leu Phe
            340                 345                 350

Ala Ile Ala His Phe Thr Cys Gly Glu Val Leu Ala Thr Met Phe Ile
                355                 360             365

Val Asn His Ile Ile Glu Gly Val Ser Tyr Ala Ser Lys Asp Ala Val
            370                 375                 380

Lys Gly Thr Met Ala Pro Pro Lys Thr Met His Gly Val Thr Pro Met
385                 390                 395                 400

Asn Asn Thr Arg Lys Glu Val Glu Ala Glu Ala Ser Lys Ser Gly Ala
                405                 410                 415

Val Val Lys Ser Val Pro Leu Asp Asp Trp Ala Val Val Gln Cys Gln
            420                 425                 430

Thr Ser Val Asn Trp Ser Val Gly Ser Trp Phe Trp Asn His Phe Ser
                435                 440                 445

Gly Gly Leu Asn His Gln Ile Glu His His Leu Phe Pro Xaa Leu Ser
            450                 455                 460

His Glu Thr Tyr Tyr His Ile Gln Asp Val Phe Gln Ser Thr Cys Ala
465                 470                 475                 480

Glu Tyr Gly Val Pro Tyr Gln His Glu Pro Ser Leu Trp Thr Ala Tyr
                485                 490                 495

Trp Lys Met Leu Glu His Leu Arg Gln Leu Gly Asn Glu Glu Thr His
            500                 505                 510

Glu Ser Trp Gln Arg Ala Ala
            515

<210> SEQ ID NO 3
<211> LENGTH: 1320
<212> TYPE: DNA
<213> ORGANISM: Thraustochytrium sp.
<220> FEATURE:
<221> NAME/KEY: CDS
<222> LOCATION: (1)...(1320)

<400> SEQUENCE: 3 atg ggc aag ggc agc gag ggc cgc agc gcg gcg cgc gag atg acg gcc    48
Met Gly Lys Gly Ser Glu Gly Arg Ser Ala Ala Arg Glu Met Thr Ala
 1               5                  10                  15 gag gcg aac ggc gac aag cgg aaa acg att ctg atc gag ggc gtc ctg    96
Glu Ala Asn Gly Asp Lys Arg Lys Thr Ile Leu Ile Glu Gly Val Leu
             20                  25                  30 tac gac gcg acg aac ttt aag cac ccg ggc ggt tcg atc atc aac ttc   144
Tyr Asp Ala Thr Asn Phe Lys His Pro Gly Gly Ser Ile Ile Asn Phe
         35                  40                  45 ttg acc gag ggc gag gcc ggc gtg gac gcg acg cag gcg tac cgc gag   192
Leu Thr Glu Gly Glu Ala Gly Val Asp Ala Thr Gln Ala Tyr Arg Glu
     50                  55                  60 ttt cat cag cgg tcc ggc aag gcc gac aag tac ctc aag tcg ctg ccg   240
Phe His Gln Arg Ser Gly Lys Ala Asp Lys Tyr Leu Lys Ser Leu Pro
 65                  70                  75                  80 aag ctg gat gcg tcc aag gtg gag tcg cgg ttc tcg gcc aaa gag cag   288
Lys Leu Asp Ala Ser Lys Val Glu Ser Arg Phe Ser Ala Lys Glu Gln
                 85                  90                  95 gcg cgg cgc gac gcc atg acg cgc gac tac gcg gcc ttt cgc gag gag   336
Ala Arg Arg Asp Ala Met Thr Arg Asp Tyr Ala Ala Phe Arg Glu Glu
            100                 105                 110
```

```
ctc gtc gcc gag ggg tac ttt gac ccg tcg atc ccg cac atg att tac    384
Leu Val Ala Glu Gly Tyr Phe Asp Pro Ser Ile Pro His Met Ile Tyr
        115                 120                 125 cgc gtc gtg gag atc gtg gcg ctc ttc gcg ctc tcg ttc tgg ctc atg    432
Arg Val Val Glu Ile Val Ala Leu Phe Ala Leu Ser Phe Trp Leu Met
130                 135                 140 tcc aag gcc tcg ccc acc tcg ctc gtg ctg ggc gtg gtg atg aac ggc    480
Ser Lys Ala Ser Pro Thr Ser Leu Val Leu Gly Val Val Met Asn Gly
145                 150                 155                 160 att gcg cag ggc cgc tgc ggc tgg gtc atg cac gag atg ggc cac ggg    528
Ile Ala Gln Gly Arg Cys Gly Trp Val Met His Glu Met Gly His Gly
            165                 170                 175 tcg ttc acg ggc gtc atc tgg ctc gac gac cgg atg tgc gag ttc ttc    576
Ser Phe Thr Gly Val Ile Trp Leu Asp Asp Arg Met Cys Glu Phe Phe
                180                 185                 190 tac ggc gtc ggc tgc ggc atg agc ggg cac tac tgg aag aac cag cac    624
Tyr Gly Val Gly Cys Gly Met Ser Gly His Tyr Trp Lys Asn Gln His
            195                 200                 205 agc aag cac cac gcc gcg ccc aac cgc ctc gag cac gat gtc gat ctc    672
Ser Lys His His Ala Ala Pro Asn Arg Leu Glu His Asp Val Asp Leu
        210                 215                 220 aac acg ctg ccc ctg gtc gcc ttt aac gag cgc gtg gtg cgc aag gtc    720
Asn Thr Leu Pro Leu Val Ala Phe Asn Glu Arg Val Val Arg Lys Val
225                 230                 235                 240 aag ccg gga tcg ctg ctg gcg ctc tgg ctg cgc gtg cag gcg tac ctc    768
Lys Pro Gly Ser Leu Leu Ala Leu Trp Leu Arg Val Gln Ala Tyr Leu
            245                 250                 255 ttt gcg ccc gtc tcg tgc ctg ctc atc ggc ctt ggc tgg acg ctc tac    816
Phe Ala Pro Val Ser Cys Leu Leu Ile Gly Leu Gly Trp Thr Leu Tyr
                260                 265                 270 ctg cac ccg cgc tac atg ctg cgc acc aag cgg cac atg gag ttc gtc    864
Leu His Pro Arg Tyr Met Leu Arg Thr Lys Arg His Met Glu Phe Val
            275                 280                 285 tgg atc ttc gcg cgc tac att ggc tgg ttc tcg ctc atg ggc gct ctc    912
Trp Ile Phe Ala Arg Tyr Ile Gly Trp Phe Ser Leu Met Gly Ala Leu
        290                 295                 300 ggc tac tcg ccg ggc acc tcg gtc ggg atg tac ctg tgc tcg ttc ggc    960
Gly Tyr Ser Pro Gly Thr Ser Val Gly Met Tyr Leu Cys Ser Phe Gly
305                 310                 315                 320 ctc ggc tgc att tac att ttc ctg cag ttc gcc gtc agc cac acg cac   1008
Leu Gly Cys Ile Tyr Ile Phe Leu Gln Phe Ala Val Ser His Thr His
            325                 330                 335 ctg ccg gtg acc aac ccg gag gac cag ctg cac tgg ctc gag tac gcg   1056
Leu Pro Val Thr Asn Pro Glu Asp Gln Leu His Trp Leu Glu Tyr Ala
                340                 345                 350 gcc gac cac acg gtg aac att agc acc aag tcc tgg ctc gtc acg tgg   1104
Ala Asp His Thr Val Asn Ile Ser Thr Lys Ser Trp Leu Val Thr Trp
            355                 360                 365 tgg atg tcg aac ctg aac ttc cag atc gag cac cac ctc ttc ccc acg   1152
Trp Met Ser Asn Leu Asn Phe Gln Ile Glu His His Leu Phe Pro Thr
        370                 375                 380 gcg ccg cag ttc cgc ttc aag gaa atc agt cct cgc gtc gag gcc ctc   1200
Ala Pro Gln Phe Arg Phe Lys Glu Ile Ser Pro Arg Val Glu Ala Leu
385                 390                 395                 400 ttc aag cgc cac aac ctc ccg tac tac gac ctg ccc tac acg agc gcg   1248
Phe Lys Arg His Asn Leu Pro Tyr Tyr Asp Leu Pro Tyr Thr Ser Ala
            405                 410                 415 gtc tcg acc acc ttt gcc aat ctt tat tcc gtc ggc cac tcg gtc ggc   1296
Val Ser Thr Thr Phe Ala Asn Leu Tyr Ser Val Gly His Ser Val Gly
                420                 425                 430
```

```
gcc gac acc aag aag cag gac tga                                          1320
Ala Asp Thr Lys Lys Gln Asp *
        435
```

<210> SEQ ID NO 4
<211> LENGTH: 439
<212> TYPE: PRT
<213> ORGANISM: Thraustochytrium sp.

<400> SEQUENCE: 4

```
Met Gly Lys Gly Ser Glu Gly Arg Ser Ala Ala Arg Glu Met Thr Ala
  1               5                  10                  15

Glu Ala Asn Gly Asp Lys Arg Lys Thr Ile Leu Ile Glu Gly Val Leu
             20                  25                  30

Tyr Asp Ala Thr Asn Phe Lys His Pro Gly Gly Ser Ile Ile Asn Phe
         35                  40                  45

Leu Thr Glu Gly Glu Ala Gly Val Asp Ala Thr Gln Ala Tyr Arg Glu
     50                  55                  60

Phe His Gln Arg Ser Gly Lys Ala Asp Lys Tyr Leu Lys Ser Leu Pro
 65                  70                  75                  80

Lys Leu Asp Ala Ser Lys Val Glu Ser Arg Phe Ser Ala Lys Glu Gln
                 85                  90                  95

Ala Arg Arg Asp Ala Met Thr Arg Asp Tyr Ala Ala Phe Arg Glu Glu
            100                 105                 110

Leu Val Ala Glu Gly Tyr Phe Asp Pro Ser Ile Pro His Met Ile Tyr
        115                 120                 125

Arg Val Val Glu Ile Val Ala Leu Phe Ala Leu Ser Phe Trp Leu Met
    130                 135                 140

Ser Lys Ala Ser Pro Thr Ser Leu Val Leu Gly Val Val Met Asn Gly
145                 150                 155                 160

Ile Ala Gln Gly Arg Cys Gly Trp Val Met His Glu Met Gly His Gly
                165                 170                 175

Ser Phe Thr Gly Val Ile Trp Leu Asp Asp Arg Met Cys Glu Phe Phe
            180                 185                 190

Tyr Gly Val Gly Cys Gly Met Ser Gly His Tyr Trp Lys Asn Gln His
        195                 200                 205

Ser Lys His His Ala Ala Pro Asn Arg Leu Glu His Asp Val Asp Leu
    210                 215                 220

Asn Thr Leu Pro Leu Val Ala Phe Asn Glu Arg Val Val Arg Lys Val
225                 230                 235                 240

Lys Pro Gly Ser Leu Leu Ala Leu Trp Leu Arg Val Gln Ala Tyr Leu
                245                 250                 255

Phe Ala Pro Val Ser Cys Leu Leu Ile Gly Leu Gly Trp Thr Leu Tyr
            260                 265                 270

Leu His Pro Arg Tyr Met Leu Arg Thr Lys Arg His Met Glu Phe Val
        275                 280                 285

Trp Ile Phe Ala Arg Tyr Ile Gly Trp Phe Ser Leu Met Gly Ala Leu
    290                 295                 300

Gly Tyr Ser Pro Gly Thr Ser Val Gly Met Tyr Leu Cys Ser Phe Gly
305                 310                 315                 320

Leu Gly Cys Ile Tyr Ile Phe Leu Gln Phe Ala Val Ser His Thr His
                325                 330                 335

Leu Pro Val Thr Asn Pro Glu Asp Gln Leu His Trp Leu Glu Tyr Ala
            340                 345                 350
```

```
Ala Asp His Thr Val Asn Ile Ser Thr Lys Ser Trp Leu Val Thr Trp
        355                 360                 365

Trp Met Ser Asn Leu Asn Phe Gln Ile Glu His His Leu Phe Pro Thr
        370                 375                 380

Ala Pro Gln Phe Arg Phe Lys Glu Ile Ser Pro Arg Val Glu Ala Leu
385                 390                 395                 400

Phe Lys Arg His Asn Leu Pro Tyr Tyr Asp Leu Pro Tyr Thr Ser Ala
                405                 410                 415

Val Ser Thr Thr Phe Ala Asn Leu Tyr Ser Val Gly His Ser Val Gly
                420                 425                 430

Ala Asp Thr Lys Lys Gln Asp
            435

<210> SEQ ID NO 5
<211> LENGTH: 1371
<212> TYPE: DNA
<213> ORGANISM: Thraustochytrium sp.
<220> FEATURE:
<221> NAME/KEY: CDS
<222> LOCATION: (1)...(1371)

<400> SEQUENCE: 5
```

| | | | | | | | | | | | | | | | | |
|---|---|---|---|---|---|---|---|---|---|---|---|---|---|---|---|---|
| atg acc gag aag gcg agt gac gag ttc acg tgg cag gag gtc gcc aag | | | | | | | | | | | | | | | | 48 |
| Met Thr Glu Lys Ala Ser Asp Glu Phe Thr Trp Gln Glu Val Ala Lys | | | | | | | | | | | | | | | | |
| 1               5                   10                  15 | | | | | | | | | | | | | | | | |

```
cac aac acg gcc aag agc gcg tgg gtg atc atc cgc ggc gag gtg tac      96
His Asn Thr Ala Lys Ser Ala Trp Val Ile Ile Arg Gly Glu Val Tyr
            20                  25                  30 gac gtg acc gag tgg gcg gac aag cac ccg ggc ggc agc gag ctc atc     144
Asp Val Thr Glu Trp Ala Asp Lys His Pro Gly Gly Ser Glu Leu Ile
        35                  40                  45 gtc ctg cac tcc ggt cgt gaa tgc acg gac acg ttc tac tcg tac cac     192
Val Leu His Ser Gly Arg Glu Cys Thr Asp Thr Phe Tyr Ser Tyr His
    50                  55                  60 ccg ttc tcg aac cgc gcc gac aag atc ttg gcc aag tac aag atc ggc     240
Pro Phe Ser Asn Arg Ala Asp Lys Ile Leu Ala Lys Tyr Lys Ile Gly
65                  70                  75                  80 aag ctc gtg ggc ggc tac gag ttc ccg gtg ttc aag ccg gac tcg ggc     288
Lys Leu Val Gly Gly Tyr Glu Phe Pro Val Phe Lys Pro Asp Ser Gly
                85                  90                  95 ttc tac aag gaa tgc tcg gag cgc gtg gcc gag tac ttt aag acg aac     336
Phe Tyr Lys Glu Cys Ser Glu Arg Val Ala Glu Tyr Phe Lys Thr Asn
            100                 105                 110 aat ctg gac cca aag gcg gcg ttc gcg ggt ctc tgg cgc atg gtg ttc     384
Asn Leu Asp Pro Lys Ala Ala Phe Ala Gly Leu Trp Arg Met Val Phe
        115                 120                 125 gtg ttc gcg gtc gcc gcg ctc gcg tac atg ggc atg aat gag ctc atc     432
Val Phe Ala Val Ala Ala Leu Ala Tyr Met Gly Met Asn Glu Leu Ile
    130                 135                 140 cct gga aac gtg tac gcg cag tac gcg tgg ggc gtg gtg ttc ggt gtc     480
Pro Gly Asn Val Tyr Ala Gln Tyr Ala Trp Gly Val Val Phe Gly Val
145                 150                 155                 160 ttc cag gcg ctg cca ttg ctg cac gtg atg cac gac tcg tcg cac gcg     528
Phe Gln Ala Leu Pro Leu Leu His Val Met His Asp Ser Ser His Ala
                165                 170                 175 gca tgc tcg agc agc cca gcg atg tgg cag atc atc ggt cgt ggt gtg     576
Ala Cys Ser Ser Ser Pro Ala Met Trp Gln Ile Ile Gly Arg Gly Val
            180                 185                 190 atg gac tgg ttc gct ggc gcc agc atg gtg tcg tgg ttg aac cag cac     624
Met Asp Trp Phe Ala Gly Ala Ser Met Val Ser Trp Leu Asn Gln His
```

-continued

```
                195                 200                 205
gtt gtg ggc cac cac atc tac acg aac gtc gcg ggc gcg gac ccg gat      672
Val Val Gly His His Ile Tyr Thr Asn Val Ala Gly Ala Asp Pro Asp
210                 215                 220 ctc ccg gtc gac ttt gag agc gac gtg cgc cgc atc gtg cac cgc cag      720
Leu Pro Val Asp Phe Glu Ser Asp Val Arg Arg Ile Val His Arg Gln
225                 230                 235                 240 gtg ctg ctg cca atc tac aag ttc cag cac atc tac ctg cca ccg ctc      768
Val Leu Leu Pro Ile Tyr Lys Phe Gln His Ile Tyr Leu Pro Pro Leu
                245                 250                 255 tac ggc gtg ctg ggc ctc aag ttc cgc atc cag gac gtg ttc gag acg      816
Tyr Gly Val Leu Gly Leu Lys Phe Arg Ile Gln Asp Val Phe Glu Thr
            260                 265                 270 ttc gtg tcg ctc acg aac ggc ccg gtg cgt gtg aac ccg cac ccg gtg      864
Phe Val Ser Leu Thr Asn Gly Pro Val Arg Val Asn Pro His Pro Val
        275                 280                 285 tcg gac tgg gtg caa atg atc ttc gcc aag gcg ttc tgg acg ttc tac      912
Ser Asp Trp Val Gln Met Ile Phe Ala Lys Ala Phe Trp Thr Phe Tyr
    290                 295                 300 cgc atc tac atc ccg ttg gcg tgg ctc aag atc acg ccg tcg acg ttc      960
Arg Ile Tyr Ile Pro Leu Ala Trp Leu Lys Ile Thr Pro Ser Thr Phe
305                 310                 315                 320 tgg ggc gtg ttt ttc ctc gcc gag ttc acc aca ggt tgg tac ctc gcg     1008
Trp Gly Val Phe Phe Leu Ala Glu Phe Thr Thr Gly Trp Tyr Leu Ala
                325                 330                 335 ttc aac ttc cag gtg agc cac gtc tcg acc gag tgc gag tac ccg tgc     1056
Phe Asn Phe Gln Val Ser His Val Ser Thr Glu Cys Glu Tyr Pro Cys
            340                 345                 350 ggt gat gcg ccg tcg gcc gag gtc ggt gac gag tgg gcg atc tcg cag     1104
Gly Asp Ala Pro Ser Ala Glu Val Gly Asp Glu Trp Ala Ile Ser Gln
        355                 360                 365 gtc aag tcg tcg gtg gac tac gcg cac ggc tcg ccg ctc gcg gcg ttc     1152
Val Lys Ser Ser Val Asp Tyr Ala His Gly Ser Pro Leu Ala Ala Phe
    370                 375                 380 ctc tgc ggc gcg ctc aac tac cag gtg acc cac cac ttg tac ccg ggc     1200
Leu Cys Gly Ala Leu Asn Tyr Gln Val Thr His His Leu Tyr Pro Gly
385                 390                 395                 400 atc tca cag tac cac tac cct gcg atc gcg ccg atc atc atc gac gtg     1248
Ile Ser Gln Tyr His Tyr Pro Ala Ile Ala Pro Ile Ile Ile Asp Val
                405                 410                 415 tgc aag aag tac aac atc aag tac acg gtg ctg ccg acg ttc acc gag     1296
Cys Lys Lys Tyr Asn Ile Lys Tyr Thr Val Leu Pro Thr Phe Thr Glu
            420                 425                 430 gcg ctc ctc gcg cac ttc aag cac ctg aag aac atg ggc gag ctc ggc     1344
Ala Leu Leu Ala His Phe Lys His Leu Lys Asn Met Gly Glu Leu Gly
        435                 440                 445 aag ccc gtg gag atc cac atg ggt taa                                 1371
Lys Pro Val Glu Ile His Met Gly  *
    450                 455
```

<210> SEQ ID NO 6
<211> LENGTH: 456
<212> TYPE: PRT
<213> ORGANISM: Thraustochytrium sp.

<400> SEQUENCE: 6

```
Met Thr Glu Lys Ala Ser Asp Glu Phe Thr Trp Gln Glu Val Ala Lys
1               5                   10                  15

His Asn Thr Ala Lys Ser Ala Trp Val Ile Ile Arg Gly Glu Val Tyr
            20                  25                  30
```

-continued

```
Asp Val Thr Glu Trp Ala Asp Lys His Pro Gly Gly Ser Glu Leu Ile
         35                  40                  45

Val Leu His Ser Gly Arg Glu Cys Thr Asp Thr Phe Tyr Ser Tyr His
 50                  55                  60

Pro Phe Ser Asn Arg Ala Asp Lys Ile Leu Ala Lys Tyr Lys Ile Gly
 65                  70                  75                  80

Lys Leu Val Gly Gly Tyr Glu Phe Pro Val Phe Lys Pro Asp Ser Gly
                 85                  90                  95

Phe Tyr Lys Glu Cys Ser Glu Arg Val Ala Glu Tyr Phe Lys Thr Asn
             100                 105                 110

Asn Leu Asp Pro Lys Ala Ala Phe Ala Gly Leu Trp Arg Met Val Phe
         115                 120                 125

Val Phe Ala Val Ala Ala Leu Ala Tyr Met Gly Met Asn Glu Leu Ile
 130                 135                 140

Pro Gly Asn Val Tyr Ala Gln Tyr Ala Trp Gly Val Phe Gly Val
 145                 150                 155                 160

Phe Gln Ala Leu Pro Leu Leu His Val Met His Asp Ser Ser His Ala
                 165                 170                 175

Ala Cys Ser Ser Pro Ala Met Trp Gln Ile Ile Gly Arg Gly Val
             180                 185                 190

Met Asp Trp Phe Ala Gly Ala Ser Met Val Ser Trp Leu Asn Gln His
         195                 200                 205

Val Val Gly His His Ile Tyr Thr Asn Val Ala Gly Ala Asp Pro Asp
 210                 215                 220

Leu Pro Val Asp Phe Glu Ser Asp Val Arg Arg Ile Val His Arg Gln
225                 230                 235                 240

Val Leu Leu Pro Ile Tyr Lys Phe Gln His Ile Tyr Leu Pro Pro Leu
                 245                 250                 255

Tyr Gly Val Leu Gly Leu Lys Phe Arg Ile Gln Asp Val Phe Glu Thr
             260                 265                 270

Phe Val Ser Leu Thr Asn Gly Pro Val Arg Val Asn Pro His Pro Val
         275                 280                 285

Ser Asp Trp Val Gln Met Ile Phe Ala Lys Ala Phe Trp Thr Phe Tyr
 290                 295                 300

Arg Ile Tyr Ile Pro Leu Ala Trp Leu Lys Ile Thr Pro Ser Thr Phe
305                 310                 315                 320

Trp Gly Val Phe Phe Leu Ala Glu Phe Thr Thr Gly Trp Tyr Leu Ala
                 325                 330                 335

Phe Asn Phe Gln Val Ser His Val Ser Thr Glu Cys Glu Tyr Pro Cys
             340                 345                 350

Gly Asp Ala Pro Ser Ala Glu Val Gly Asp Glu Trp Ala Ile Ser Gln
         355                 360                 365

Val Lys Ser Ser Val Asp Tyr Ala His Gly Ser Pro Leu Ala Ala Phe
 370                 375                 380

Leu Cys Gly Ala Leu Asn Tyr Gln Val Thr His His Leu Tyr Pro Gly
385                 390                 395                 400

Ile Ser Gln Tyr His Tyr Pro Ala Ile Ala Pro Ile Ile Asp Val
                 405                 410                 415

Cys Lys Lys Tyr Asn Ile Lys Tyr Thr Val Leu Pro Thr Phe Thr Glu
             420                 425                 430

Ala Leu Leu Ala His Phe Lys His Leu Lys Asn Met Gly Glu Leu Gly
         435                 440                 445
```

-continued

```
Lys Pro Val Glu Ile His Met Gly
    450                 455

<210> SEQ ID NO 7
<211> LENGTH: 1380
<212> TYPE: DNA
<213> ORGANISM: Thraustochytrium sp.
<220> FEATURE:
<221> NAME/KEY: CDS
<222> LOCATION: (1)...(1380)

<400> SEQUENCE: 7 atg gtg gac ctc aag cct gga gtg aag cgc ctg gtg agc tgg aag gag        48
Met Val Asp Leu Lys Pro Gly Val Lys Arg Leu Val Ser Trp Lys Glu
  1               5                  10                  15 atc cgc gag cac gcg acg ccc gcg acc gcg tgg atc gtg att cac cac        96
Ile Arg Glu His Ala Thr Pro Ala Thr Ala Trp Ile Val Ile His His
                 20                  25                  30 aag gtc tac gac atc tcc aag tgg gac tcg cac ccg ggt ggc tcc gtg       144
Lys Val Tyr Asp Ile Ser Lys Trp Asp Ser His Pro Gly Gly Ser Val
             35                  40                  45 atg ctc acg cag gcc ggc gag gac gcc acg gac gcc ttc gcg gtc ttc       192
Met Leu Thr Gln Ala Gly Glu Asp Ala Thr Asp Ala Phe Ala Val Phe
         50                  55                  60 cac ccg tcc tcg gcg ctc aag ctg ctc gag cag ttc tac gtc ggc gac       240
His Pro Ser Ser Ala Leu Lys Leu Leu Glu Gln Phe Tyr Val Gly Asp
 65                  70                  75                  80 gtg gac gaa acc tcc aag gcc gag atc gag ggg gag ccg gcg agc gac       288
Val Asp Glu Thr Ser Lys Ala Glu Ile Glu Gly Glu Pro Ala Ser Asp
                 85                  90                  95 gag gag cgc gcg cgc cgc gag cgc atc aac gag ttc atc gcg tcc tac       336
Glu Glu Arg Ala Arg Arg Glu Arg Ile Asn Glu Phe Ile Ala Ser Tyr
            100                 105                 110 cgt cgt ctg cgc gtc aag gtc aag ggc atg ggg ctc tac gac gcc agc       384
Arg Arg Leu Arg Val Lys Val Lys Gly Met Gly Leu Tyr Asp Ala Ser
        115                 120                 125 gcg ctc tac tac gcg tgg aag ctc gtg agc acg ttc ggc atc gcg gtg       432
Ala Leu Tyr Tyr Ala Trp Lys Leu Val Ser Thr Phe Gly Ile Ala Val
    130                 135                 140 ctc tcg atg gcg atc tgc ttc ttc ttc aac agt ttc gcc atg tac atg       480
Leu Ser Met Ala Ile Cys Phe Phe Phe Asn Ser Phe Ala Met Tyr Met
145                 150                 155                 160 gtc gcc ggc gtg att atg ggg ctc ttc tac cag cag tcc gga tgg ctg       528
Val Ala Gly Val Ile Met Gly Leu Phe Tyr Gln Gln Ser Gly Trp Leu
                165                 170                 175 gcg cac gac ttc ttg cac aac cag gtg tgc gag aac cgc acg ctc ggc       576
Ala His Asp Phe Leu His Asn Gln Val Cys Glu Asn Arg Thr Leu Gly
            180                 185                 190 aac ctt atc ggc tgc ctc gtg ggc aac gcc tgg cag ggc ttc agc gtg       624
Asn Leu Ile Gly Cys Leu Val Gly Asn Ala Trp Gln Gly Phe Ser Val
        195                 200                 205 cag tgg tgg aag aac aag cac aac ctg cac cac gcg gtg ccg aac ctg       672
Gln Trp Trp Lys Asn Lys His Asn Leu His His Ala Val Pro Asn Leu
    210                 215                 220 cac agc gcc aag gac gag ggc ttc atc ggc gac ccg gac atc gac acc       720
His Ser Ala Lys Asp Glu Gly Phe Ile Gly Asp Pro Asp Ile Asp Thr
225                 230                 235                 240 atg ccg ctg ctg gcg tgg tct aag gag atg gcg cgc aag gcg ttc gag       768
Met Pro Leu Leu Ala Trp Ser Lys Glu Met Ala Arg Lys Ala Phe Glu
                245                 250                 255 tcg gcg cac ggc ccg ttc ttc atc cgc aac cag gcg ttc cta tac ttc       816
```

```
Ser Ala His Gly Pro Phe Phe Ile Arg Asn Gln Ala Phe Leu Tyr Phe
            260                 265                 270 ccg ctg ctg ctg ctc gcg cgc ctg agc tgg ctc gcg cag tcg ttc ttc         864
Pro Leu Leu Leu Leu Ala Arg Leu Ser Trp Leu Ala Gln Ser Phe Phe
        275                 280                 285 tac gtg ttc acc gag ttc tcg ttc ggc atc ttc gac aag gtc gag ttc         912
Tyr Val Phe Thr Glu Phe Ser Phe Gly Ile Phe Asp Lys Val Glu Phe
    290                 295                 300 gac gga ccg gag aag gcg ggt ctg atc gtg cac tac atc tgg cag ctc         960
Asp Gly Pro Glu Lys Ala Gly Leu Ile Val His Tyr Ile Trp Gln Leu
305                 310                 315                 320 gcg atc ccg tac ttc tgc aac atg agc ctg ttt gag ggc gtg gca tac        1008
Ala Ile Pro Tyr Phe Cys Asn Met Ser Leu Phe Glu Gly Val Ala Tyr
                325                 330                 335 ttc ctc atg ggc cag gcg tcc tgc ggc ttg ctc ctg gcg ctg gtg ttc        1056
Phe Leu Met Gly Gln Ala Ser Cys Gly Leu Leu Leu Ala Leu Val Phe
            340                 345                 350 agt att ggc cac aac ggc atg tcg gtg tac gag cgc gaa acc aag ccg        1104
Ser Ile Gly His Asn Gly Met Ser Val Tyr Glu Arg Glu Thr Lys Pro
        355                 360                 365 gac ttc tgg cag ctg cag gtg acc acg acg cgc aac atc cgc gcg tcg        1152
Asp Phe Trp Gln Leu Gln Val Thr Thr Thr Arg Asn Ile Arg Ala Ser
370                 375                 380 gta ttc atg gac tgg ttc acc ggt ggc ttg aac tac cag atc gac cat        1200
Val Phe Met Asp Trp Phe Thr Gly Gly Leu Asn Tyr Gln Ile Asp His
385                 390                 395                 400 cac ctg ttc ccg ctc gtg ccg cgc cac aac ttg cca aag gtc aac gtg        1248
His Leu Phe Pro Leu Val Pro Arg His Asn Leu Pro Lys Val Asn Val
                405                 410                 415 ctc atc aag tcg cta tgc aag gag ttc gac atc ccg ttc cac gag acc        1296
Leu Ile Lys Ser Leu Cys Lys Glu Phe Asp Ile Pro Phe His Glu Thr
            420                 425                 430 ggc ttc tgg gag ggc atc tac gag gtc gtg gac cac ctg gcg gac atc        1344
Gly Phe Trp Glu Gly Ile Tyr Glu Val Val Asp His Leu Ala Asp Ile
        435                 440                 445 agc aag gaa ttc atc acc gag ttc cca gcg atg taa                        1380
Ser Lys Glu Phe Ile Thr Glu Phe Pro Ala Met  *
    450                 455

<210> SEQ ID NO 8
<211> LENGTH: 459
<212> TYPE: PRT
<213> ORGANISM: Thraustochytrium sp.

<400> SEQUENCE: 8

Met Val Asp Leu Lys Pro Gly Val Lys Arg Leu Val Ser Trp Lys Glu
 1               5                  10                  15

Ile Arg Glu His Ala Thr Pro Ala Thr Ala Trp Ile Val Ile His His
                20                  25                  30

Lys Val Tyr Asp Ile Ser Lys Trp Asp Ser His Pro Gly Gly Ser Val
            35                  40                  45

Met Leu Thr Gln Ala Gly Glu Asp Ala Thr Asp Ala Phe Ala Val Phe
        50                  55                  60

His Pro Ser Ser Ala Leu Lys Leu Leu Glu Gln Phe Tyr Val Gly Asp
65                  70                  75                  80

Val Asp Glu Thr Ser Lys Ala Glu Ile Glu Gly Pro Ala Ser Asp
                85                  90                  95

Glu Glu Arg Ala Arg Arg Glu Arg Ile Asn Glu Phe Ile Ala Ser Tyr
            100                 105                 110
```

```
Arg Arg Leu Arg Val Lys Val Lys Gly Met Gly Leu Tyr Asp Ala Ser
        115                 120                 125

Ala Leu Tyr Tyr Ala Trp Lys Leu Val Ser Thr Phe Gly Ile Ala Val
    130                 135                 140

Leu Ser Met Ala Ile Cys Phe Phe Asn Ser Phe Ala Met Tyr Met
145                 150                 155                 160

Val Ala Gly Val Ile Met Gly Leu Phe Tyr Gln Gln Ser Gly Trp Leu
                165                 170                 175

Ala His Asp Phe Leu His Asn Gln Val Cys Glu Asn Arg Thr Leu Gly
                180                 185                 190

Asn Leu Ile Gly Cys Leu Val Gly Asn Ala Trp Gln Gly Phe Ser Val
                195                 200                 205

Gln Trp Trp Lys Asn Lys Asn Leu His His Ala Val Pro Asn Leu
    210                 215                 220

His Ser Ala Lys Asp Glu Gly Phe Ile Gly Asp Pro Asp Ile Asp Thr
225                 230                 235                 240

Met Pro Leu Leu Ala Trp Ser Lys Glu Met Ala Arg Lys Ala Phe Glu
                245                 250                 255

Ser Ala His Gly Pro Phe Phe Ile Arg Asn Gln Ala Phe Leu Tyr Phe
                260                 265                 270

Pro Leu Leu Leu Ala Arg Leu Ser Trp Leu Ala Gln Ser Phe Phe
    275                 280                 285

Tyr Val Phe Thr Glu Phe Ser Phe Gly Ile Phe Asp Lys Val Glu Phe
    290                 295                 300

Asp Gly Pro Glu Lys Ala Gly Leu Ile Val His Tyr Ile Trp Gln Leu
305                 310                 315                 320

Ala Ile Pro Tyr Phe Cys Asn Met Ser Leu Phe Glu Gly Val Ala Tyr
                325                 330                 335

Phe Leu Met Gly Gln Ala Ser Cys Gly Leu Leu Leu Ala Leu Val Phe
                340                 345                 350

Ser Ile Gly His Asn Gly Met Ser Val Tyr Glu Arg Glu Thr Lys Pro
                355                 360                 365

Asp Phe Trp Gln Leu Gln Val Thr Thr Thr Arg Asn Ile Arg Ala Ser
    370                 375                 380

Val Phe Met Asp Trp Phe Thr Gly Gly Leu Asn Tyr Gln Ile Asp His
385                 390                 395                 400

His Leu Phe Pro Leu Val Pro Arg His Asn Leu Pro Lys Val Asn Val
                405                 410                 415

Leu Ile Lys Ser Leu Cys Lys Glu Phe Asp Ile Pro Phe His Glu Thr
                420                 425                 430

Gly Phe Trp Glu Gly Ile Tyr Glu Val Val Asp His Leu Ala Asp Ile
                435                 440                 445

Ser Lys Glu Phe Ile Thr Glu Phe Pro Ala Met
    450                 455

<210> SEQ ID NO 9
<211> LENGTH: 23
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: 3, 8, 11, 18, 21
<223> OTHER INFORMATION: n = A,T,C or G
```

```
<400> SEQUENCE: 9
gcncaganga ncactccngg ngg                                              23

<210> SEQ ID NO 10
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: 3, 7, 14
<223> OTHER INFORMATION: n = A,T,C or G

<400> SEQUENCE: 10
atntgtngga gaanagagat ggatg                                            25
```

FAD4, FAD5, FAD5-2, AND FAD6, NOVEL FATTY ACID DESATURASE FAMILY MEMBERS AND USES THEREOF

RELATED APPLICATIONS

This application is a divisional of U.S. application Ser. No. 09/967,477, filed Sep. 28, 2001, which claims priority to U.S. Provisional Application No. 60/236,303 filed on Sep. 28, 2000 and U.S. Provisional Application No. 60/297,562 filed on Jun. 12, 2001, the entire contents of each of which are incorporated herein in their entirety by this reference. The entire contents of all references cited therein also are expressly incorporated by reference and are intended to be part of the present application.

BACKGROUND OF THE INVENTION

Fatty acids are carboxylic acids with long-chain hydrocarbon side groups and play a fundamental role in many biological processes. Fatty acids are rarely free in nature but, rather, occur in esterified form as the major component of lipids. Lipids/fatty acids are sources of energy (e.g., b-oxidation) and are an integral part of cell membranes which are indispensable for processing biological or biochemical information.

Fatty acids can be divided into two groups: the saturated fatty acids and the unsaturated fatty acids which contain one or more carbon double bond in cis-configuration. Unsaturated fatty acids are produced by terminal desaturases that belong to the class of nonheme-iron enzymes. Each of these enzymes are part of a electron-transport system that contains two other proteins, namely cytochrome $b_5$ and NADH-cytochrome $b_5$ reductase. Specifically, such enzymes catalyze the formation of double bonds between the carbon atoms of a fatty acid molecule. Human and other mammals have a limited spectrum of these desaturases that are required for the formation of particular double bonds in unsaturated fatty acids. Thus, humans have to take up some fatty acids through their diet. Such essential fatty acids, for example, are linoleic acid (C18:2); linolenic acid (C18:3), arachidonic acid (C20: 4). In contrast, insects and plants are able to synthesize a much larger variety of unsaturated fatty acids and their derivatives.

Long chain polyunsaturated fatty acids (LCPUFAs) such as docosahexaenoic acid (DHA, 22:6(4,7,10,13,16,19)) are essential components of cell membranes of various tissues and organelles in mammals (nerve, retina, brain and immune cells). For example, over 30% of fatty acids in brain phospholipid are 22:6 (n-3) and 20:4 (n-6). (Crawford, M. A., et al., (1997) Am. J. Clin. Nutr. 66:1032S-1041S). In retina, DHA accounts for more than 60% of the total fatty acids in the rod outer segment, the photosensitive part of the photoreceptor cell. (Giusto, N. M., et al. (2000) Prog. Lipid Res. 39:315-391). Clinical studies have shown that DHA is essential for the growth and development of the brain in infants, and for maintenance of normal brain function in adults (Martinetz, M. (1992) J. Pediatr. 120:S129-S138). DHA also has significant effects on photoreceptor function involved in the signal transduction process, rhodopsin activation, and rod and cone development (Giusto, N. M., et al. (2000) Prog. Lipid Res. 39:315-391). In addition, some positive effects of DHA were also found on diseases such as hypertension, arthritis, atherosclerosis, depression, thrombosis and cancers (Horrocks, L. A. and Yeo, Y. K. (1999) Pharmacol. Res. 40:211-215). Therefore, the appropriate dietary supply of the fatty acid is important for humans to remain healthy. It is particularly important for infant, young children and senior citizens to adequately intake these fatty acids from the diet since they cannot be efficiently synthesized in their body and must be supplemented by food (Spector, A. A. (1999) Lipids 34:S1-S3).

DHA is a fatty acid of the n-3 series according to the location of the last double bond in the methyl end. It is synthesized via alternating steps of desaturation and elongation. Starting with 18:3 (9,12,15), biosynthesis of DHA involves Δ6 desaturation to 18:4 (6,9,12,15), followed by elongation to 20:4 (8,11,14,17) and Δ5 desaturation to 20:5 (5,8,11,14,17). Beyond this point, there are some controversies about the biosynthesis. The conventional view is that 20:5 (5,8,11,14,17) is elongated to 22:5 (7,10,13,16,19) and then converted to 22:6 (4,7,10,13,16,19) by the final Δ4 desaturation (Horrobin, D. F. (1992) Prog. Lipid Res. 31:163-194). However, Sprecher et al. recently suggested an alternative pathway for DHA biosynthesis, which is independent of Δ4 desaturase, involving two consecutive elongations, a Δ6 desaturation and a two-carbon shortening via limited β-oxidation in peroxisome (Sprecher, H., et al. (1995) J. Lipid Res. 36:2471-2477; Sprecher, H., et al. (1999) Lipids 34:S153-S156).

Production of DHA is important because of its beneficial effect on human health. Currently the major sources of DHA are oils from fish and algae. Fish oil is a major and traditional source for this fatty acid, however, it is usually oxidized by the time it is sold. In addition, the supply of the oil is highly variable and its source is in jeopardy with the shrinking fish populations while the algal source is expensive due to low yield and the high costs of extraction.

EPA and AA are both Δ5 essential fatty acids. They form a unique class of food and feed constituents for humans and animals. EPA belongs to the n-3 series with five double bonds in the acyl chain, is found in marine food, and is abundant in oily fish from North Atlantic. AA belongs to the n-6 series with four double bonds. The lack of a double bond in the ω-3 position confers on AA different properties than those found in EPA. The eicosanoids produced from AA have strong inflammatory and platelet aggregating properties, whereas those derived from EPA have anti-inflammatory and anti-platelet aggregating properties. AA can be obtained from some foods such as meat, fish, and eggs, but the concentration is low.

Gamma-linolenic acid (GLA) is another essential fatty acid found in mammals. GLA is the metabolic intermediate for very long chain n-6 fatty acids and for various active molecules. In mammals, formation of long chain polyunsaturated fatty acids is rate-limited by Δ6 desaturation. Many physiological and pathological conditions such as aging, stress, diabetes, eczema, and some infections have been shown to depress the Δ6 desaturation step. In addition, GLA is readily catabolized from the oxidation and rapid cell division associated with certain disorders, e.g., cancer or inflammation. Therefore, dietary supplementation with GLA can reduce the risks of these disorders. Clinical studies have shown that dietary supplementation with GLA is effective in treating some pathological conditions such as atopic eczema, premenstrual syndrome, diabetes, hypercholesterolemia, and inflammatory and cardiovascular disorders.

The predominant sources of GLA are oils from plants such as evening primrose (*Oenothera biennis*), borage (*Borago officinalis* L.), black currant (*Ribes nigrum*), and from microorganisms such as *Mortierella* sp., *Mucor* sp., and *Cyanobacteria*. However, these GLA sources are not ideal for dietary supplementation due to large fluctuations in availability and costs associated with extraction processes.

SUMMARY OF THE INVENTION

The biosynthesis of fatty acids is a major activity of plants and microorganisms. However, humans have a limited capacity for synthesizing essential fatty acids, e.g., long chain polyunsaturated fatty acids (LCPUFAs). Biotechnology has long been considered an efficient way to manipulate the process of producing fatty acids in plants and microorganisms. It is cost-effective and renewable with little side effects. Thus, tremendous industrial effort directed to the production of various compounds including speciality fatty acids and pharmaceutical polypeptides through the manipulation of plant, animal, and microorganismal cells has ensued. Accordingly, biotechnology is an attractive route for producing unsaturated fatty acids, especially LCPUFAs, in a safe, cost-efficient manner so as to garner the maximum therapeutic value from these fatty acids.

The present invention is based, at least in part, on the discovery of a family of nucleic acid molecules encoding novel desaturases. In particular, the present inventors have identified the Fad 4 (Δ4 desaturase), Fad5 and Fad5-2 (Δ5 desaturase), and Fad6 (Δ6 desaturase) which are involved in the biosynthesis of long chain polyunsaturated fatty acids DHA (docosahexaenoic acid, 22:6, n-3) and DPA (docosapentaenoic acid, 22:5, n-6); more specifically, Fad4 desaturases 22:5 (n-3) and 22:4 (n-6) resulting in DHA and DPA; Fad5 and Fad5-2 desaturases 20:4 (n-3) and 20:3(n-6) resulting in EPA and AA; and Fad6 desaturases 18:2 (n-6) and 18:3(n-3) resulting in GLA (gamma-linolenic acid) and SDA (stearidonic acid).

In one embodiment, the invention features an isolated nucleic acid molecule that includes the nucleotide sequence set forth in SEQ ID NO:1, SEQ ID NO:3, SEQ ID NO:5, or SEQ ID NO:7. In another embodiment, the invention features an isolated nucleic acid molecule that encodes a polypeptide including the amino acid sequence set forth in SEQ ID NO:2, 4, 6, or 8.

In still other embodiments, the invention features isolated nucleic acid molecules including nucleotide sequences that are substantially identical (e.g., 70% identical) to the nucleotide sequence set forth as SEQ ID NO:1, SEQ ID NO:3, SEQ ID NO:5, or SEQ ID NO:7. The invention further features isolated nucleic acid molecules including at least 30 contiguous nucleotides of the nucleotide sequence set forth as SEQ ID NO:1, SEQ ID NO:3, SEQ ID NO:5, or SEQ ID NO:7. In another embodiment, the invention features isolated nucleic acid molecules which encode a polypeptide including an amino acid sequence that is substantially identical (e.g., 50% identical) to the amino acid sequence set forth as SEQ ID NO:2, 4, 6, or 8. Also featured are nucleic acid molecules which encode allelic variants of the polypeptide having the amino acid sequence set forth as SEQ ID NO: 2, 4, 6, or 8. In addition to isolated nucleic acid molecules encoding full-length polypeptides, the present invention also features nucleic acid molecules which encode fragments, for example, biologically active fragments, of the full-length polypeptides of the present invention (e.g., fragments including at least 10 contiguous amino acid residues of the amino acid sequence of SEQ ID NO: 2, 4, 6, or 8). In still other embodiments, the invention features nucleic acid molecules that are complementary to, or hybridize under stringent conditions to the isolated nucleic acid molecules described herein.

In a related aspect, the invention provides vectors including the isolated nucleic acid molecules described herein (e.g., desaturase-encoding nucleic acid molecules). Also featured are host cells including such vectors (e.g., host cells including vectors suitable for producing desaturase nucleic acid molecules and polypeptides).

In another aspect, the invention features isolated desaturase polypeptides and/or biologically active fragments thereof. Exemplary embodiments feature a polypeptide including the amino acid sequence set forth as SEQ ID NO: 2, 4, 6, or 8, a polypeptide including an amino acid sequence at least 50% identical to the amino acid sequence set forth as SEQ ID NO: 2, 4, 6, or 8, a polypeptide encoded by a nucleic acid molecule including a nucleotide sequence at least 70% identical to the nucleotide sequence set forth as SEQ ID NO:1, SEQ ID NO:3, SEQ ID NO:5, or SEQ ID NO:7. Also featured are fragments of the full-length polypeptides described herein (e.g., fragments including at least 10 contiguous amino acid residues of the sequence set forth as SEQ ID NO: 2, 4, 6, or 8) as well as allelic variants of the polypeptide having the amino acid sequence set forth as SEQ ID NO: 2, 4, 6, or 8.

In one embodiment, a desaturase polypeptide or fragment thereof has a desaturase activity. In another embodiment, a desaturase polypeptide, or fragment thereof, has an N-terminal heme-binding motif, e.g., a cytochrome b5-like domain found in front-end desaturases. In another embodiment, a desaturase polypeptide, or fragment thereof, has at least two, preferably about three, conservative histidine motifs found in all microsomal desaturases and, optionally, has a desaturase activity. In a preferred embodiment, the desaturase polypeptide, or fragment thereof, has about three histidine motifs.

The constructs containing the desaturase genes can be used in any expression system including plants, animals, and microorganisms for the production of cells capable of producing LCPUFAs such as DHA, EPA, AA, SDA, and GLA. Examples of plants used for expressing the desaturases of the present invention include, among others, plants and plant seeds from oilseed crops, e.g., flax (*Linum* sp.), rapeseed (*Brassica* sp.), soybean (*Glycine* and *Soja* sp.), sunflower (*Helianthus* sp.), corron (*Gossypium* sp.), corn (*Zea mays*), olive (*Olea* sp.), safflower (*Carthamus* sp.), cocoa (*Theobroma cacoa*), and peanut (*Arachis* sp.).

In a related aspect, the present invention provides new and improved methods of producing unsaturated fatty acids, e.g., LCPUFAs, and other key compounds of the unsaturated fatty acid biosynthetic pathway using cells, e.g., plant cells, animal cells, and/or microbial cells in which the unsaturated fatty acid biosynthetic pathway has been manipulated such that LCPUFAs or other desired unsaturated fatty acid compounds are produced.

The new and improved methodologies of the present invention include methods of producing unsaturated fatty acids (e.g., DHA) in cells having at least one fatty acid desaturase of the unsaturated fatty acid biosynthetic pathway manipulated such that unsaturated fatty acids are produced (e.g., produced at an increased level). For example, the invention features methods of producing an unsaturated fatty acid (e.g., DHA) in cells comprising at least one isolated desaturase nucleic acid molecule, e.g., Fad4, Fad5, Fad5-2, and/or Fad6, or a portion thereof, as described above, such that an unsaturated fatty acid, e.g., LCPUFA, e.g., DHA, is produced. Such methods can further comprise the step of recovering the LCPUFA.

In another embodiment, the present invention provides methods of producing unsaturated fatty acids, e.g., LCPUFAs, e.g., DHA, comprising contacting a composition comprising at least one desaturase target molecule, as defined herein, with at least one isolated desaturase polypeptide, e.g., Fad4, Fad5, Fad5-2, and/or Fad6, or a portion thereof, as described above, under conditions such that an unsaturated fatty acid, e.g., LCPUFA, e.g., DHA, is produced. Such methods can further comprise the step of recovering the LCPUFA.

The nucleic acids, proteins, and vectors described above are particularly useful in the methodologies of the present invention. In particular, the invention features methods of enhancing unsaturated fatty acid production (e.g., DHA production) that include culturing a recombinant plant, animal, and/or microorganism comprising a desaturase nucleic acid, e.g., Fad4, Fad5, Fad5-2, and/or Fad6, under conditions such that fatty acid production is enhanced.

In another embodiment, the present invention features methods of producing a cell capable of producing unsaturated fatty acids. Such methods include introducing into a cell, e.g., a plant cell, an isolated nucleic acid molecule which encodes a protein having an activity of catalyzing the formation of a double bond in a fatty acid molecule.

In another embodiment, the present invention features methods for modulating the production of fatty acids comprising culturing a cell comprising an isolated nucleic acid molecule which encodes a polypeptide having an activity of catalyzing the formation of a double bond, such that modulation of fatty acid production occurs.

In another embodiment, the present invention includes compositions which comprise the unsaturated fatty acids nucleic acids or polypeptides described herein. Compositions of the present invention can also comprise the cells capable of producing such fatty acids, as described above, and, optionally, a pharmaceutically acceptable carrier.

In another embodiment, the compositions of the present invention are used as a dietary supplement, e.g., in animal feed or as a neutraceutical. The compositions of the present invention are also used to treat a patient having a disorder, comprising administering the composition such that the patient is treated. Disorders encompassed by such methods include, for example, stress, diabetes, cancer, inflammatory disorders, and cardiovascular disorders.

Other features and advantages of the invention will be apparent from the following detailed description and claims.

BRIEF DESCRIPTION OF THE DRAWINGS

FIG. 1 shows the DNA and protein sequence of Fad4 from *Thraustochytrium* sp.; (A) the cDNA sequence of the open reading frame (SEQ ID NO:1); and (B) the translated protein sequence (SEQ ID NO:2).

FIG. 2 shows the DNA and protein sequence of Fad5 from *Thraustochytrium* sp.; (A) the cDNA sequence of the open reading frame (SEQ ID NO:3); and (B) the translated protein sequence (SEQ ID NO:4).

FIG. 3 shows a comparison of Fad4 and Fad5 protein sequences from *Thraustochytrium* sp. (SEQ ID NO:2 and 4, respectively). The vertical bar indicates amino acid identity. The conserved motifs such as the cytochrome b5 heme-binding and the histidine-rich motifs are highlighted. The two arrows indicate the binding locations of the two degenerate primers.

FIG. 4 shows the DNA and protein sequence of Fad5-2 from *Pythium irregulare*; (A) the cDNA sequence of the open reading frame (SEQ ID NO:5); and (B) the translated protein sequence (SEQ ID NO:6).

FIG. 5 shows the DNA and protein sequence of Fad6 of *Pythium irregulare*; (A) the cDNA sequence of the open reading frame (SEQ ID NO:7); and (B) the translated protein sequence (SEQ ID NO:8).

FIG. 6 shows a comparison of Fad5-2 and Fad6 protein sequences from *Pythium irregulare* (SEQ ID NO: 6 and 8, respectively). The vertical bar indicates amino acid identity. The conserved motifs such as the cytochrome b5 heme-binding and the histidine-rich motifs are highlighted. The two arrows indicate the binding locations of the two degenerate primers.

FIG. 23 is a table showing the fatty acid profile of *Thraustochytrium* sp.

FIG. 24 is a table showing the fatty acid profile of *Pythium irregulare*.

FIG. 25 is a table showing the conversion of exogenous fatty acids in yeast AMY-2α/pFad5-2.

FIG. 26 is a table showing the accumulation of Δ5-unsaturated polymethylene-interrupted fatty acids (A5-UPIFAs) in transgenic flaxseeds expressing Fad5-2 under the control of napin (Napin) and flax seed-specific (Cln) promoters. The fatty acid levels are shown as the weight percentage of the total fatty acids.

FIG. 27 is a table showing the accumulation of Δ6 desaturated fatty acids in transgenic flaxseeds (Solin and Normandy) expressing Fad6 under the control of the napin promoter. The fatty acid levels are shown as the weight percentage of the total fatty acids.

DETAILED DESCRIPTION OF THE INVENTION

Figure 7:
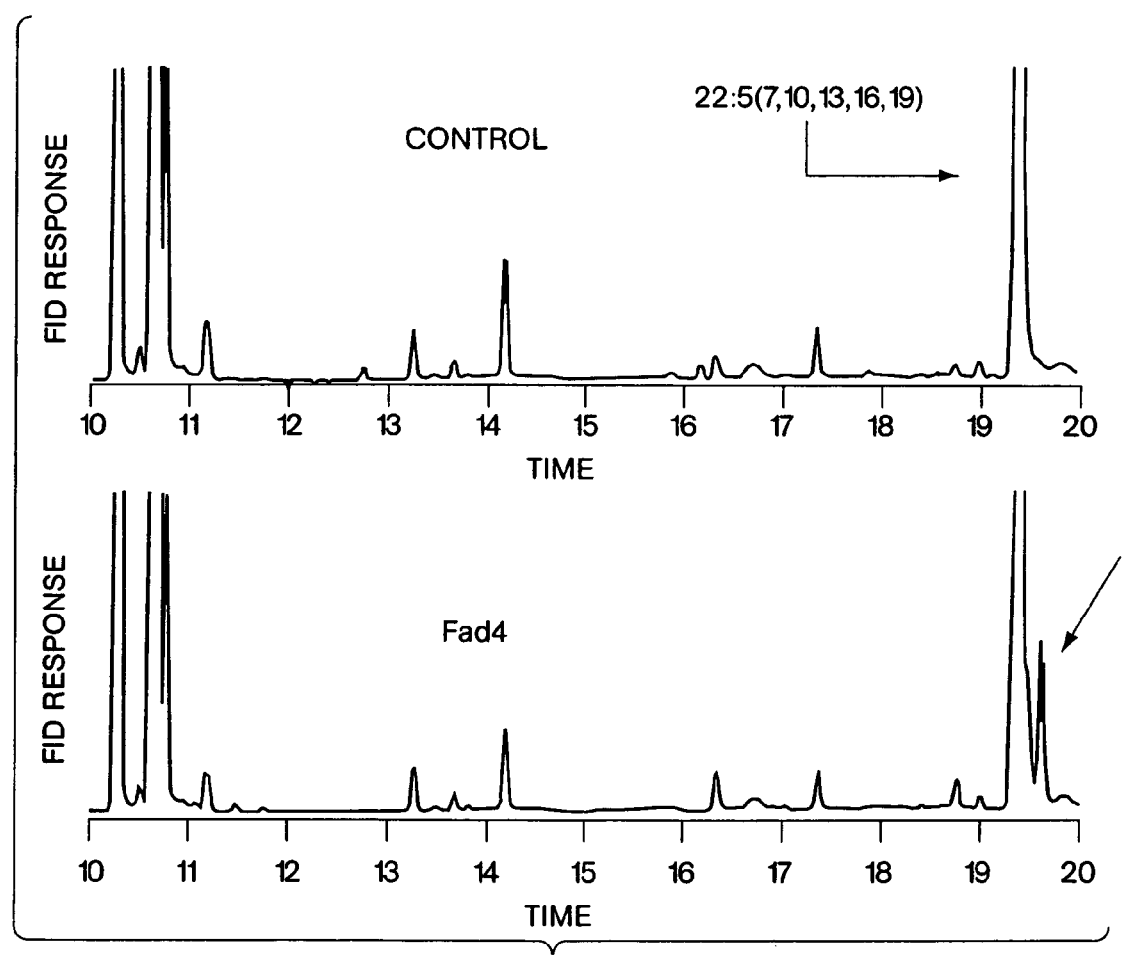
FIG. 7 is a gas chromatographic (GC) analysis of fatty acid methyl esters (FAMEs) from yeast strain Invsc2 expressing Fad4 with exogenous substrate 22:5 (n-3).

The present invention is based, at least in part, on the discovery of novel fatty acid desaturase family members, referred to interchangeably herein as "desaturases" or "desaturase" nucleic acid and protein molecules (e.g., Fad4, Fad5, Fad5-2, and Fad6). These novel molecules are members of the fatty acid desaturase family and are expressed in LCPUFAs-producing organisms, e.g., *Thraustochytrium, Pythium irregulare, Schizichytrium*, and *Crythecodinium*.

As used herein, the term "fatty acids" is art recognized and includes a long-chain hydrocarbon based carboxylic acid. Fatty acids are components of many lipids including glycerides. The most common naturally occurring fatty acids are monocarboxylic acids which have an even number of carbon atoms (16 or 18) and which may be saturated or unsaturated. "Unsaturated" fatty acids contain cis double bonds between the carbon atoms. Unsaturated fatty acids encompassed by the present invention include, for example, DHA, GLA, and SDA. "Polyunsaturated" fatty acids contain more than one double bond and the double bonds are arranged in a methylene interrupted system (—CH=CH—CH$_2$—CH=CH—).

Fatty acids are described herein by a numbering system in which the number before the colon indicates the number of carbon atoms in the fatty acid, whereas the number after the colon is the number of double bonds that are present. In the case of unsaturated fatty acids, this is followed by a number in parentheses that indicates the position of the double bonds. Each number in parenthesis is the lower numbered carbon atom of the two connected by the double bond. For example, oleic acid can be described as 18:1(9) and linoleic acid can be described as 18:2(9, 12) indicating 18 carbons, one double bond at carbon 9, two double bonds at carbons 9 and 12, respectively.

The controlling steps in the production of unsaturated fatty acids, i.e., the unsaturated fatty acid biosynthetic pathway, are catalyzed by membrane-associated fatty acid desaturases, e.g., Fad4, Fad5, Fad5-2, and/or Fad6. Specifically, such enzymes catalyze the formation of double bonds between the carbon atoms of a fatty acid molecule. As used herein, the term "unsaturated fatty acid biosynthetic pathway" refers to a series of chemical reactions leading to the synthesis of an unsaturated fatty acid either in vivo or in vitro. Such a pathway includes a series of desaturation and elongation steps which generate unsaturated fatty acids and ultimately, long chain polyunsaturated fatty acids. Such unsaturated fatty acids can include, GLA 18:3 (6,9,12), SDA 18:4 (6,9,12,15), AA 20:4 (5,8,11,14), EPA 20:5 (5,8,11,14,17), and DPA 22:5 (4,7,10,13,16), and DHA 22:6 (4,7,10,13,16,19).

Desaturases can contain a heme-binding motif and/or about three conservative histidine motifs, although additional domains may be present. Members of the fatty acid desaturase family convert saturated fatty acids to unsaturated fatty acids, e.g., long chain polyunsaturated fatty acids (LCPUFAs), which are components of cell membranes of various tissues and organelles in mammals (nerve, retina, brain and immune cells). Examples of LCPUFA include, among others, docosahexaenoic acid (DHA, 22:6(4,7,10,13,16,19)). Clinical studies have shown that DHA is essential for the growth and development of the brain in infants, and for maintenance of normal brain function in adults (Martinetz, M. (1992) J. Pediatr. 120:S129-S138). DHA also has effects on photoreceptor function involved in the signal transduction process, rhodopsin activation, and rod and cone development (Giusto, N. M., et al. (2000) Prog. Lipid Res. 39:315-391). In addition, positive effects of DHA were also found in the treatment of diseases such as hypertension, arthritis, atherosclerosis, depression, thrombosis and cancers (Horrocks, L. A. and Yeo, Y. K. (1999) Pharmacol. Res. 40:211-215). Thus, the desaturase molecules can be used to produce the LCPUFAs useful in treating disorders characterized by aberrantly regulated growth, proliferation, or differentiation. Such disorders include cancer, e.g., carcinoma, sarcoma, or leukemia; tumor angiogenesis and metastasis; skeletal dysplasia; hepatic disorders; myelodysplastic syndromes; and hematopoietic and/or myeloproliferative disorders. Other disorders related to angiogenesis and which are, therefore, desaturase associated disorders include hereditary hemorrhagic telangiectasia type 1, fibrodysplasia ossificans progressive, idiopathic pulmonary fibrosis, and Klippel-Trenaunay-Weber syndrome.

The term "family" when referring to the protein and nucleic acid molecules of the present invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin or alternatively, can contain homologues of non-human origin, e.g., rat or mouse proteins. Members of a family can also have common functional characteristics.

For example, the family of desaturase proteins of the present invention comprises one cytochrome b5 heme-binding motif. As used herein, the term "heme-binding motif" is an N-terminal extension of the cytochrome b5-like domain found in front-end desaturases.

In another embodiment, members of the desaturase family of proteins include a "histidine motifs" in the protein, preferably, about three or four histidine motifs. As used herein, the term "histidine motif" includes a protein domain having at least about two histidine amino acid residues, preferably about three or four histidine amino acid residues, and is typically found in all microsomal desaturases as the third conservative histidine motif.

Examples of cytochrome b5 heme-binding motifs and histidine motifs include amino acid residues 41-44, 182-186, 216-223, and 453-462 of SEQ ID NO:2, amino acid residues 40-43, 171-175, 207-213, and 375-384 of SEQ ID NO:4, amino acid residues 40-45, 171-176, 208-213, and 395-400 of SEQ ID NO:6, and amino acid residues 42-47, 178-183, 215-220, and 400-405 of SEQ ID NO:8, as shown in FIGS. 3 and 6.

Isolated desaturase proteins of the present invention have an amino acid sequence sufficiently homologous to the amino acid sequence of SEQ ID NO:2, 4, 6, or 8 or are encoded by a nucleotide sequence sufficiently homologous to SEQ ID NO:1, 3, 5 or 7. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains having at least 50%, 55%, 60%, 65%, 70%, 75%, 80%, 85%, 85%, 90%, 95%, 96%, 97%, 98%, 99% or more homology or identity across the amino acid sequences of the domains and contain at least one and preferably two structural domains or motifs, are defined herein as sufficiently homologous. Furthermore, amino acid or nucleotide sequences which share at least 50%, 55%, 60%, 65%, 70%, 75%, 80%, 85%, 85%, 90%, 95%, 96%, 97%, 98%, 99% or more homology or identity and share a common functional activity are defined herein as sufficiently homologous.

In a preferred embodiment, a desaturase protein includes at least one or more of the following domains or motifs: a heme-binding motif and/or a histidine motif and has an amino acid sequence at least about 50%, 55%, 60%, 65%, 70%, 75%, 80%, 85%, 85%, 90%, 95%, 96%, 97%, 98%, 99% or more homologous or identical to the amino acid sequence of SEQ ID NO:2, 4, 6, or 8. In yet another preferred embodiment, a desaturase protein includes at least one or more of the following domains: a heme-binding motif and/or a histidine motif, and is encoded by a nucleic acid molecule having a nucleotide sequence which hybridizes under stringent hybridization conditions to a complement of a nucleic acid molecule comprising the nucleotide sequence of SEQ ID NO:1, 3, 5, or 7. In another preferred embodiment, a desaturase protein includes at least one heme-binding motif and/or at least about three histidine motifs, and has a desaturase activity.

As used interchangeably herein, a "desaturase activity," "biological activity of a desaturase," or "functional activity of a desaturase," includes an activity exerted or mediated by a desaturase protein, polypeptide or nucleic acid molecule on a desaturase responsive cell or on a desaturase substrate, as determined in vivo or in vitro, according to standard techniques. In one embodiment, a desaturase activity is a direct activity such as an association with a desaturase target molecule. As used herein, a "target molecule" or "binding partner" is a molecule e.g., a molecule involved in the synthesis of unsaturated fatty acids, e.g., an intermediate fatty acid, with which a desaturase protein binds or interacts in nature such that a desaturase-mediated function is achieved. A desaturase direct activity also includes the formation of a double bond between the carbon atoms of a fatty acid molecule to form an unsaturated fatty acid molecule.

The nucleotide sequence of the isolated *Thraustochytrium* sp. A4 desaturase, Fad4, cDNA and the predicted amino acid sequence encoded by the Fad4 cDNA are shown in FIG. 1 and in SEQ ID NOs:1 and 2, respectively. The *Thraustochytrium* sp. Fad4 gene (the open reading frame), which is approximately 1560 nucleotides in length, encodes a protein having a molecular weight of approximately 59.1 kD and which is approximately 519 amino acid residues in length.

The nucleotide sequence of the *Thraustochytrium* sp. A5 desaturase, Fad5, cDNA and the predicted amino acid sequence encoded by the Fad5 cDNA are shown in FIG. 2 and in SEQ ID NOs:3 and 4, respectively. The *Thraustochytrium* sp. Fad5 gene, which is approximately 1320 nucleotides in length, encodes a protein having a molecular weight of approximately 49.8 kD and which is approximately 439 amino acid residues in length.

The nucleotide sequence of the *Pythium irregulare* A5 desaturase, Fad5-2, cDNA and the predicted amino acid sequence encoded by the Fad5-2 cDNA are shown in FIG. 4 and in SEQ ID NOs:5 and 6, respectively. The *Pythium irregulare* Fad5-2 gene, which is approximately 1371 nucleotides in length, encodes a protein having approximately 456 amino acid residues in length.

The nucleotide sequence of the *Pythium irregulare* A6 desaturase, Fad6, cDNA and the predicted amino acid sequence encoded by the Fad6 cDNA are shown in FIG. 5 and in SEQ ID NOs:7 and 8, respectively. The *Pythium irregulare* Fad6 gene, which is approximately 1383 nucleotides in length, encodes a protein having approximately 460 amino acid residues in length.

Various aspects of the invention are described in further detail in the following subsections:

I. Isolated Nucleic Acid Molecules

One aspect of the invention pertains to isolated nucleic acid molecules that encode desaturase proteins or biologically active portions thereof, as well as nucleic acid fragments sufficient for use as hybridization probes to identify desaturase-encoding nucleic acid molecules (e.g., desaturase mRNA) and fragments for use as PCR primers for the amplification or mutation of desaturase nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated desaturase nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, 3, 5, 7, or a portion thereof, can be isolated using standard molecular biology techniques and the sequence information provided herein. Using all or a portion of the nucleic acid sequence of SEQ ID NO:1, 3, 5, or 7, as hybridization probes, desaturase nucleic acid molecules can be isolated using standard hybridization and cloning techniques (e.g., as described in Sambrook, J. et al. *Molecular Cloning: A Laboratory Manual*. $2^{nd}$, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1, 3, 5, or 7, can be isolated by the polymerase chain reaction (PCR) using synthetic oligonucleotide primers designed based upon the sequence of SEQ ID NO:1, 3, 5, or 7.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to desaturase nucleotide sequences can be prepared by standard synthetic techniques, e.g., using an automated DNA synthesizer.

In another embodiment, the nucleic acid molecule consists of the nucleotide sequence set forth as SEQ ID NO:1, 3, 5, or 7.

In still another embodiment, an isolated nucleic acid molecule of the invention comprises a nucleic acid molecule which is a complement of the nucleotide sequence shown in SEQ ID NO:1, 3, 5, or 7, or a portion of any of these nucleotide sequences. A nucleic acid molecule which is complementary to the nucleotide sequence shown in SEQ ID NO:1, 3, 5, or 7 is one which is sufficiently complementary to the nucleotide sequence shown in SEQ ID NO:1, 3, 5, or 7, such that it can hybridize to the nucleotide sequence shown in SEQ ID NO:1, 3, 5, or 7, thereby forming a stable duplex.

In still another embodiment, an isolated nucleic acid molecule of the present invention comprises a nucleotide sequence which is at least about 50%, 55%, 60%, 65%, 70%, 75%, 80%, 85%, 90%, 95%, 96%, 97%, 98%, 99% or more identical to the nucleotide sequence shown in SEQ ID NO:1, 3, 5, or 7 (e.g., to the entire length of the nucleotide sequence), or a portion or complement of any of these nucleotide sequences. In one embodiment, a nucleic acid molecule of the present invention comprises a nucleotide sequence which is at least (or no greater than) 50-100, 100-250, 250-500, 500-750, 750-1000, 1000-1250, 1250-1500, 1500-1750, 1750-2000, 2000-2250, 2250-2500, 2500-2750, 2750-3000, 3250-3500, 3500-3750 or more nucleotides in length and hybridizes under stringent hybridization conditions to a complement of a nucleic acid molecule of SEQ ID NO:1, 3, 5, or 7.

Moreover, the nucleic acid molecule of the invention can comprise only a portion of the nucleic acid sequence of SEQ ID NO:1, 3, 5, or 7, for example, a fragment which can be used as a probe or primer or a fragment encoding a portion of a desaturase protein, e.g., a biologically active portion of a desaturase protein. The nucleotide sequence determined from the cloning of the desaturase gene allows for the generation of probes and primers designed for use in identifying and/or cloning other desaturase family members, as well as desaturase homologues from other species. The probe/primer (e.g., oligonucleotide) typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1, 3, 5 or 7, of an anti-sense sequence of SEQ ID NO:1, 3, 5, or 7, or of a naturally occurring allelic variant or mutant of SEQ ID NO:1, 3, 5, or 7.

Exemplary probes or primers are at least (or no greater than) 12 or 15, 20 or 25, 30, 35, 40, 45, 50, 55, 60, 65, 70, 75 or more nucleotides in length and/or comprise consecutive nucleotides of an isolated nucleic acid molecule described herein. Also included within the scope of the present invention are probes or primers comprising contiguous or consecutive nucleotides of an isolated nucleic acid molecule described herein, but for the difference of 1, 2, 3, 4, 5, 6, 7, 8, 9 or 10 bases within the probe or primer sequence. Probes based on the desaturase nucleotide sequences can be used to detect (e.g., specifically detect) transcripts or genomic sequences encoding the same or homologous proteins. In preferred embodiments, the probe further comprises a label group attached thereto, e.g., the label group can be a radio-isotope, a fluorescent compound, an enzyme, or an enzyme co-factor. In another embodiment a set of primers is provided, e.g., primers suitable for use in a PCR, which can be used to amplify a selected region of a desaturase sequence, e.g., a domain, region, site or other sequence described herein. The primers should be at least 5, 10, or 50 base pairs in length and less than 100, or less than 200, base pairs in length. The primers should be identical, or differ by no greater than 1, 2, 3, 4, 5, 6, 7, 8, 9 or 10 bases when compared to a sequence disclosed herein or to the sequence of a naturally occurring variant. Such probes can be used as a part of a diagnostic test kit for identifying cells or tissue which misexpress a desaturase protein, such as by measuring a level of a desaturase-encoding nucleic acid in a sample of cells from a subject, e.g., detecting desaturase mRNA levels or determining whether a genomic desaturase gene has been mutated or deleted.

A nucleic acid fragment encoding a "biologically active portion of a desaturase protein" can be prepared by isolating a portion of the nucleotide sequence of SEQ ID NO: 1, 3, 5, or 7, which encodes a polypeptide having a desaturase biological activity (the biological activities of the desaturase proteins are described herein), expressing the encoded portion of the desaturase protein (e.g., by recombinant expression in vitro) and assessing the activity of the encoded portion of the desaturase protein. In an exemplary embodiment, the nucleic acid molecule is at least 50-100, 100-250, 250-500, 500-700, 750-1000, 1000-1250, 1250-1500, 1500-1750, 1750-2000, 2000-2250, 2250-2500, 2500-2750, 2750-3000, 3250-3500, 3500-3750 or more nucleotides in length and encodes a protein having a desaturase activity (as described herein).

The invention further encompasses nucleic acid molecules that differ from the nucleotide sequence shown in SEQ ID NO: 1, 3, 5, or 7 due to degeneracy of the genetic code and thus encode the same desaturase proteins as those encoded by the nucleotide sequence shown in SEQ ID NO: 1, 3, 5, or 7. In another embodiment, an isolated nucleic acid molecule of the invention has a nucleotide sequence encoding a protein having an amino acid sequence which differs by at least 1, but no greater than 5, 10, 20, 50 or 100 amino acid residues from the amino acid sequence shown in SEQ ID NO:2, 4, 6, or 8. In yet another embodiment, the nucleic acid molecule encodes the amino acid sequence of human desaturase. If an alignment is needed for this comparison, the sequences should be aligned for maximum homology.

Nucleic acid variants can be naturally occurring, such as allelic variants (same locus), homologues (different locus), and orthologues (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

Allelic variants result, for example, from DNA sequence polymorphisms within a population (e.g., the human population) that lead to changes in the amino acid sequences of the desaturase proteins. Such genetic polymorphism in the desaturase genes may exist among individuals within a population due to natural allelic variation.

As used herein, the terms "gene" and "recombinant gene" refer to nucleic acid molecules which include an open reading frame encoding a desaturase protein, e.g., oilseed desaturase protein, and can further include non-coding regulatory sequences, and introns.

Accordingly, in one embodiment, the invention features isolated nucleic acid molecules which encode a naturally occurring allelic variant of a polypeptide comprising the amino acid sequence of SEQ ID NO:2, 4, 6, or 8, wherein the nucleic acid molecule hybridizes to a complement of a nucleic acid molecule comprising SEQ ID NO: 1, 3, 5, or 7, for example, under stringent hybridization conditions.

Allelic variants of desaturase, e.g., Fad4, Fad5, Fad5-2, or Fad6, include both functional and non-functional desaturase proteins. Functional allelic variants are naturally occurring amino acid sequence variants of the desaturase protein that maintain the ability to, e.g., (i) interact with a desaturase substrate or target molecule (e.g., a fatty acid, e.g., 22:5(n-3)); and/or (ii) form a double bond between carbon atoms in a desaturase substrate or target molecule. The fatty acids produced by the nucleic acid and protein molecules of the present invention are also useful in treating disorders such as aging, stress, diabetes, cancer, inflammatory disorders (e.g., arthritis, eczema), and cardiovascular disorders. Functional allelic variants will typically contain only a conservative substitution of one or more amino acids of SEQ ID NO:2, 4, 6, or 8, or a substitution, deletion or insertion of non-critical residues in non-critical regions of the protein.

Non-functional allelic variants are naturally occurring amino acid sequence variants of the desaturase protein, e.g., Fad4, Fad5, Fad5-2, or Fad6, that do not have the ability to, e.g., (i) interact with a desaturase substrate or target molecule (e.g., an intermediate fatty acid, such as 18:4(6,9,12,15)); and/or (ii) form a double bond between carbon atoms in a desaturase substrate or target molecule. Non-functional allelic variants will typically contain a non-conservative substitution, a deletion, or insertion, or premature truncation of the amino acid sequence of SEQ ID NO: 2, 4, 6, or 8, or a substitution, insertion, or deletion in critical residues or critical regions of the protein.

The present invention further provides orthologues (e.g., human orthologues of the desaturase proteins). Orthologues of the *Thraustochytrium* sp. and *Pythium irregulare* desaturase proteins are proteins that are isolated from other organisms and possess the same desaturase substrate or target molecule binding mechanisms, double bond forming mechanisms, modulating mechanisms of growth and development of the brain in infants, maintenance mechanisms of normal brain function in adults, ability to affect photoreceptor function involved in the signal transduction process, ability to affect rhodopsin activation, development mechanisms of rods and/or cones, and/or modulating mechanisms of cellular growth and/or proliferation of the non-human desaturase proteins. Orthologues of the *Thraustochytrium* sp. and *Pythium irregulare* desaturase proteins can readily be identified as comprising an amino acid sequence that is substantially homologous to SEQ ID NO:2, 4, 6, or 8.

Moreover, nucleic acid molecules encoding other desaturase family members and, thus, which have a nucleotide sequence which differs from the desaturase sequences of SEQ ID NO: 1, 3, 5, or 7 are intended to be within the scope of the invention. For example, another desaturase cDNA can be identified based on the nucleotide sequence of Fad4, Fad5, Fad5-2, or Fad6. Moreover, nucleic acid molecules encoding desaturase proteins from different species, and which, thus, have a nucleotide sequence which differs from the desaturase sequences of SEQ ID NO: 1, 3, 5, or 7 are intended to be within the scope of the invention. For example, *Schizochytrium* or *Crythecodinium* desaturase cDNA can be identified based on the nucleotide sequence of a Fad4, Fad5, Fad5-2, or Fad6.

Nucleic acid molecules corresponding to natural allelic variants and homologues of the desaturase cDNAs of the invention can be isolated based on their homology to the desaturase nucleic acids disclosed herein using the cDNAs disclosed herein, or a portion thereof, as a hybridization probe according to standard hybridization techniques under stringent hybridization conditions.

Orthologues, homologues and allelic variants can be identified using methods known in the art (e.g., by hybridization to an isolated nucleic acid molecule of the present invention, for example, under stringent hybridization conditions). In one embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1, 3, 5, or 7. In other embodiment, the nucleic acid is at least 50-100, 100-250, 250-500, 500-700, 750-1000, 1000-1250, 1250-1500, 1500-1750, 1750-2000, 2000-2250, 2250-2500, 2500-2750, 2750-3000, 3250-3500, 3500-3750 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4, and 6. Additional stringent conditions can be found in *Molecular Cloning: A Laboratory Manual*, Sambrook et al., Cold Spring Harbor Press, Cold Spring Harbor, N.Y. (1989), chapters 7, 9, and 11. A preferred, non-limiting example of stringent hybridization conditions includes hybridization in 4× sodium chloride/sodium citrate (SSC), at about 65-70° C. (or alternatively hybridization in 4× SSC plus 50% formamide at about 42-50° C.) followed by one or more washes in 1× SSC, at about 65-70° C. A preferred, non-limiting example of highly stringent hybridization conditions includes hybridization in 1× SSC, at about 65-70° C. (or alternatively hybridization in 1× SSC plus 50% formamide at about 42-50° C.) followed by one or more washes in 0.3× SSC, at about 65-70° C. A preferred, non-limiting example of reduced stringency hybridization conditions includes hybridization in 4× SSC, at about 50-60° C. (or alternatively hybridization in 6× SSC plus 50% formamide at about 40-45° C.) followed by one or more washes in 2× SSC, at about 50-60° C. Ranges intermediate to the above-recited values, e.g., at 65-70° C. or at 42-50° C. are also intended to be encompassed by the present invention. SSPE (1× SSPE is 0.15M NaCl, 10 mM $NaH_2PO_4$, and 1.25 mM EDTA, pH 7.4) can be substituted for SSC (1× SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m(°\,C.) = 2(\text{\# of A+T bases}) + 4(\text{\# of G+C bases})$. For hybrids between 18 and 49 base pairs in length, $T_m(°\,C.) = 81.5 + 16.6(\log_{10}[Na^+]) + 0.41(\%\ G+C) - (600/N)$, where N is the number of bases in the hybrid, and $[Na^+]$ is the concentration of sodium ions in the hybridization buffer ($[Na^+]$ for 1× SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M $NaH_2PO_4$, 7% SDS at about 65° C., followed by one or more washes at 0.02M $NaH_2PO_4$, 1% SDS at 65° C. (see e.g., Church and Gilbert (1984) *Proc. Natl. Acad. Sci. USA* 81:1991-1995), or alternatively 0.2× SSC, 1% SDS.

Preferably, an isolated nucleic acid molecule of the invention that hybridizes under stringent conditions to the sequence of SEQ ID NO:1, 3, 5, or 7 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the desaturase sequences that may exist in the population, the skilled artisan will further appreciate that changes can be introduced by mutation into the nucleotide sequences of SEQ ID NO: 1, 3, 5, or 7, thereby leading to changes in the amino acid sequence of the encoded desaturase proteins, without altering the functional ability of the desaturase proteins. For example, nucleotide substitutions leading to amino acid substitutions at "non-essential" amino acid residues can be made in the sequence of SEQ ID NO: 1, 3, 5, or 7. A "non-essential" amino acid residue is a residue that can be altered from the wild-type sequence of Fad4, Fad5, Fad5-2, or Fad6 (e.g., the sequence of SEQ ID NO:2, 4, 6, or 8) without altering the biological activity, whereas an "essential" amino acid residue is required for biological activity. For example, amino acid residues that are conserved among the desaturase proteins of the present invention, e.g., those present in a heme-binding motif or a histidine motif, are predicted to be particularly unamenable to alteration. Furthermore, additional amino acid residues that are conserved between the desaturase proteins of the present invention and other members of the fatty acid desaturase family are not likely to be amenable to alteration.

Accordingly, another aspect of the invention pertains to nucleic acid molecules encoding desaturase proteins that contain changes in amino acid residues that are not essential for activity. Such desaturase proteins differ in amino acid sequence from SEQ ID NO:2, 4, 6, or 8, yet retain biological activity. In one embodiment, the isolated nucleic acid molecule comprises a nucleotide sequence encoding a protein, wherein the protein comprises an amino acid sequence at least about 50%, 55%, 60%, 65%, 70%, 75%, 80%, 85%, 90%, 95%, 96%, 97%, 98% 99% or more homologous to SEQ ID NO: 2, 4, 6, or 8, e.g., to the entire length of SEQ ID NO:2, 5, 8, or 11.

An isolated nucleic acid molecule encoding a desaturase protein homologous to the protein of SEQ ID NO: 2, 4, 6, or 8 can be created by introducing one or more nucleotide substitutions, additions or deletions into the nucleotide sequence of SEQ ID NO:1, 3, 5, or 7, such that one or more amino acid substitutions, additions or deletions are introduced into the encoded protein. Mutations can be introduced into SEQ ID NO:1, 3, 5, or 7 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a desaturase protein is preferably replaced with another amino acid residue from the same side chain family. Alternatively, in another embodiment, mutations can be introduced randomly along all or part of a desaturase coding sequence, such as by saturation mutagenesis, and the resultant mutants can be screened for desaturase biological activity to identify mutants that retain activity. Following mutagenesis of SEQ ID NO:1, 3, 5, or 7, the encoded protein can be expressed recombinantly and the activity of the protein can be determined.

In a preferred embodiment, a mutant desaturase protein can be assayed for the ability to (i) interact with a desaturase substrate or target molecule (e.g., an intermediate fatty acid); and/or (ii) form a double bond between carbon atoms in a desaturase substrate or target molecule.

II. Isolated Desaturase Proteins

One aspect of the invention pertains to isolated or recombinant desaturase proteins and polypeptides, and biologically active portions thereof. In one embodiment, native desaturase proteins can be isolated from cells or tissue sources by an appropriate purification scheme using standard protein purification techniques. In another embodiment, desaturase proteins are produced by recombinant DNA techniques. Alternative to recombinant expression, a desaturase protein or polypeptide can be synthesized chemically using standard peptide synthesis techniques.

An "isolated" or "purified" protein or biologically active portion thereof is substantially free of cellular material or other contaminating proteins from the cell or tissue source from which the desaturase protein is derived, or substantially free from chemical precursors or other chemicals when chemically synthesized. The language "substantially free of cellular material" includes preparations of desaturase protein in which the protein is separated from cellular components of the cells from which it is isolated or recombinantly produced. In one embodiment, the language "substantially free of cellular material" includes preparations of desaturase protein having less than about 80%, 70%, 60%, 50%, 40%, or 30% (by dry weight) of non-desaturase protein (also referred to herein as a "contaminating protein"), more preferably less than about 20% of non-desaturase protein, still more preferably less than about 10% of non-desaturase protein, and most preferably less than about 5% non-desaturase protein. When the desaturase protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of desaturase protein in which the protein is separated from chemical precursors or other chemicals which are involved in the synthesis of the protein. In one embodiment, the language "substantially free of chemical precursors or other chemicals" includes preparations of desaturase protein having less than about 30% (by dry weight) of chemical precursors or non-desaturase chemicals, more preferably less than about 20% chemical precursors or non-desaturase chemicals, still more preferably less than about 10% chemical precursors or non-desaturase chemicals, and most preferably less than about 5% chemical precursors or non-desaturase chemicals. It should be understood that the proteins or this invention can also be in a form which is different than their corresponding naturally occurring proteins and/or which is still in association with at least some cellular components. For example, the protein can be associated with a cellular membrane.

As used herein, a "biologically active portion" of a desaturase protein includes a fragment of a desaturase protein which participates in an interaction between a desaturase molecule and a non-desaturase molecule (e.g., a desaturase substrate such as fatty acid). Biologically active portions of a desaturase protein include peptides comprising amino acid sequences sufficiently homologous to or derived from the desaturase amino acid sequences, e.g., the amino acid sequences shown in SEQ ID NO:2, 4, 6, or 8 which include sufficient amino acid residues to exhibit at least one activity of a desaturase protein. Typically, biologically active portions comprise a domain or motif with at least one activity of the desaturase protein; the ability to (i) interact with a desaturase substrate or target molecule (e.g., an intermediate fatty acid); and/or (ii) form a double bond between carbon atoms in a desaturase substrate or target molecule. A biologically active portion of a desaturase protein can be a polypeptide which is, for example, 10, 25, 50, 75, 100, 125, 150, 175, 200, 250, 300, 350, 400, 450, 500, 550, 600, 650, 700, 750, 800, 850, 900, 950, 1000, 1050, 1100, 1150, 1200 or more amino acids in length.

In one embodiment, a biologically active portion of a desaturase protein comprises a heme-binding motif and/or at least one histidine motifs, preferably about three histidine motifs. Moreover, other biologically active portions, in which other regions of the protein are deleted, can be prepared by recombinant techniques and evaluated for one or more of the functional activities of a native desaturase protein.

In a preferred embodiment, a desaturase protein has an amino acid sequence shown in SEQ ID NO: 2, 4, 6, or 8. In other embodiments, the desaturase protein is substantially identical to SEQ ID NO: 2, 4, 6, or 8 and retains the functional activity of the protein of SEQ ID NO: 2, 4, 6, or 8, yet differs in amino acid sequence due to natural allelic variation or mutagenesis, as described in detail in subsection I above. In another embodiment, the desaturase protein is a protein which comprises an amino acid sequence at least about 50%, 55%, 60%, 65%, 70%, 75%, 80%, 85%, 90%, 95%, 96%, 97%, 98%, 99% or more identical to SEQ ID NO: 2, 4, 6, or 8.

In another embodiment, the invention features a desaturase protein which is encoded by a nucleic acid molecule consisting of a nucleotide sequence at least about 50%, 55%, 60%, 65%, 70%, 75%, 80%, 85%, 90%, 95%, 96%, 97%, 98%, 99% or more identical to a nucleotide sequence of SEQ ID NO:1, 3, 5, or 7, or a complement thereof. This invention further features a desaturase protein which is encoded by a nucleic acid molecule consisting of a nucleotide sequence which hybridizes under stringent hybridization conditions to a complement of a nucleic acid molecule comprising the nucleotide sequence of SEQ ID NO:1, 3, 5, or 7, or a complement thereof.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the Fad4 amino acid sequence of SEQ ID NO:2 having 519 amino acid residues, at least 156, preferably at least 208, more preferably at least 260, even more preferably at least 311, and even more preferably at least 363, 415, or 467 amino acid residues are aligned; when aligning a second sequence to the Fad5 amino acid sequence of SEQ ID NO:4 having 439 amino acid residues, at least 132, preferably at least 176, more preferably at least 220, even more preferably at least 263, and even more preferably at least 307, 351, or 395 amino acid residues are aligned; when aligning a second sequence to the Fad5-2 amino acid sequence of SEQ ID NO:6 having 456 amino acid residues, at least 137, preferably at least 182, more preferably at least 228, even more preferably at least 273, and even more preferably at least 319, 365, or 419 amino acid residues are aligned; when aligning a second sequence to the Fad6 amino acid sequence of SEQ ID NO:8 having 460 amino acid residues, at least 138, preferably at least 184, more preferably at least 230, even more preferably at least 276, and even more preferably at least 322, 368, or 414 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48): 444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A preferred, non-limiting example of parameters to be used in conjunction with the GAP program include a Blosum 62 scoring matrix with a gap penalty of 12, a gap extend penalty of 4, and a frameshift gap penalty of 5.

In another embodiment, the percent identity between two amino acid or nucleotide sequences is determined using the algorithm of Meyers and Miller (*Comput. Appl. Biosci.*, 4:11-17 (1988)) which has been incorporated into the ALIGN program (version 2.0 or version 2.0U), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul et al. (1990) *J. Mol. Biol.*

215:403-10. BLAST nucleotide searches can be performed with the NBLAST program, score=100, wordlength=12 to obtain nucleotide sequences homologous to desaturase nucleic acid molecules of the invention. BLAST protein searches can be performed with the XBLAST program, score=50, wordlength=3 to obtain amino acid sequences homologous to desaturase protein molecules of the invention. To obtain gapped alignments for comparison purposes, Gapped BLAST can be utilized as described in Altschul et al. (1997) *Nucleic Acids Res.* 25(17):3389-3402. When utilizing BLAST and Gapped BLAST programs, the default parameters of the respective programs (e.g., XBLAST and NBLAST) can be used.

III. Methods of Producing Unsaturated Fatty Acids

The present invention provides new and improved methods of producing unsaturated fatty acids, e.g., LCPUFAs, such as, DHA (docosahexaenoic acid, 22:6 (n-6)), DPA (docosapentaenoic acid, 22:5 (n-6)), AA (Arachidonic acid, 20:4 (n-6)) and EPA (eicosapentaenioc acid, 20:5(n-3)).

A. Recombinant Cells and Methods for Culturing Cells

The present invention further features recombinant vectors that include nucleic acid sequences that encode the gene products as described herein, preferably Fad4, Fad5, Fad5-2, and Fad6 gene products. The term recombinant vector includes a vector (e.g., plasmid) that has been altered, modified or engineered such that it contains greater, fewer or different nucleic acid sequences than those included in the native vector or plasmid. In one embodiment, a recombinant vector includes the nucleic acid sequence encoding at least one fatty acid desaturase enzyme operably linked to regulatory sequences. The phrase "operably linked to regulatory sequence(s)" means that the nucleotide sequence of interest is linked to the regulatory sequence(s) in a manner which allows for expression (e.g., enhanced, increased, constitutive, basal, attenuated, decreased or repressed expression) of the nucleotide sequence, preferably expression of a gene product encoded by the nucleotide sequence (e.g., when the recombinant vector is introduced into a cell). Exemplary vectors are described in further detail herein as well as in, for example, Frascotti et al., U.S. Pat. No. 5,721,137, the contents of which are incorporated herein by reference.

The term "regulatory sequence" includes nucleic acid sequences which affect (e.g., modulate or regulate) expression of other (non-regulatory) nucleic acid sequences. In one embodiment, a regulatory sequence is included in a recombinant vector in a similar or identical position and/or orientation relative to a particular gene of interest as is observed for the regulatory sequence and gene of interest as it appears in nature, e.g., in a native position and/or orientation. For example, a gene of interest (e.g., a Fad4, Fad5, Fad5-2, or Fad6 gene) can be included in a recombinant vector operably linked to a regulatory sequence which accompanies or is adjacent to the gene in the natural organism (e.g., operably linked to "native" Fad4, Fad5, Fad5-2, or Fad6 regulatory sequence (e.g., to the "native" Fad4, Fad5, Fad5-2, or Fad6 promoter). Alternatively, a gene of interest (e.g., a Fad4, Fad5, Fad5-2, or Fad6 gene) can be included in a recombinant vector operably linked to a regulatory sequence which accompanies or is adjacent to another (e.g., a different) gene in the natural organism. For example, a Fad4, Fad5, Fad5-2, or Fad6 gene can be included in a vector operably linked to non-Fad4, Fad5, Fad5-2, or Fad6 regulatory sequences. Alternatively, a gene of interest (e.g., a Fad4, Fad5, Fad5-2, or Fad6 gene) can be included in a vector operably linked to a regulatory sequence from another organism. For example, regulatory sequences from other microbes (e.g., other bacterial regulatory sequences, bacteriophage regulatory sequences and the like) can be operably linked to a particular gene of interest.

Preferred regulatory sequences include promoters, enhancers, termination signals and other expression control elements (e.g., binding sites for transcriptional and/or translational regulatory proteins, for example, in the transcribed mRNA). Such regulatory sequences are described, for example, in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989. Regulatory sequences include those which direct constitutive expression of a nucleotide sequence in a cell (e.g., constitutive promoters and strong constitutive promoters), those which direct inducible expression of a nucleotide sequence in a cell (e.g., inducible promoters, for example, xylose inducible promoters) and those which attenuate or repress expression of a nucleotide sequence in a cell (e.g., attenuation signals or repressor sequences). It is also within the scope of the present invention to regulate expression of a gene of interest by removing or deleting regulatory sequences. For example, sequences involved in the negative regulation of transcription can be removed such that expression of a gene of interest is enhanced.

In one embodiment, a recombinant vector of the present invention includes nucleic acid sequences that encode at least one gene product (e.g., Fad4, Fad5, Fad5-2, or Fad6) operably linked to a promoter or promoter sequence.

In yet another embodiment, a recombinant vector of the present invention includes a terminator sequence or terminator sequences (e.g., transcription terminator sequences). The term "terminator sequences" includes regulatory sequences which serve to terminate transcription of mRNA. Terminator sequences (or tandem transcription terminators) can further serve to stabilize mRNA (e.g., by adding structure to mRNA), for example, against nucleases.

In yet another embodiment, a recombinant vector of the present invention includes antibiotic resistance sequences. The term "antibiotic resistance sequences" includes sequences which promote or confer resistance to antibiotics on the host organism. In one embodiment, the antibiotic resistance sequences are selected from the group consisting of cat (chloramphenicol resistance), tet (tetracycline resistance) sequences, erm (erythromycin resistance) sequences, neo (neomycin resistance) sequences and spec (spectinomycin resistance) sequences. Recombinant vectors of the present invention can further include homologous recombination sequences (e.g., sequences designed to allow recombination of the gene of interest into the chromosome of the host organism). For example, amyE sequences can be used as homology targets for recombination into the host chromosome.

The term "manipulated cell" includes a cell that has been engineered (e.g., genetically engineered) or modified such that the cell has at least one fatty acid desaturase, e.g., Fad4, Fad5, Fad5-2, and/or Fad6, such that an unsaturated fatty acid is produced. Modification or engineering of such microorganisms can be according to any methodology described herein including, but not limited to, deregulation of a biosynthetic pathway and/or overexpression of at least one biosynthetic enzyme. A "manipulated" enzyme (e.g., a "manipulated" biosynthetic enzyme) includes an enzyme, the expression or production of which has been altered or modified such that at least one upstream or downstream precursor, substrate or product of the enzyme is altered or modified, for example, as compared to a corresponding wild-type or naturally occurring enzyme.

The term "overexpressed" or "overexpression" includes expression of a gene product (e.g., a fatty acid desaturase) at a level greater than that expressed prior to manipulation of the cell or in a comparable cell which has not been manipulated. In one embodiment, the cell can be genetically manipulated (e.g., genetically engineered) to overexpress a level of gene product greater than that expressed prior to manipulation of the cell or in a comparable cell which has not been manipulated. Genetic manipulation can include, but is not limited to, altering or modifying regulatory sequences or sites associated with expression of a particular gene (e.g., by adding strong promoters, inducible promoters or multiple promoters or by removing regulatory sequences such that expression is constitutive), modifying the chromosomal location of a particular gene, altering nucleic acid sequences adjacent to a particular gene such as a ribosome binding site or transcription terminator, increasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene routine in the art (including but not limited to use of antisense nucleic acid molecules, for example, to block expression of repressor proteins).

In another embodiment, the cell can be physically or environmentally manipulated to overexpress a level of gene product greater than that expressed prior to manipulation of the cell or in a comparable cell which has not been manipulated. For example, a cell can be treated with or cultured in the presence of an agent known or suspected to increase transcription of a particular gene and/or translation of a particular gene product such that transcription and/or translation are enhanced or increased. Alternatively, a cell can be cultured at a temperature selected to increase transcription of a particular gene and/or translation of a particular gene product such that transcription and/or translation are enhanced or increased.

The term "deregulated" or "deregulation" includes the alteration or modification of at least one gene in a cell that encodes an enzyme in a biosynthetic pathway, such that the level or activity of the biosynthetic enzyme in the cell is altered or modified. Preferably, at least one gene that encodes an enzyme in a biosynthetic pathway is altered or modified such that the gene product is enhanced or increased. The phrase "deregulated pathway" can also include a biosynthetic pathway in which more than one gene that encodes an enzyme in a biosynthetic pathway is altered or modified such that the level or activity of more than one biosynthetic enzyme is altered or modified. The ability to "deregulate" a pathway (e.g., to simultaneously deregulate more than one gene in a given biosynthetic pathway) in a cell arises from the particular phenomenon of cells in which more than one enzyme (e.g., two or three biosynthetic enzymes) are encoded by genes occurring adjacent to one another on a contiguous piece of genetic material termed an "operon".

The term "operon" includes a coordinated unit of gene expression that contains a promoter and possibly a regulatory element associated with one or more, preferably at least two, structural genes (e.g., genes encoding enzymes, for example, biosynthetic enzymes). Expression of the structural genes can be coordinately regulated, for example, by regulatory proteins binding to the regulatory element or by anti-termination of transcription. The structural genes can be transcribed to give a single mRNA that encodes all of the structural proteins. Due to the coordinated regulation of genes included in an operon, alteration or modification of the single promoter and/or regulatory element can result in alteration or modification of each gene product encoded by the operon. Alteration or modification of the regulatory element can include, but is not limited to removing the endogenous promoter and/or regulatory element(s), adding strong promoters, inducible promoters or multiple promoters or removing regulatory sequences such that expression of the gene products is modified, modifying the chromosomal location of the operon, altering nucleic acid sequences adjacent to the operon or within the operon such as a ribosome binding site, increasing the copy number of the operon, modifying proteins (e.g., regulatory proteins, suppressors, enhancers, transcriptional activators and the like) involved in transcription of the operon and/or translation of the gene products of the operon, or any other conventional means of deregulating expression of genes routine in the art (including but not limited to use of antisense nucleic acid molecules, for example, to block expression of repressor proteins). Deregulation can also involve altering the coding region of one or more genes to yield, for example, an enzyme that is feedback resistant or has a higher or lower specific activity.

A particularly preferred "recombinant" cell of the present invention has been genetically engineered to overexpress a plant-derived gene or gene product or an microorganismally-derived gene or gene product. The term "plant-derived," "microorganismally-derived," or "derived-from," for example, includes a gene which is naturally found in a microorganism or a plant, e.g., an oilseed plant, or a gene product (e.g., Fad4, Fad5, Fad5-2, or Fad6) or which is encoded by a plant gene or a gene from a microorganism (e.g., encoded SEQ ID NO:1, SEQ ID NO:3, SEQ ID NO:5, or SEQ ID NO:7).

The methodologies of the present invention feature recombinant cells which overexpress at least one fatty acid desaturase. In one embodiment, a recombinant cell of the present invention has been genetically engineered to overexpress a *Thrauschytrium* sp. fatty acid desaturase (e.g., has been engineered to overexpress at least one of *Thrauschytrium* sp. Δ4 or Δ5 desaturase (the Fad4 or Fad5 gene product) (e.g., a fatty acid desaturase having the amino acid sequence of SEQ ID NO:2 or 4 or encoded by the nucleic acid sequence of SEQ ID NO:1 or 3).

In another embodiment, a recombinant cell of the present invention has been genetically engineered to overexpress a *Pythium irregulare* Δ5 or Δ6 desaturase (the Fad5-2 or Fad6 gene product) (e.g., a fatty acid desaturase having the amino acid sequence of SEQ ID NO:6 or 8 or encoded by a nucleic acid molecule having the nucleotide sequence of SEQ ID NO:5 or 7).

In another embodiment, the invention features a cell (e.g., a microbial cell) that has been transformed with a vector comprising a fatty acid desaturase nucleic acid sequence (e.g., a fatty acid desaturase nucleic acid sequence as set forth in SEQ ID NO:1, 3, 5, or 7).

Another aspect of the present invention features a method of modulating the production of fatty acids comprising culturing cells transformed by the nucleic acid molecules of the present invention (e.g., a desaturase) such that modulation of fatty acid production occurs (e.g., production of unsaturated fatty acids is enhanced). The method of culturing cells transformed by the nucleic acid molecules of the present invention (e.g., Fad4, Fad5, Fad5-2, and Fad6) to modulate the production of fatty acids is referred to herein as "biotransformation." The biotransformation processes can utilize recombinant cells and/or desaturases described herein. The term "biotransformation process," also referred to herein as "bioconversion processes," includes biological processes which result in the production (e.g., transformation or conversion) of any compound (e.g., substrate, intermediate, or product) which is upstream of a fatty acid desaturase to a compound (e.g., substrate, intermediate, or product) which is downstream of a fatty acid desaturase, in particular, an unsaturated fatty acid. In one embodiment, the invention features a biotransformation process for the production of an unsaturated fatty acid comprising contacting a cell which overexpresses at least one fatty acid desaturase with at least one appropriate substrate under conditions such that an unsaturated fatty acid is produced and, optionally, recovering the fatty acid. In a preferred embodiment, the invention features a biotransformation process for the production of unsaturated fatty acids comprising contacting a cell which overexpresses Fad4, Fad5, Fad5-2, or Fad6 with an appropriate substrate (e.g., an intermediate fatty acid) under conditions such that an unsaturated fatty acid (e.g., DHA, SDA, or GLA) is produced and, optionally, recovering the unsaturated fatty acid. Conditions under which an unsaturated fatty acid is produced can include any conditions which result in the desired production of an unsaturated fatty acid.

The cell(s) and/or enzymes used in the biotransformation reactions are in a form allowing them to perform their intended function (e.g., producing a desired fatty acids). The cells can be whole cells, or can be only those portions of the cells necessary to obtain the desired end result. The cells can be suspended (e.g., in an appropriate solution such as buffered solutions or media), rinsed (e.g., rinsed free of media from culturing the cell), acetone-dried, immobilized (e.g., with polyacrylamide gel or k-carrageenan or on synthetic supports, for example, beads, matrices and the like), fixed, cross-linked or permeablized (e.g., have permeablized membranes and/or walls such that compounds, for example, substrates, intermediates or products can more easily pass through said membrane or wall). The type of cell can be any cell capable of being used within the methods of the invention, e.g., plant, animal, or microbial cells.

An important aspect of the present invention involves growing the recombinant plant or culturing the recombinant microorganisms described herein, such that a desired compound (e.g., a desired unsaturated fatty acid) is produced. The term "culturing" includes maintaining and/or growing a living microorganism of the present invention (e.g., maintaining and/or growing a culture or strain). In one embodiment, a microorganism of the invention is cultured in liquid media. In another embodiment, a microorganism of the invention is cultured in solid media or semi-solid media. In a preferred embodiment, a microorganism of the invention is cultured in media (e.g., a sterile, liquid media) comprising nutrients essential or beneficial to the maintenance and/or growth of the microorganism (e.g., carbon sources or carbon substrate, for example complex carbohydrates such as bean or grain meal, starches, sugars, sugar alcohols, hydrocarbons, oils, fats, fatty acids, organic acids and alcohols; nitrogen sources, for example, vegetable proteins, peptones, peptides and amino acids derived from grains, beans and tubers, proteins, peptides and amino acids derived form animal sources such as meat, milk and animal byproducts such as peptones, meat extracts and casein hydrolysates; inorganic nitrogen sources such as urea, ammonium sulfate, ammonium chloride, ammonium nitrate and ammonium phosphate; phosphorus sources, for example, phosphoric acid, sodium and potassium salts thereof; trace elements, for example, magnesium, iron, manganese, calcium, copper, zinc, boron, molybdenum, and/or cobalt salts; as well as growth factors such as amino acids, vitamins, growth promoters and the like).

Preferably, microorganisms of the present invention are cultured under controlled pH. The term "controlled pH" includes any pH which results in production of the desired product (e.g., an unsaturated fatty acid). In one embodiment, microorganisms are cultured at a pH of about 7. In another embodiment, microorganisms are cultured at a pH of between 6.0 and 8.5. The desired pH may be maintained by any number of methods known to those skilled in the art.

Also preferably, microorganisms of the present invention are cultured under controlled aeration. The term "controlled aeration" includes sufficient aeration (e.g., oxygen) to result in production of the desired product (e.g., an unsaturated fatty acid). In one embodiment, aeration is controlled by regulating oxygen levels in the culture, for example, by regulating the amount of oxygen dissolved in culture media. Preferably, aeration of the culture is controlled by agitating the culture. Agitation may be provided by a propeller or similar mechanical agitation equipment, by revolving or shaking the growth vessel (e.g., fermentor) or by various pumping equipment. Aeration may be further controlled by the passage of sterile air or oxygen through the medium (e.g., through the fermentation mixture). Also preferably, microorganisms of the present invention are cultured without excess foaming (e.g., via addition of antifoaming agents).

Moreover, plants or microorganisms of the present invention can be cultured under controlled temperatures. The term "controlled temperature" includes any temperature which results in production of the desired product (e.g., an unsaturated fatty acid). In one embodiment, controlled temperatures include temperatures between 15° C. and 95° C. In another embodiment, controlled temperatures include temperatures between 15° C. and 70° C. Preferred temperatures are between 20° C. and 55° C., more preferably between 30° C. and 45° C. or between 30° C. and 50° C.

Microorganisms can be cultured (e.g., maintained and/or grown) in liquid media and preferably are cultured, either continuously or intermittently, by conventional culturing methods such as standing culture, test tube culture, shaking culture (e.g., rotary shaking culture, shake flask culture, etc.), aeration spinner culture, or fermentation. In a preferred embodiment, the microorganisms are cultured in shake flasks. In a more preferred embodiment, the microorganisms are cultured in a fermentor (e.g., a fermentation process). Fermentation processes of the present invention include, but are not limited to, batch, fed-batch and continuous methods of fermentation. The phrase "batch process" or "batch fermentation" refers to a closed system in which the composition of media, nutrients, supplemental additives and the like is set at the beginning of the fermentation and not subject to alteration during the fermentation, however, attempts may be made to control such factors as pH and oxygen concentration to prevent excess media acidification and/or microorganism death. The phrase "fed-batch process" or "fed-batch" fermentation refers to a batch fermentation with the exception that one or more substrates or supplements are added (e.g., added in increments or continuously) as the fermentation progresses. The phrase "continuous process" or "continuous fermentation" refers to a system in which a defined fermentation media is added continuously to a fermentor and an equal amount of used or "conditioned" media is simultaneously removed, preferably for recovery of the desired product (e.g., an unsaturated fatty acid). A variety of such processes have been developed and are well-known in the art.

The phrase "culturing under conditions such that a desired compound (e.g., an unsaturated fatty acid, for example, DHA) is produced" includes maintaining and/or growing plants or microorganisms under conditions (e.g., temperature, pressure, pH, duration, etc.) appropriate or sufficient to obtain production of the desired compound or to obtain desired yields of the particular compound being produced. For example, culturing is continued for a time sufficient to produce the desired amount of a unsaturated fatty acid (e.g., DHA). Preferably, culturing is continued for a time sufficient to substantially reach maximal production of the unsaturated fatty acid. In one embodiment, culturing is continued for about 12 to 24 hours. In another embodiment, culturing is continued for about 24 to 36 hours, 36 to 48 hours, 48 to 72 hours, 72 to 96 hours, 96 to 120 hours, 120 to 144 hours, or greater than 144 hours. In another embodiment, culturing is continued for a time sufficient to reach production yields of unsaturated fatty acids, for example, cells are cultured such that at least about 15 to 20 g/L of unsaturated fatty acids are produced, at least about 20 to 25 g/L unsaturated fatty acids are produced, at least about 25 to 30 g/L unsaturated fatty acids are produced, at least about 30 to 35 g/L unsaturated fatty acids are produced, at least about 35 to 40 g/L unsaturated fatty acids are produced (e.g., at least about 37 g/L unsaturated fatty acids) or at least about 40 to 50 g/L unsaturated fatty acids are produced. In yet another embodiment, microorganisms are cultured under conditions such that a preferred yield of unsaturated fatty acids, for example, a yield within a range set forth above, is produced in about 24 hours, in about 36 hours, in about 48 hours, in about 72 hours, or in about 96 hours.

In producing unsaturated fatty acids, it may further be desirable to culture cells of the present invention in the presence of supplemental fatty acid biosynthetic substrates. The term "supplemental fatty acid biosynthetic substrate" includes an agent or compound which, when brought into contact with a cell or included in the culture medium of a cell, serves to enhance or increase unsaturated fatty acid biosynthesis. Supplemental fatty acid biosynthetic substrates of the present invention can be added in the form of a concentrated solution or suspension (e.g., in a suitable solvent such as water or buffer) or in the form of a solid (e.g., in the form of a powder). Moreover, supplemental fatty acid biosynthetic substrates of the present invention can be added as a single aliquot, continuously or intermittently over a given period of time.

The methodology of the present invention can further include a step of recovering a desired compound (e.g., an unsaturated fatty acid). The term "recovering" a desired compound includes extracting, harvesting, isolating or purifying the compound from culture media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), dialysis, filtration, concentration, crystallization, recrystallization, pH adjustment, lyophilization and the like. For example, a compound can be recovered from culture media by first removing the microorganisms from the culture. Media is then passed through or over a cation exchange resin to remove unwanted cations and then through or over an anion exchange resin to remove unwanted inorganic anions and organic acids having stronger acidities than the unsaturated fatty acid of interest (e.g., DHA).

Preferably, a desired compound of the present invention is "extracted," "isolated" or "purified" such that the resulting preparation is substantially free of other components (e.g., free of media components and/or fermentation byproducts). The language "substantially free of other components" includes preparations of desired compound in which the compound is separated (e.g., purified or partially purified) from media components or fermentation byproducts of the culture from which it is produced. In one embodiment, the preparation has greater than about 80% (by dry weight) of the desired compound (e.g., less than about 20% of other media components or fermentation byproducts), more preferably greater than about 90% of the desired compound (e.g., less than about 10% of other media components or fermentation byproducts), still more preferably greater than about 95% of the desired compound (e.g., less than about 5% of other media components or fermentation byproducts), and most preferably greater than about 98-99% desired compound (e.g., less than about 1-2% other media components or fermentation byproducts). When the desired compound is an unsaturated fatty acid that has been derivatized to a salt, the compound is preferably further free (e.g., substantially free) of chemical contaminants associated with the formation of the salt. When the desired compound is an unsaturated fatty acid that has been derivatized to an alcohol, the compound is preferably further free (e.g., substantially free) of chemical contaminants associated with the formation of the alcohol.

In an alternative embodiment, the desired unsaturated fatty acid is not purified from the plant or microorganism, for example, when the plant or microorganism is biologically non-hazardous (e.g., safe). For example, the entire plant or culture (or culture supernatant) can be used as a source of product (e.g., crude product). In one embodiment, the plant or culture (or culture supernatant) supernatant is used without modification. In another embodiment, the plant or culture (or culture supernatant) is concentrated. In yet another embodiment, the plant or culture (or culture supernatant) is pulverized, dried, or lyophilized.

B. High Yield Production Methodologies

A particularly preferred embodiment of the present invention is a high yield production method for producing unsaturated fatty acids, e.g., DHA, comprising culturing a manipulated plant or microorganism under conditions such that the unsaturated fatty acid is produced at a significantly high yield. The phrase "high yield production method," for example, a high yield production method for producing a desired compound (e.g., for producing an unsaturated fatty acid) includes a method that results in production of the desired compound at a level which is elevated or above what is usual for comparable production methods. Preferably, a high yield production method results in production of the desired compound at a significantly high yield. The phrase "significantly high yield" includes a level of production or yield which is sufficiently elevated or above what is usual for comparable production methods, for example, which is elevated to a level sufficient for commercial production of the desired product (e.g., production of the product at a commercially feasible cost). In one embodiment, the invention features a high yield production method of producing unsaturated fatty acids that includes culturing a manipulated plant or microorganism under conditions such that an unsaturated fatty acid is produced at a level greater than 2 g/L. In another embodiment, the invention features a high yield production method of producing unsaturated fatty acids that includes culturing a manipulated plant or microorganism under conditions such that an unsaturated fatty acid is produced at a level greater than 10 g/L. In another embodiment, the invention features a high yield production method of producing unsaturated fatty acids that includes culturing a manipulated plant or microorganism under conditions such that an unsaturated fatty acid is produced at a level greater than 20 g/L. In yet another embodiment, the invention features a high yield production method of producing unsaturated fatty acids that includes culturing a manipulated plant or microorganism under conditions such that an unsaturated fatty acid is produced at a level greater than 30 g/L. In yet another embodiment, the invention features a high yield production method of producing unsaturated fatty acids that includes culturing a manipulated plant or microorganism under conditions such that an unsaturated fatty acid is produced at a level greater than 40 g/L.

The invention further features a high yield production method for producing a desired compound (e.g., for producing an unsaturated fatty acid) that involves culturing a manipulated plant or microorganism under conditions such that a sufficiently elevated level of compound is produced within a commercially desirable period of time. In an exemplary embodiment, the invention features a high yield production method of producing unsaturated fatty acids that includes culturing a manipulated plant or microorganism under conditions such that an unsaturated fatty acid is produced at a level greater than 15-20 g/L in 36 hours. In another embodiment, the invention features a high yield production method of producing unsaturated fatty acids that includes culturing a manipulated plant or microorganism under conditions such that an unsaturated fatty acids produced at a level greater than 25-30 g/L in 48 hours. In another embodiment, the invention features a high yield production method of producing unsaturated fatty acids that includes culturing a manipulated plant or microorganism under conditions such that an unsaturated fatty acids produced at a level greater than 35-40 g/L in 72 hours, for example, greater that 37 g/L in 72 hours. In another embodiment, the invention features a high yield production method of producing unsaturated fatty acids that includes culturing a manipulated plant or microorganism under conditions such that an unsaturated fatty acid is produced at a level greater than 30-40 g/L in 60 hours, for example, greater that 30, 35 or 40 g/L in 60 hours. Values and ranges included and/or intermediate within the ranges set forth herein are also intended to be within the scope of the present invention. For example, unsaturated fatty acid production at levels of at least 31, 32, 33, 34, 35, 36, 37, 38 and 39 g/L in 60 hours are intended to be included within the range of 30-40 g/L in 60 hours. In another example, ranges of 30-35 g/L or 35-40 g/L are intended to be included within the range of 30-40 g/L in 60 hours. Moreover, the skilled artisan will appreciate that culturing a manipulated microorganism to achieve a production level of, for example, "30-40 g/L in 60 hours" includes culturing the microorganism for additional time periods (e.g., time periods longer than 60 hours), optionally resulting in even higher yields of an unsaturated fatty acid being produced.

IV. Compositions

The desaturase nucleic acid molecules, proteins, and fragments thereof, of the invention can be used to produce unsaturated fatty acids which can be incorporated into compositions. Compositions of the present invention include, e.g., compositions for use as animal feed, compositions for use as neutraceuticals (e.g., dietary supplements), and pharmaceutical compositions suitable for administration.

Such pharmaceutical compositions typically comprise an unsaturated fatty acid and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a LCPUFA, or a fragment thereof, produced by the nucleic acid and protein molecules of the present invention) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with a LCPUFA in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The pharmaceutical compositions can be included in a container, pack, or dispenser together with instructions for administration.

This invention is further illustrated by the following examples which should not be construed as limiting. The contents of all references, patents and published patent applications cited throughout this application, as well as the figures, are incorporated herein by reference.

EXAMPLES

Materials: *Thraustochytrium* s.p ATCC 21685 and *Pythium irregulare* were purchased from American type culture collection (12301 Parklawn Drive, Rockville, Md., 20852 USA) and grown in a medium (Weete, J. D., et al. (1997) Lipids 32:839-845) at 24° C. for 7 days. After then biomass were harvested by centrifugation and used for RNA isolation.

Example 1

Construction and Screening of cDNA Library

Total RNA was isolated from the above materials according to Qiu and Erickson (Qiu, X. and Eriekson, L. (1994) Plant Mol. Biol. Repr. 12:209-214). The cDNA library was constructed from the total RNA. The first strand cDNA was synthesized by superscript II reverse transcriptase from Gibco-BRL. The second strand cDNA was synthesized by DNA polymerase I from Stratagene. After size fractionation, cDNA inserts larger than 1 kb were ligated into λ Uni-Zap XR vector (Stratagene). The recombinant ~DNAs were then packed with Gigapack III Gold packaging extract (Stratagene) and plated on NZY plates. The resulting library represented more than 5×106 independent clones. Screening of the cDNA library was performed according to standard methods (Sambrook, J, Fritseh, E. F., Maniatis, T. (1989) Molecular cloning—A laboratory manual. (Cold Spring Harbor, N.Y., USA.)

Example 2

RT-PCR

The single strand cDNA was synthesized by superscript II reverse transcriptase (Gibco-BRL) from total RNA and was then used as the template for PCR reaction with two degenerate primers (The forward primer: GCNCA/GANGAN-CAC/TCCNGGXGG (SEQ ID NO:9) and the reverse primer: ATNTG/TNGGA/GAANAG/AG/ATGG/ATG (SEQ ID NO:10)). The PCR amplification consisted of 35 cycles with 1 min at 94° C., 1.5 min at 55° C. and 2 min at 72° C. followed by an extension step at 72° C. for 10 min. The amplified products from 800 bp to 1000 bp were isolated from agarose gel and purified by a kit (Qiaex II gel purification, Qiagen), and subsequently cloned into the TA cloning vector pCR®2.1 (Invitrogen). The cloned inserts were then sequenced by PRISM DyeDeoxy Terminator Cycle Sequencing System (Perkin Elmer/Applied Biosystems).

Example 3

Expression of FAD4, FAD5, FAD5-2, AND FAD6 in Yeast

The open reading frames of Fad4, Fad5, Fad5-2, and Fad6 were amplified by PCR using the Precision Plus enzyme (Stratagene) and cloned into a TA cloning vector (pCR®2.1, Invitrogen). Having confirmed that the PCR products were identical to the original cDNAs by sequencing, the fragments were then released by a BamHI-EcoRI double digestion and inserted into the yeast expression vector pYES2 (Invitrogen) under the control of the inducible promoter GAL1.

Yeast strains InvSc2 (Invitrogen) was transformed with the expression constructs using the lithium acetate method and transformants were selected on minimal medium plates lacking uracil (Gietz, D., et al. (1992) Nucleic Acids Res. 20:1425; Covello, P. S. and Reed, D. W. (1996) Plant Physiol. 111:223-226).

Transformants were first grown in minimal medium lacking uracil and containing glucose at 28° C. After overnight culture, the cells were spun down, washed and resuspended in distilled water. Minimal medium containing 2% galactose, with or without 0.3 mM substrate fatty acids in the presence of 0.1% tergitol, was inoculated with the yeast transformant cell suspension and incubated at 20° C. for three days, and then 15° C. for another three days.

Example 4

Fatty Acid Analysis

*Thraustochytrium, Pythium irregulare* and yeast cells were harvested and washed twice with distilled water. Then 2 mL methanolic KOH (7.5% w/v KOH in 95% methanol) was added to the materials and the mixture sealed in a 12 ml glass culture tube was heated to 80° C. for 2 hours. 0.5 mL water was added and the sample was extracted twice with 2 mL hexane to remove the non-saponifiable lipids. The remaining aqueous phase was then acidified by adding 1 mL 6 N HCl and extracted twice with 2 mL hexane. The hexane phases were combined and dried under a stream of nitrogen. 2 mL 3 N methanolic HCl (SUPELCO, Supelco Park, Bellefonte, Pa. 16823-0048) was added and the mixture was heated at 80° C. for 2 hours. After cooling to room temperature, 1 mL 0.9% NaCl was added and the mixture extracted twice with 2×2 mL hexane. The combined hexane was evaporated under nitrogen. The resulting fatty acid methyl esters (FAMEs) were analyzed by GC and GC-MS according to Covello & Reed (Covello, P. S. and Reed, D. W. (1996) Plant Physiol. 111: 223-226).

GC/MS analysis was performed in standard EI mode using a Fisons VG TRIO 2000 mass spectrometer (VG Analytical, UK) controlled by Masslynx version 2.0 software, coupled to a GC 8000 Series gas chromatograph. A DB-23 column (30M×0.25 mm i.d., 0.25 Ilm film thickness, J&W Scientific, Folsom, Calif.) that was temperature-programmed at 180° C. for 1 min, then 4 C/min to 240° C. and held for 15 minutes, was used for FAME analysis.

Example 5

Transformation of *Brassica juncea* and Flax (*Linum usitatissimum*) and Exogenous Fatty Acid Treatment The hypocotyls of 5-6 day seedlings of *B. juncea* and flax were used as explants for inoculation with the *Agrobacterium tumefaciens* that hosts binary vectors with the full-length cDNAs under the control of the different promoters. The 20-day transgenic seedlings were used for exogenous fatty acid treatment. The seedling was divided into three parts: leaves, stems and roots. Each was cut into the small pieces and placed in a 24-well titer plate. To each well, 2 mL 0.05% sodium salt of substrates (NuCheck Prep Inc., Elysian, Minn.) was added. The plate was then incubated at 24° C. for 4 h with gentle shaking. After incubation, the plant tissues were washed three times with water and then used for fatty acid analysis.

Example 6

Fatty Acid Profile of the *Thrauschytrium* sp.

*Thraustochytrium* and *Pythium irregulare* have recently drawn scientific attention due to its ability in production of LCPUFAs such as DHA, AA, EPA and DPA. FIGS. 23 and 24 show the fatty acid composition of the lipids isolated from 7 day cultures of *Thraustochytrium* sp. and *Pythium irregulare*, respectively. As shown in the tables, the microorganisms contain a broad range of polyunsaturated fatty acids, from both n-3 and n-6 families, from 18-carbon Δ6 fatty acids (gamma-linolenic acid and steardonic acid) to 22-carbon Δ4 fatty acids (DHA and DPA). The organisms, especially *Thraustochytrium* sp., appear to contain a full-set of desaturation and elongation enzymes required for the DHA and DPA biosynthesis. The strain lacks 24-carbon polyunsaturated fatty acids, the proposed precursors for DHA and DPA synthesis in Precher's pathway (Voss, A., et al. (1991) J. Biol. Chem. 266: 19995-20000; Mohammed, B. S., et al. (1997) Biochem. J. 326:425-430). The 24-carbon fatty acid may not be involved in in vivo synthesis of 22-carbon Δ4 fatty acids such as DHA and DPA in *Thraustochytrium* sp.

Example 7

Identification of cDNAs Coding for the "Front-End" Desaturase

To identify genes coding for desaturases involved in biosynthesis of LCFUFAs in *Thraustochytrium* sp. and *Pythium irregulare*, a PCR-based cloning strategy was adopted. Two degenerate primers are designed to target the heme-binding motif of N-terminal extension of cyt b5-like domain in front-end desaturases and the third conservative histidine motif in all microsomal desaturases, respectively. The rational behind the design is that the desaturases involved in EPA and DHA biosynthesis in *Thraustochytrium* sp. and *Pythium irregulare*, should have similar primary structure as other front-end desaturases, i.e. N-terminal extension of cyt b5-like domain in the desaturase. Four cDNAs fragments were identified from *Thraustochytrium* sp. and *Pythium irregulare* that encode fusion proteins containing cyt b5-like domain in the N-terminus.

To isolate full-length cDNA clones, the four inserts were used as probes to screen cDNA libraries of *Thraustochytrium* sp. and *Pythium irregulare*, which resulted in identification of several cDNA clones in each group. Sequencing of all those clones identified four full-length cDNAs which were named as Fad4, Fad5, Fad5-2 and Fad6. The open reading frame of Fad4 is 1560 bp and codes for 519 amino acids with molecular weight of 59.1 kDa (FIG. 1). Fad5 is 1230 bp in length and codes for 439 amino acids with molecular weight of 49.8 kDa (FIG. 2). A sequence comparison of these two sequences from *Thraustochytrium* sp. showed only 16% amino acid identity between the deduced proteins. A detailed analysis revealed that Fad4 is 80 amino acids longer than Fad5, occurring between the second and third conservative histidine motifs (FIG. 3). The open reading frame of Fad5-2 from *Pythium irregulare* is 1371 bp and codes for 456 amino acids (FIG. 4). Fad6 from *Pythium irregulare* is 1383 bp in length and codes for 460 amino acids (FIG. 5). Sequence comparison of the two sequences from *Pythium irregulare* showed over 39% similarity between the deduced proteins (FIG. 6).

A BLASTP™ search of the protein database revealed the following hits for each of the four proteins, Fad4, Fad5, Fad5-2, and Fad6:

Fad 4 (519 Amino Acid Residues)

Blastp nr

| Accession No. | Organism | Description | Length | % Identity |
|---|---|---|---|---|
| AF067654 | *Mortierella alpina* | Δ5 fatty acid desaturase | 509 | 29 |
| AF054824 | *Mortierella alpina* | Δ5 microsomal desaturase | 509 | 28 |
| AB022097 | *Dictyostelium discoideum* | Δ5 fatty acid desaturase | 507 | 27 |
| AB029311 | *Dictyostelium discoideum* | fatty acid desaturase | 519 | 26 |
| L11421 D90914 | *Synechocystis* sp. | Δ6 desaturase | 410 | 25 |

Fad 5 (439 Amino Acid Residues)

Blastp nr

| Accession No. | Organism | Description | Length | % Identity |
|---|---|---|---|---|
| AF139720 | *Euglena gracilis* | Δ8 fatty acid desaturase | 404 | 29 |
| AF007561 | *Borago officinalis* | Δ6 desaturase | 421 | 27 |
| U79010 | *Borago officinalis* | Δ6 desaturase | 421 | 27 |
| AF309556 | *Danio rerio* | Δ6 fatty acid desaturase | 422 | 26 |
| AF110510 | *Mortierella alpina* | Δ6 fatty acid desaturase | 463 | 25 |

Fad 5-2 (456 Amino Acid Residues)

Blastp nr

| Accession No. | Organism | Description | Length | % Identity |
|---|---|---|---|---|
| AB029311 | *Dictostelium discoideum* | Fatty acid desaturase | 443 | 41 |
| AB022097 | *Dictostelium discoideum* | Δ5 fatty acid desaturase | 445 | 39 |
| AF067654 | *Mortierella alpina* | Δ5 fatty acid desaturase | 441 | 38 |
| AF054824 | *Mortierella alpina* | Δ5 microsomal desaturase | 441 | 38 |
| L11421 D90914 | *Synechocystis* sp. | Δ6 desaturase | 361 | 28 |

Fad 6 (459 Amino Acid Residues)

Blastp nr

| Accession No. | Organism | Description | Length | % Identity |
|---|---|---|---|---|
| AF110510 | *Mortierella alpina* | Δ6 fatty acid desaturase | 437 | 38 |
| AB020032 | *Mortierella alpina* | Δ6 fatty acid desaturase | 437 | 38 |

-continued

| Accession No. | Organism | Description | Length | % Identity |
|---|---|---|---|---|
| AF306634 | Mortierella isabellina | Δ6 fatty acid desaturase | 437 | 38 |
| AF307940 | Mortierella alpina | Δ6 fatty acid desaturase | 438 | 38 |
| AJ250735 | Ceratodon purpureus | Δ6 fatty acid desaturase | 438 | 36 |

Example 8

Expression of FAD4, FAD5, FAD5-2, and FAD6 in Yeast

Figure 8A:
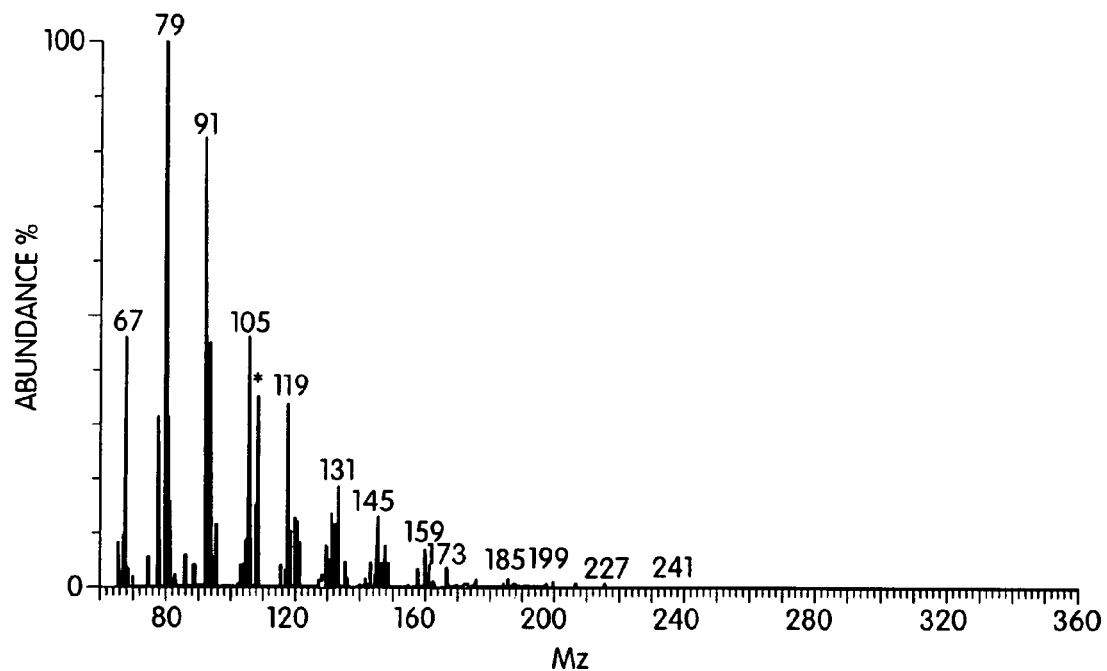
FIG. 8 is a gas chromatographic/mass spectroscopy (MS) analysis of FAMEs of the new peak in FIG. 7; (A) the Fad4 product; (B) the DHA (22:6, n-3) standard.
Figure 8B:
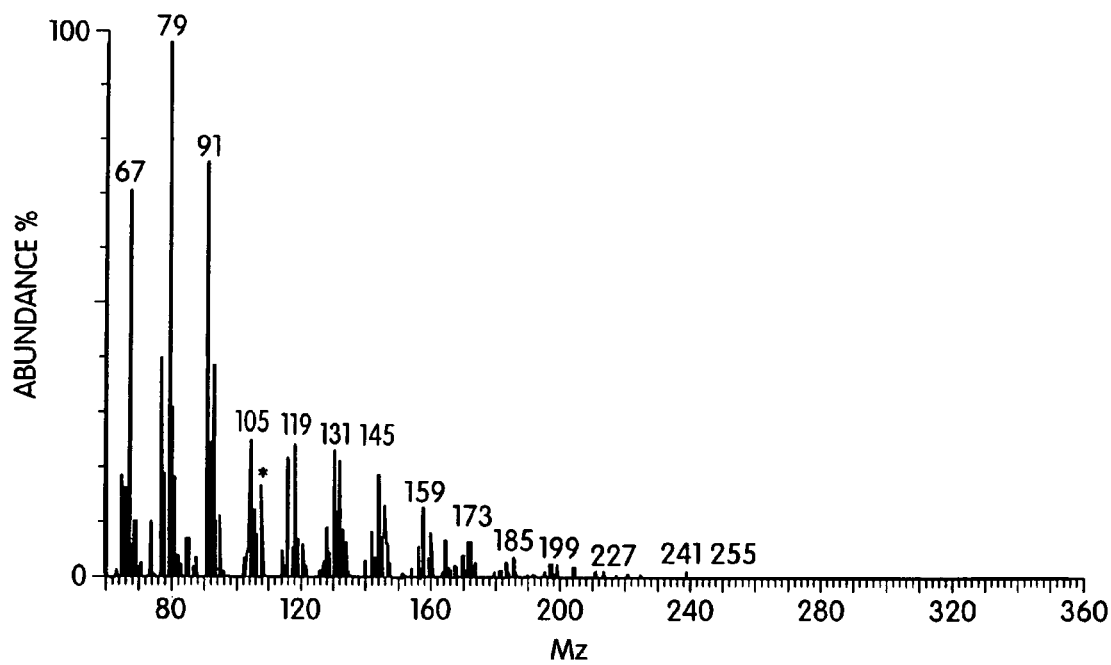

To confirm the function of Fad4, the full-length cDNA was expressed in the yeast strain InvSc2 under the control of the inducible promoter. FIG. 7 shows that with supplementation of the medium with 22:5 (7,10,13,16,19), yeast cells containing Fad4 cDNA had an extra fatty acid as compared to the vector control. The peak has a retention time identical to the DHA standard. LC/MS analysis of the free fatty acid showed that it yields deprotonated molecular ions (m/z=279) identical to the DHA standard in negative ion electrospray. Moreover, GC/MS analysis of the FAME confirmed that the spectrum of the peak is identical to that of the DHA standard (FIG. 8). These results indicate that Fad4 is a Δ4 fatty acid desaturase which is able to introduce a double bond at position 4 of the 22:5(7,10,13,16,19) substrate, resulting in a Δ4 desaturated fatty acid, DHA (22:6-4,7,10,13,16,19).

Figure 9:
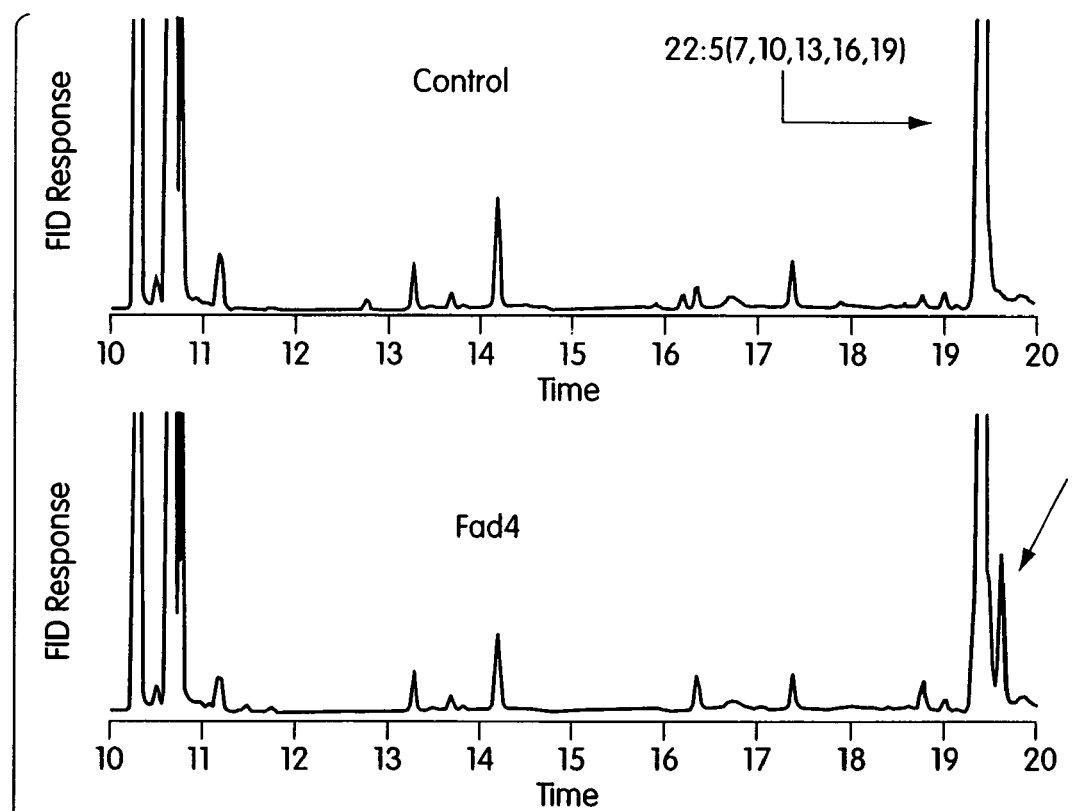
FIG. 9 is a GC analysis of FAMEs from yeast strain Invsc2 expressing Fad4 with exogenous substrate 22:4 (n-6).
Figure 10A:
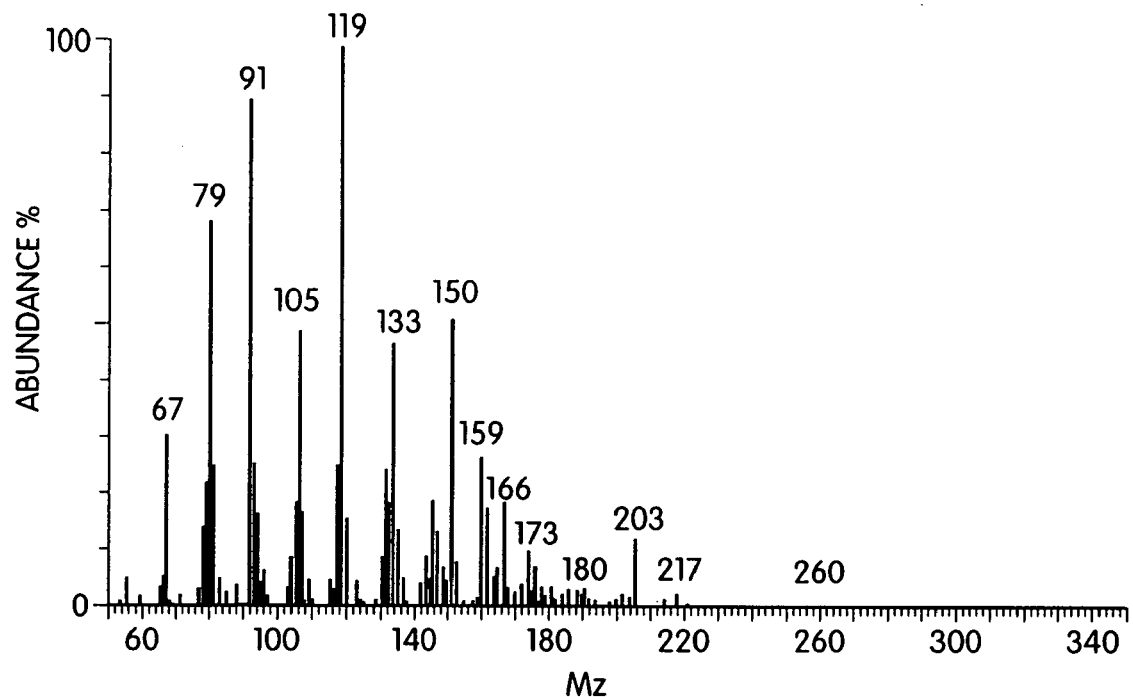
FIG. 10 is a GC/MS analysis FAMEs of the new peak in FIG. 9; (A) the Fad4 product; (B) the DPA (22:5, n-6) standard.
Figure 10B:
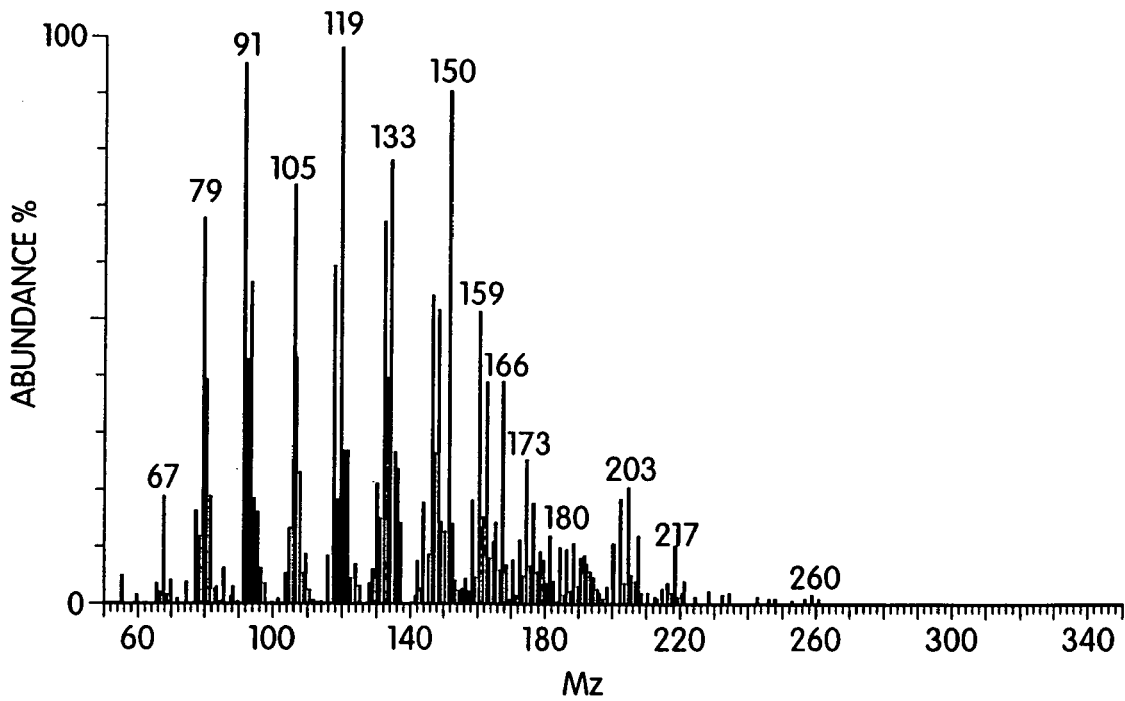

To further study the substrate specificity of the Fad4, a number of substrates including 18:2(9,12), 18:3(9,12,15), 20:3(8,11,14) and 22:4(7,10,13,16) were separately supplied to the yeast transformants. The results indicated Fad4 could also use 22:4 (7,10,13,16) as a substrate (FIG. 9) to produce another Δ4 desaturated fatty acid, DPA (22:5-4,7,10,13,16) (FIG. 10). The rest of the fatty acids examined were not effective substrates.

Figure 11:
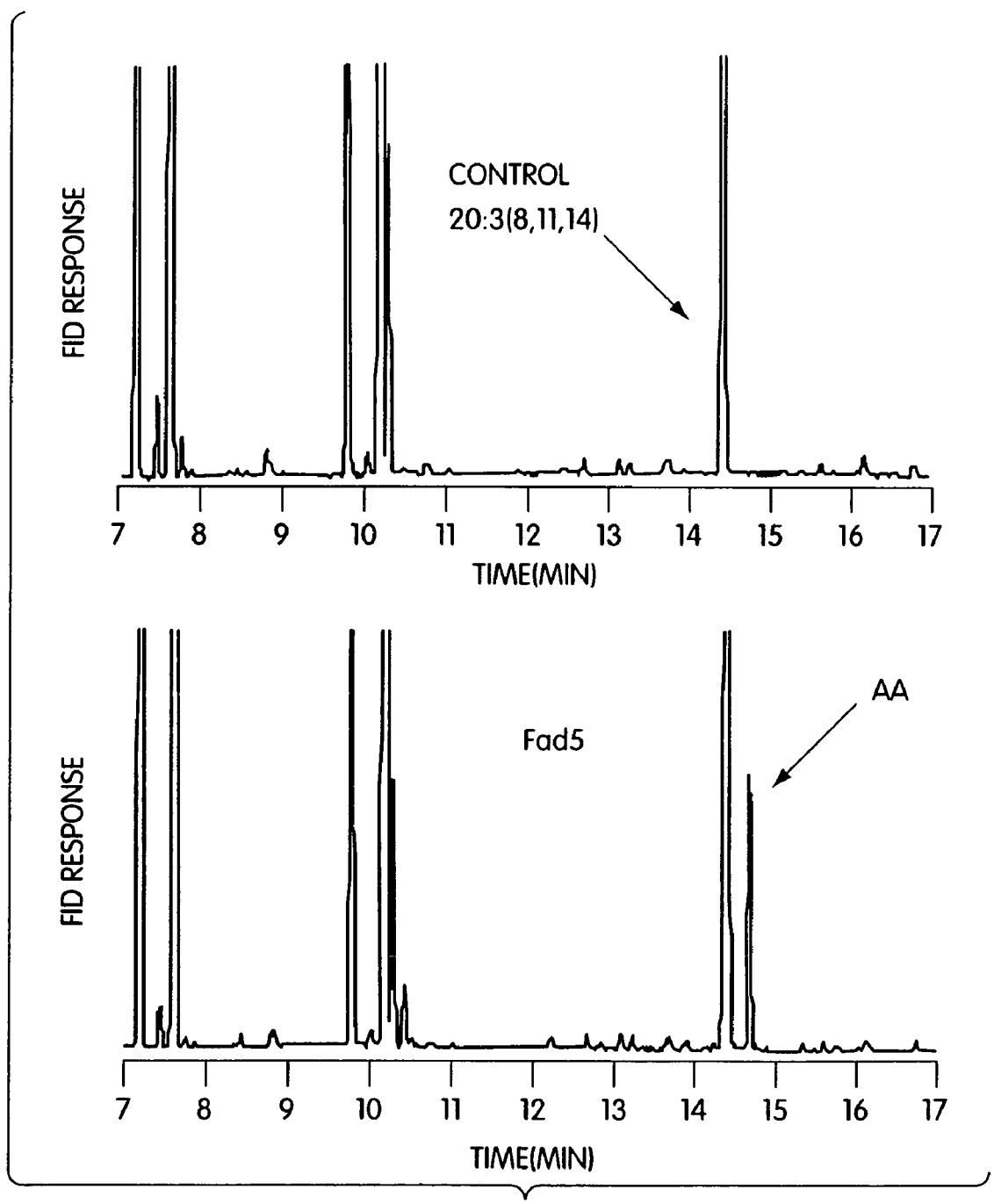
FIG. 11 is a GC analysis of FAMEs from yeast strain Invsc2 expressing Fad5 with exogenous substrate 20:3 (n-6).
Figure 12A:
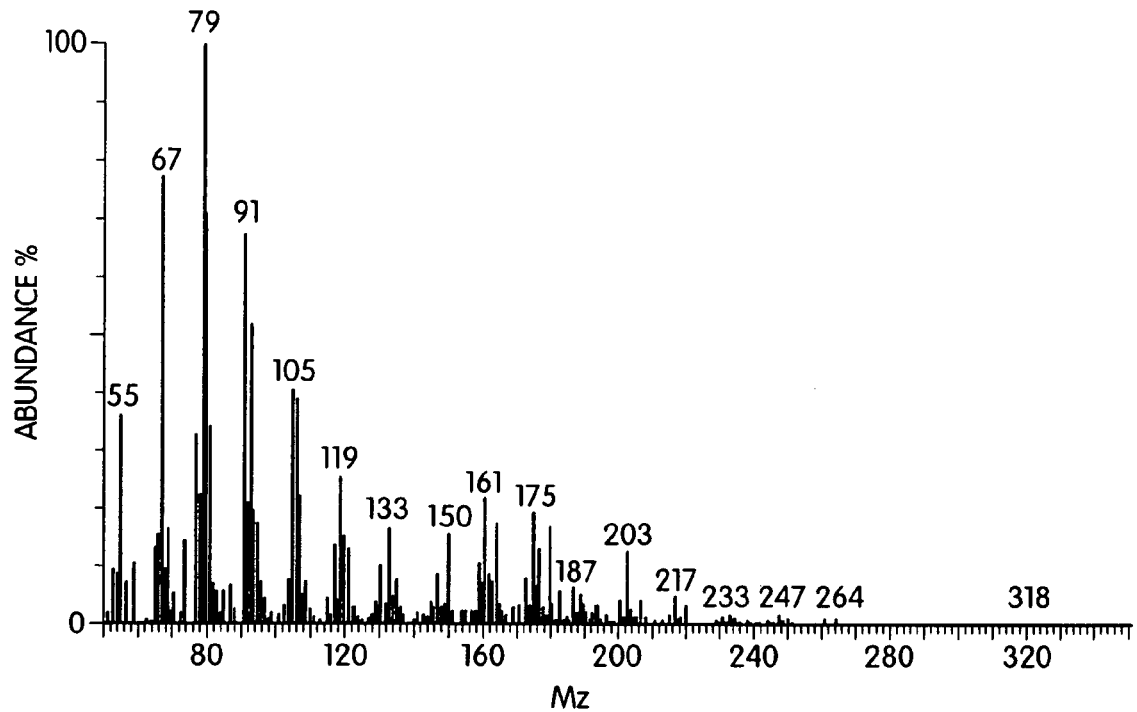
FIG. 12 is a GC/MS analysis of FAMES of the new peak in FIG. 11; (A) the Fad5 product; (B) the AA (20:4-5,8,11,14) standard.
Figure 12B:
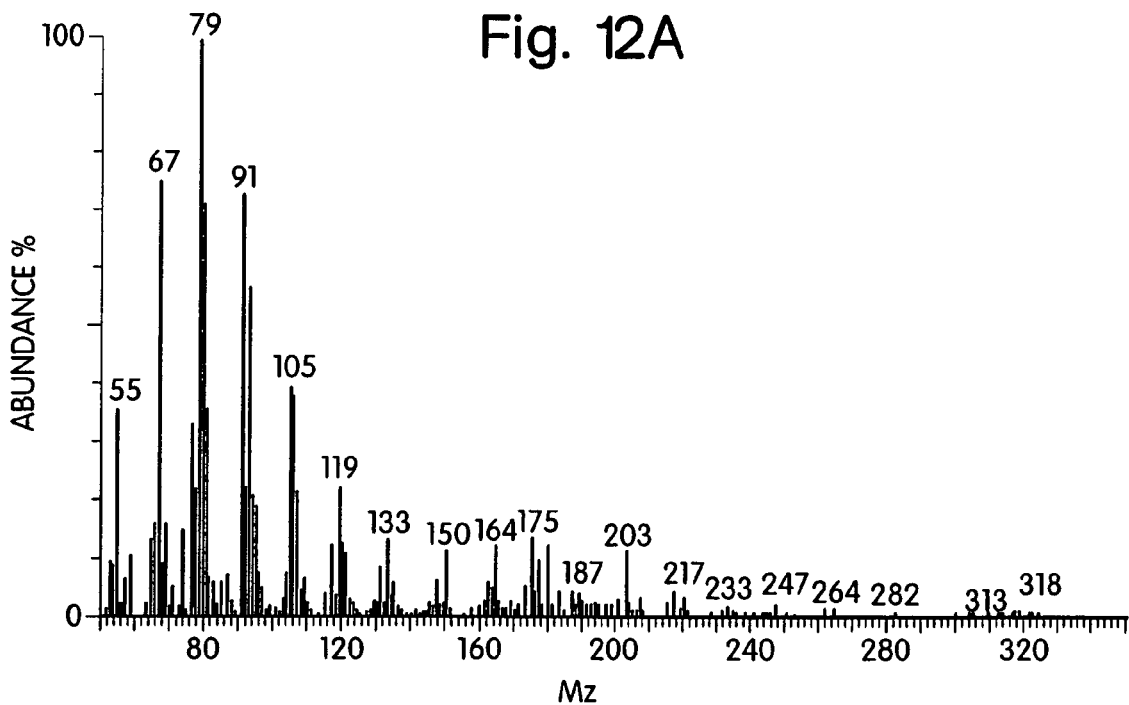

To confirm the function of Fad5 and Fad5-2, the *S. cerevisiae* Invsc2 was transformed with plasmids, which contain the open reading frame of the Fad5 and Fad5-2 respectively under the control of the galactose-inducible promoter. When the yeast transformants were induced by galactose in a medium containing homo-gamma-linolenic acid (HGLA, 20:3-8,11,14), an extra peak was observed in the chromatogram of FAMEs accumulating in the transformants compared with the control (FIG. 11). A comparison of the chromatogram with that of the standards revealed that the fatty acid had a retention time identical to the arachidonic acid standard (AA, 20:4-5,8,11,14). To further confirm the regiochemistry of the products, the FAMEs were analyzed by GC/MS. FIG. 12 indicates that the mass spectra of the new fatty acid and the AA standard are identical. These results demonstrate that Fad5 and Fad5-2 convert HGLA (20:3-8,11,13) into AA (20:4-5,8,11,14) in yeast.

Figure 13:
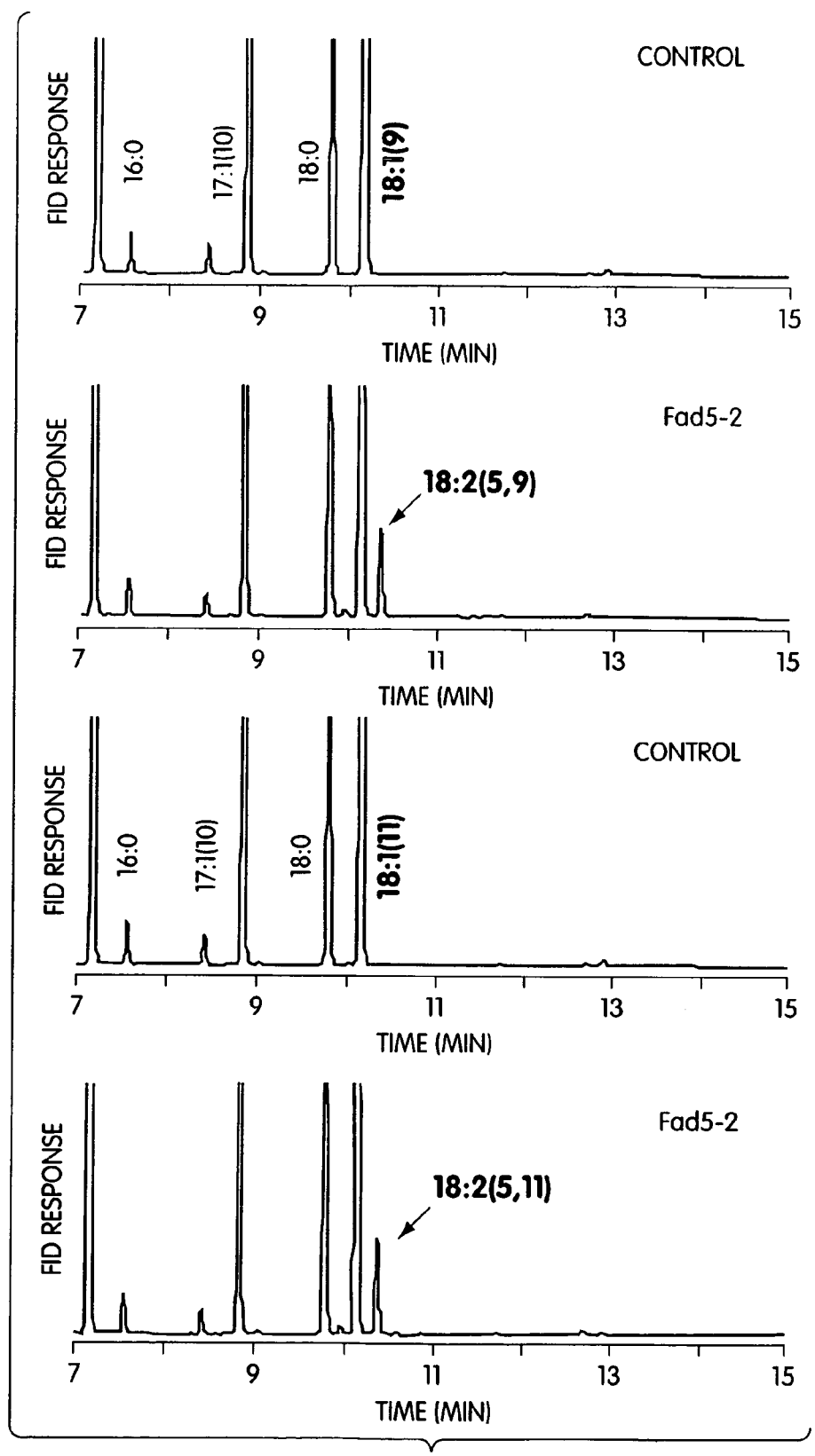
FIG. 13 is a GC analysis of FAMES from yeast strain AMY2α expressing Fad5-2 with exogenous substrate 18:1-9 (the upper panes) and 18:1-11 (the lower panel), respectively.

To further study the substrate specificity of Fad5-2, the plasmid containing Fad5-2 was transferred into another yeast strain AMY-2α where ole1, a Δ9 desaturase gene, is disrupted. The strain is unable to grow in minimal media without supplementation with mono-unsaturated fatty acids. In this experiment, the strain was grown in minimal medium supplemented with 17:1(10Z), a non-substrate of Fad5-2, which enabled study of the specificity of the enzyme towards various substrates, especially monounsaturates. A number of possible substrates including 16:1(9Z), 18:1(9Z), 18:1(11Z), 18:1(11E), 18:1(12E), 18:1(15Z), 18:2(9Z,12Z), 18:3(9Z,12Z,15Z), 20:2(11Z,14Z) and 20:3(11Z,14Z,17Z) were tested. Results indicated that Fad5-2 could desaturate unsaturated fatty acids with Δ9 ethylenic and Δ11 ethylenic double bonds, as well as the fatty acid with Δ8 ethylenic double bond (20:3-8,11,14). As shown in FIG. 13, Fad5-2 effectively converted both 18:1 (9Z) and 18:1 (11 Z) substrates into their corresponding Δ5 desaturated fatty acids, 18:2-5,9 (the retention time 10.34 min) and 18:1-5,11 (the retention time 10.44 min), respectively. Fad5-2 also desaturated trans fatty acid such as 18:1(11E) and 18:1(12E).

FIG. 25 is a comparison of substrate preference of Fad5-2 for fatty acid substrates tested in the yeast strain AMY-2α. The relative proportions of the substrates and the products accumulated are a useful indicator of substrate preference of the enzyme. As shown in FIG. 25, Fad5-2 prefers fatty acids with 20-carbon as substrates, such as 20:3(8Z,11Z,14Z), 20:3 (11Z,14Z,17Z) and 20:2(11Z,14Z). Whereas, the shorter chain fatty acid is a relatively weaker substrate for the enzyme in yeast.

Figure 14:
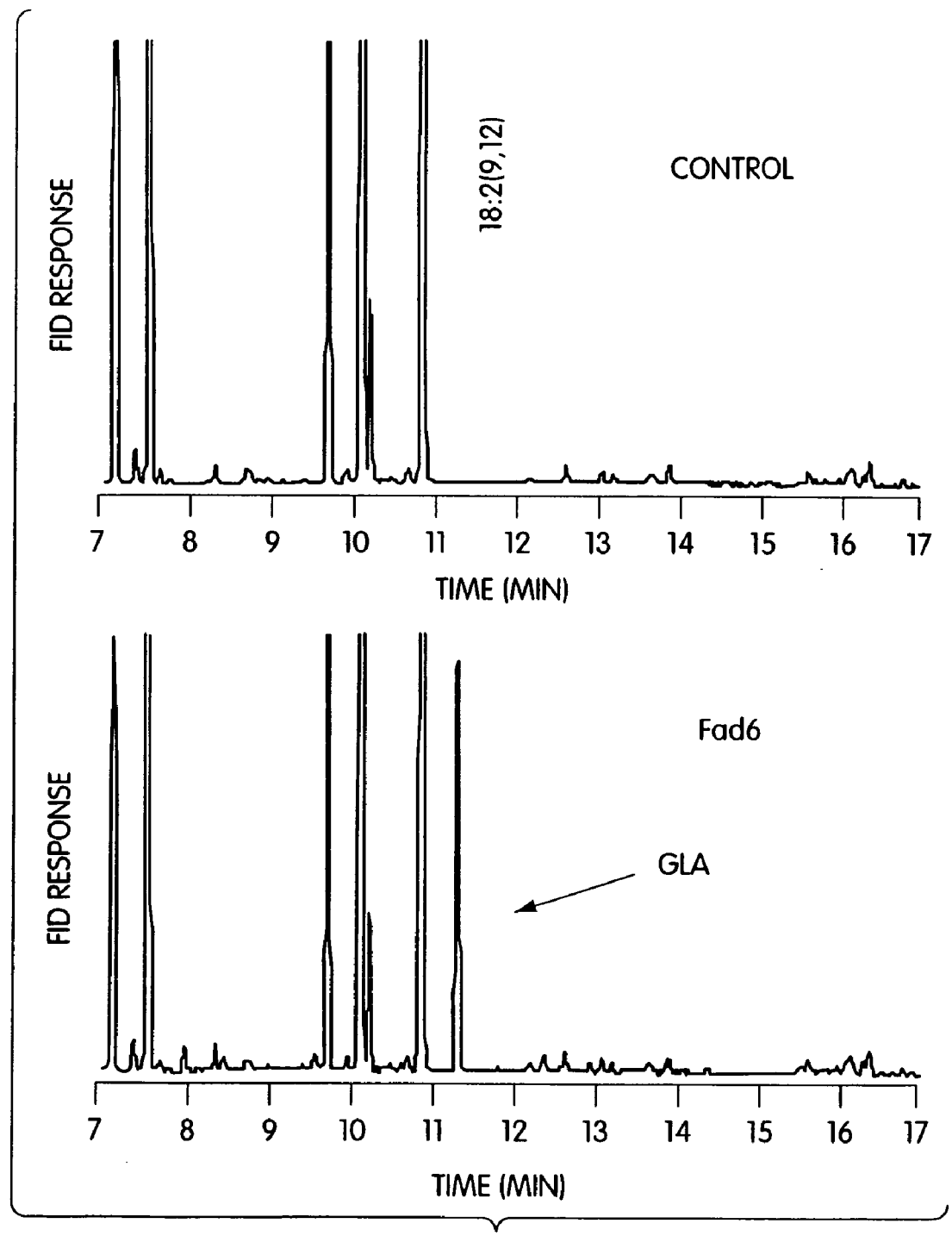
FIG. 14 is a GC analysis of FAMEs from yeast strain Invsc2 expressing Fad6 with exogenous substrate 18:2 (9,12).
Figure 15:
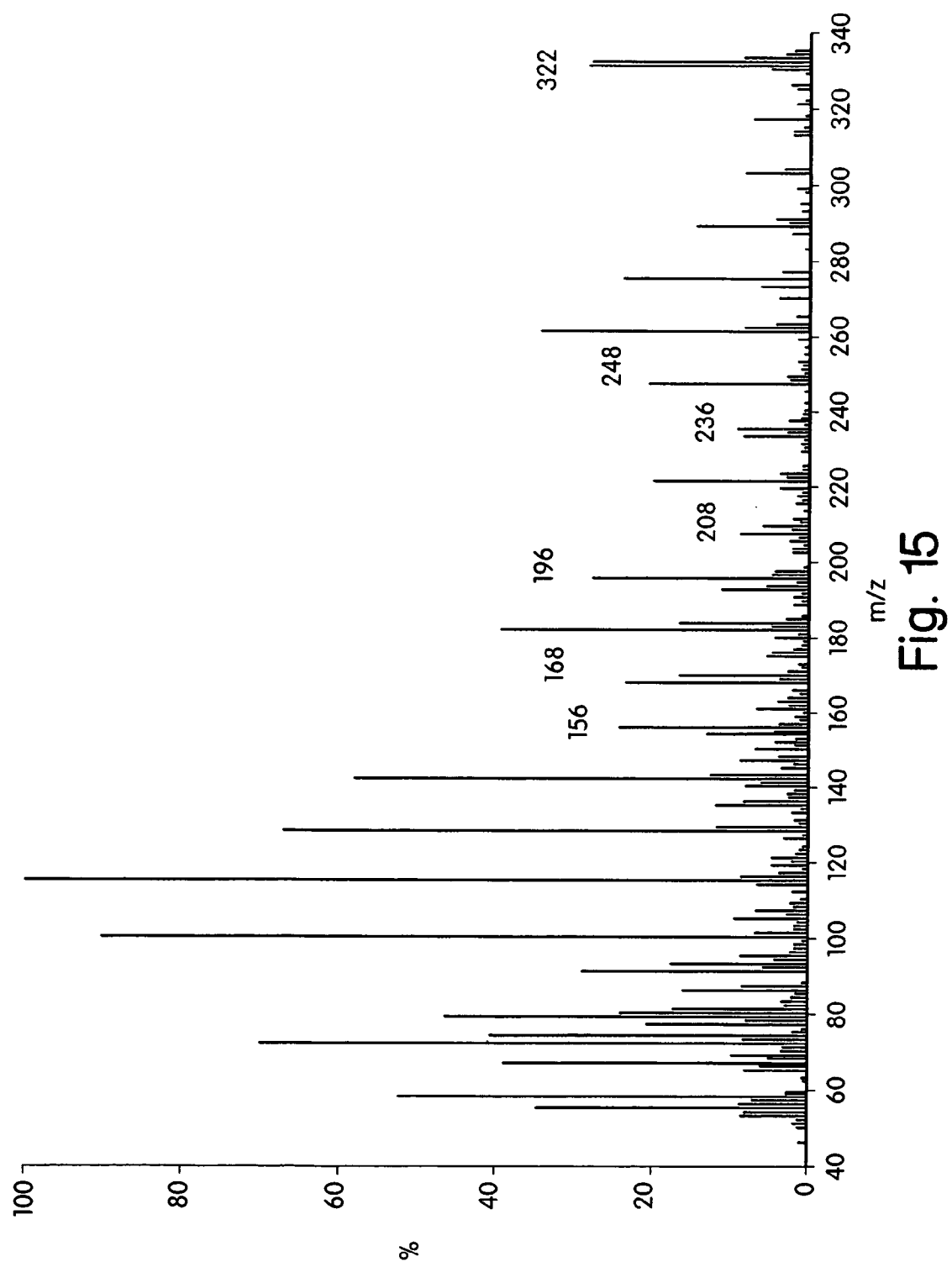
FIG. 15 is a MS analysis of the derivative of the new peak from FIG. 14. The structure of the diethylamide of the new fatty acid is shown with m/z values for ions that include the amide moiety. The three pairs of ions at m/z, 156/168, 196/208, and 236/248 are diagnostic for double bonds at the Δ6, Δ9, and Δ12 position, respectively.

To confirm the function of Fad6, the *S. cerevisiae* host strain Invsc2 was transformed with a plasmid containing the open reading frame of Fad6 under the control of the galactose-inducible promoter, GAL1. When the yeast transformant was induced by galactose in a medium containing linoleic acid, an extra peak was observed in the chromatogram of the FAMEs accumulating in the transformants compared with the control (FIG. 14). A comparison of the chromatogram with that of the standards revealed that the peak had a retention time identical to the gamma-linolenic acid (GLA, 18:3-6,9, 12) standard. To confirm the regioselectivity of the products, the diethylamine derivatives of fatty acids from the expressing strain were analyzed by GC-MS. FIG. 15 shows that the new peak is indeed GLA with three double bonds at the Δ6, Δ9, and Δ12 positions. Major fragments of n and n+1 carbons differing by 12 D are diagnostic of a double bond between carbon n+1 and n+2. Thus, the fragments at 156 and 168, 196 and 208, and 236 and 248, indicate double bonds at the Δ6, Δ9, and Δ12 positions, respectively. These results demonstrate that Fad6 is a Δ6 desaturase that converts linoleic acid (18:2) to GLA in yeast.

Example 9

Expression of FAD4 in *B. juncea*

Figure 16:
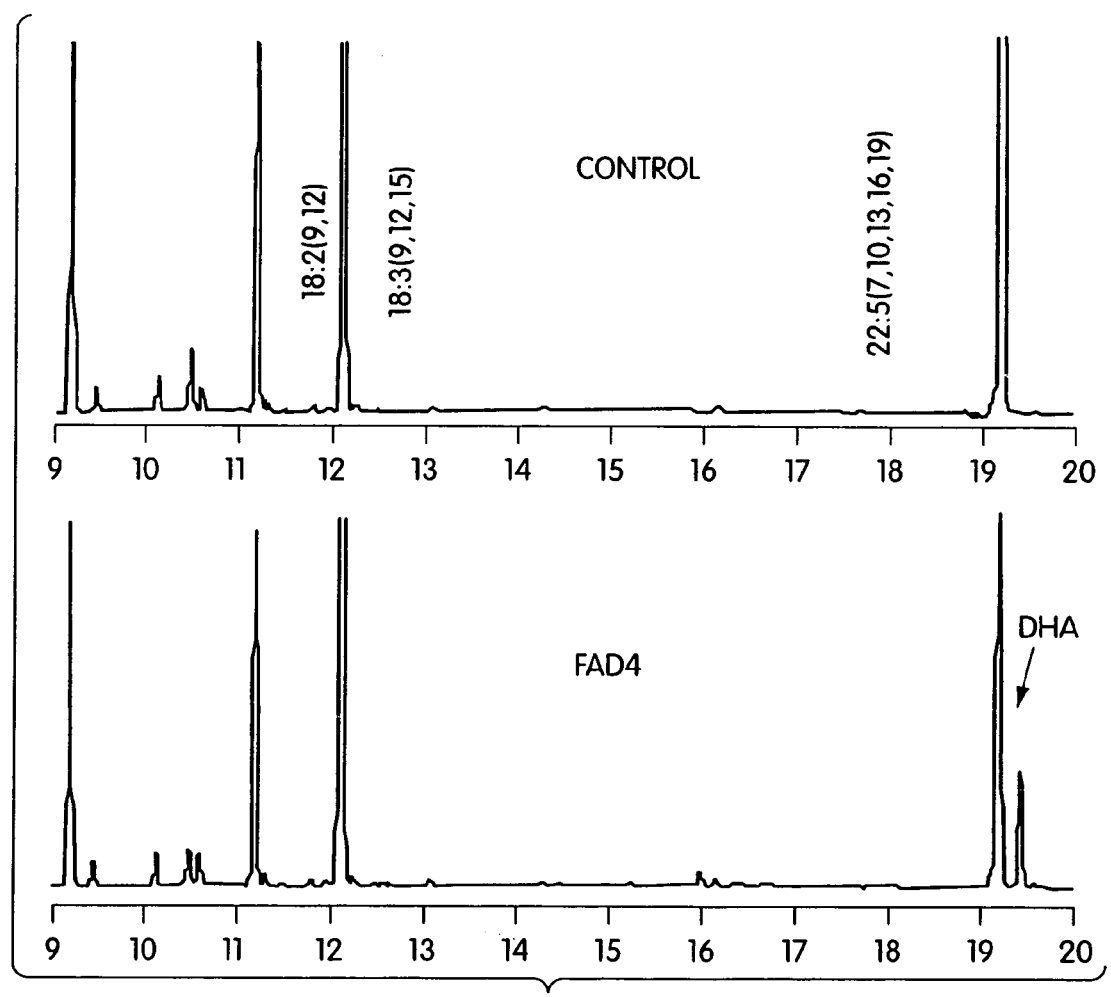
FIG. 16 is a GC analysis of FAMEs from leaves of *Brassica juncea* expressing Fad4 under the control of 35S promoter with exogenously supplied substrate 22:5 (n-3).

To determine whether *Traustochytrium* Fad4 is functional in oilseed crops, *B. juncea* were transformed with the construct containing Fad4 under the control of a constitutive promoter. Eight independent transgenic plants were obtained. In *B. juncea* there is no Δ4 fatty acid desaturase substrates available. Thus, to examine the activity of the transgenic enzyme in the plants, the 22:5 (n-3) substrate must be exogenously supplied. In this experiment, both wild type and transgenics were applied with an aqueous solution of sodium docosapentaeneate. It was found that exogenously applied substrates were readily taken up by roots, stem, and leaves of both types of plants, but converted into DHA only in transgenics. Leaves have a higher level of production of DHA than roots and stems. In leaves, the exogenous substrate was incorporated to a level of 10-20% of the total fatty acids and Δ4 desaturated fatty acid (22:6, n-3) was produced in a range of 3-6% of the total fatty acids (FIG. 16). These results indicate that the Δ4 fatty acid desaturase from *Traustochytrium* is functional in oilseed crops.

Example 10

Expression of FAD5-2 in *B. juncea*

Figure 17:
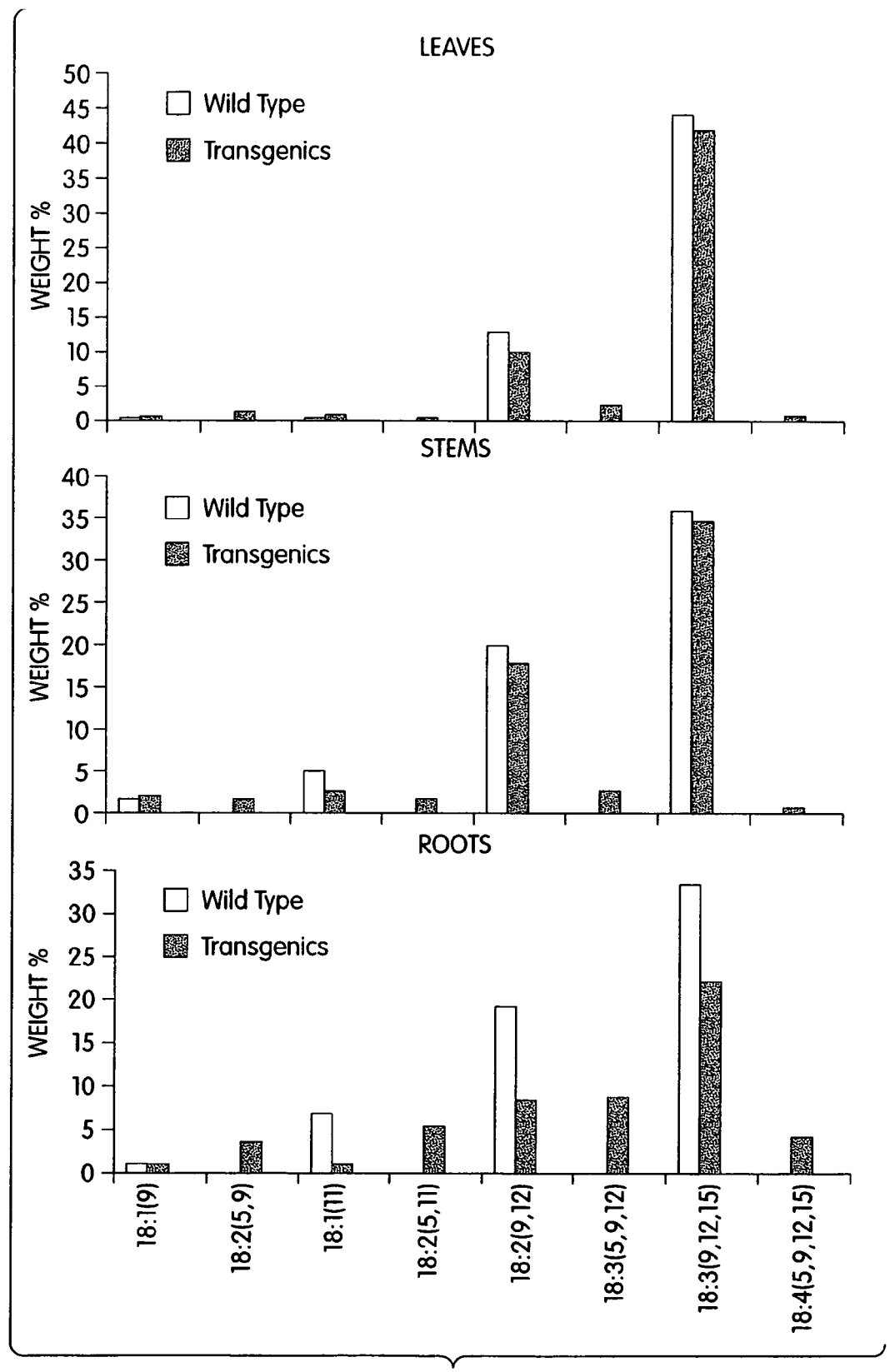
FIG. 17 shows the fatty acid composition of vegetative tissues (leaves, stems, and roots) of one transgenic T1 line with Fad5-2 under the control of the 35S promoter. The fatty acid levels are shown as the weight percentage of total fatty acids in *B. juncea*.

To determine whether Fad5-2 is functional in oilseed crops and its expression has any effect on their growth and development, *B. juncea* were transformed with a binary vector that contained Fad5-2 cDNA behind a constitutive promoter (a tandem cauliflower mosaic virus 35S promoter). Six independent primary transgenic plants were obtained and the fatty acid profile of lipids from different tissues was determined. FIG. 17 shows the fatty acid composition of three-week-old seedling plants from one $T_1$ line. Compared with wild type, all transgenic plant tissues have an altered fatty acid profile containing four additional peaks which were identified as four different Δ5-undesaturated polymethylene-interrupted fatty acids (Δ5-UPIFAs), specifically, taxoleic (18:2-5,9); ephedrenic (18:2-5,11); pinolenic (18:3-5,9,12), and coniferonic acids (18:4-5,9,12,15). Thus *B. juncea*, like yeast, can functionally express the *P. irregulare* Δ5 desaturase to convert the endogenous substrates 18:1-9; 18:1-11; 18:2-9,12, and 18:3-9,12,15 to the corresponding Δ5 desaturated fatty acids. The roots produced the highest amount of the Δ5-UPIFAs, representing more than 20% of the total fatty acids, followed by 6% in stems and 5% in leaves (FIG. 17).

Figure 18:
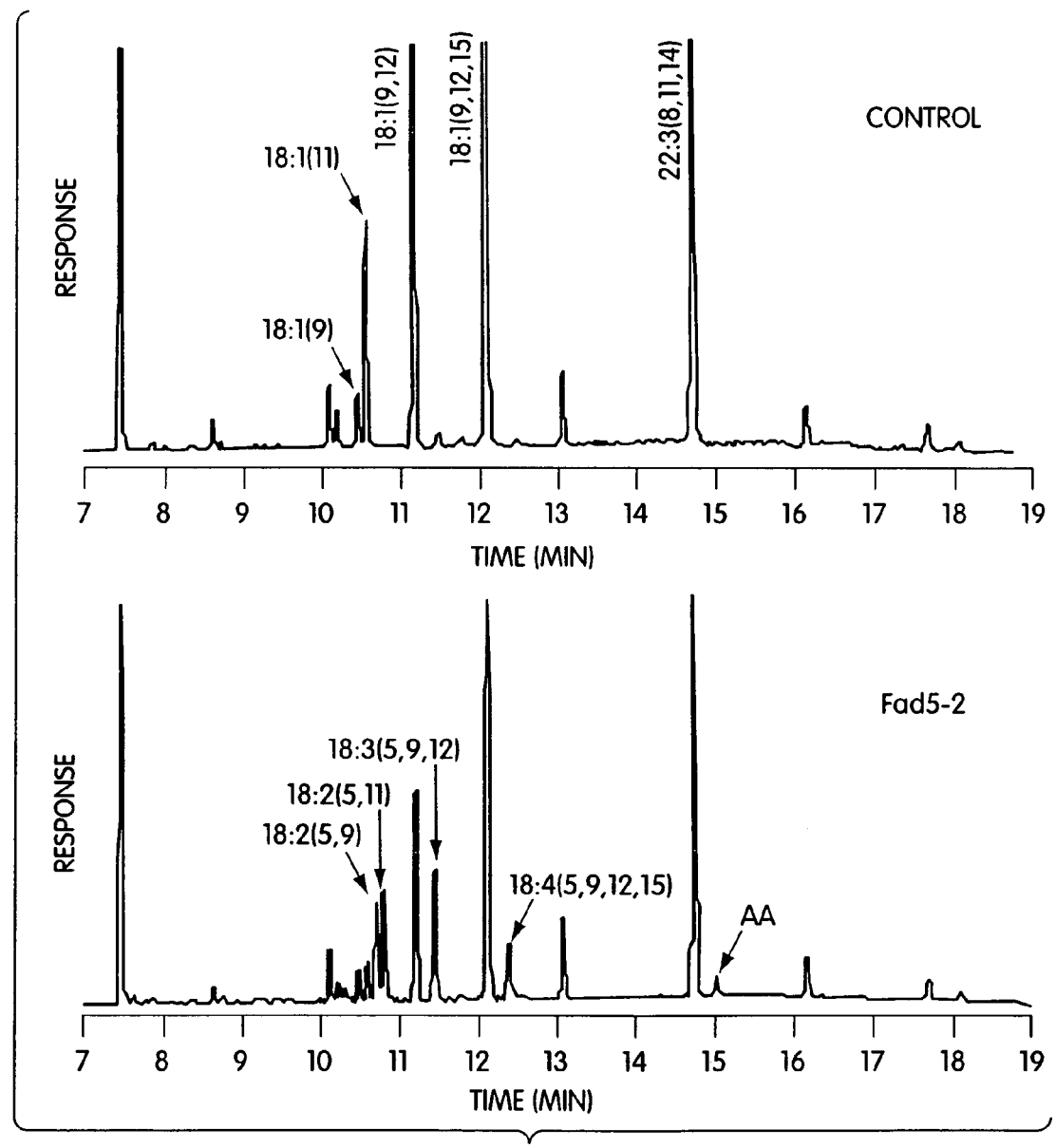
FIG. 18 is a GC analysis of root FAMEs of *B. juncea* expressing Fad5-2 with exogenous substrate homo-γ-linolenic acid (HGLA, 20:3-8,11,14).

In *B. juncea* there is no homo-gamma-linolenic acid (20:3-8,11,14) substrate available. Thus, to examine whether the transgenic plant can produce AA, the substrate 20:3(8,11,14) was exogenously supplied. In this experiment, both wild type and transgenics were applied with an aqueous solution of sodium homo-gamma-linolenate. It was found that exogenously applied substrates were readily taken up by roots, stem, and leaves of transgenic plants and converted into AA in plants (FIG. 18).

There was no observable phenotypic effect on the growth and development in the transgenic *B. juncea*, although the Δ5-UPIFAs accumulated in all parts of the plant. Growth and differentiation of vegetative tissues such as the leaves, stems, and roots were indistinguishable from the corresponding wild type.

Figure 19:
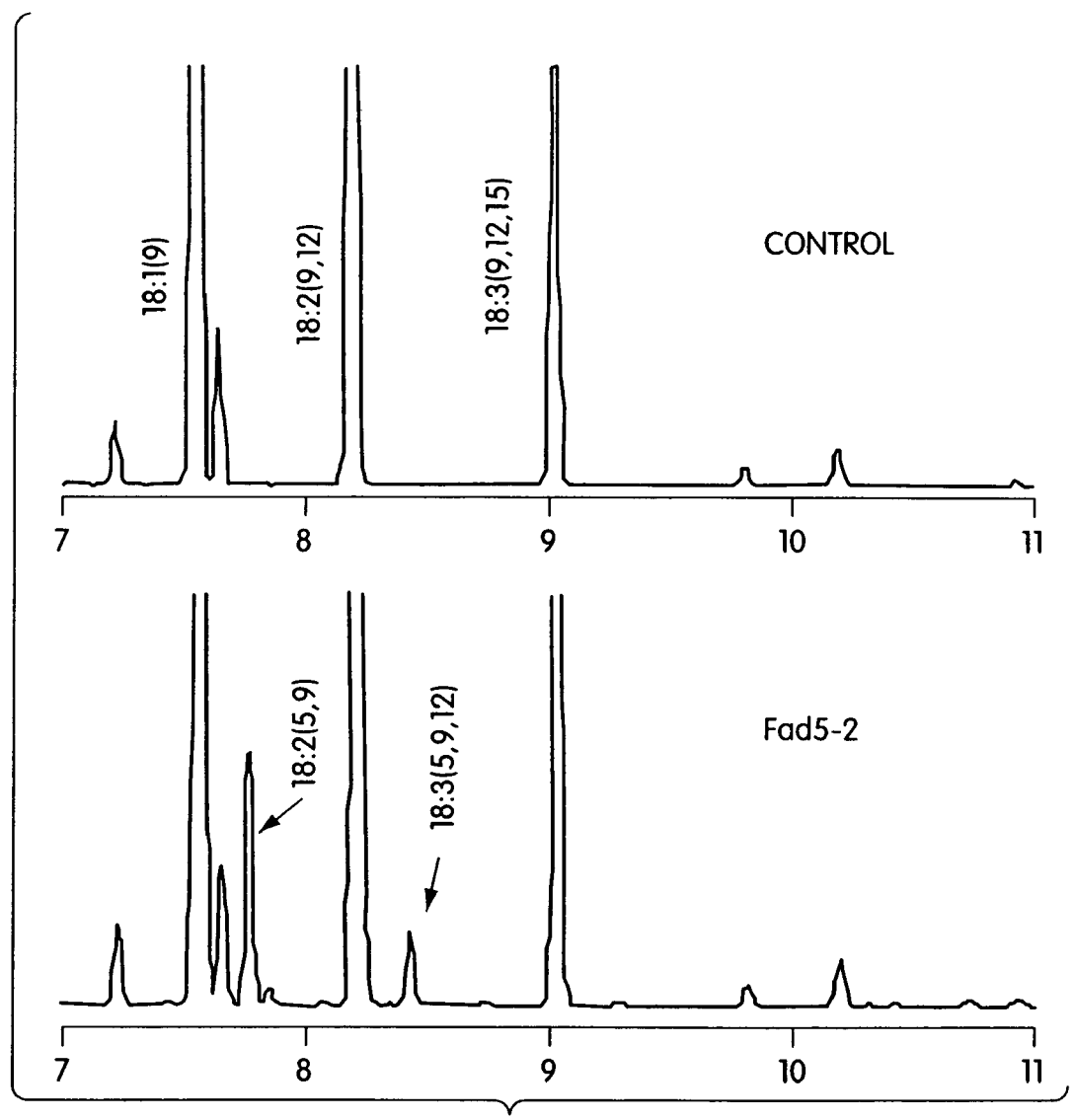
FIG. 19 is a GC analysis of FAMEs prepared from seeds of *B. juncea* expressing Fad5-2 under the control of the napin promoter.

To produce Δ5 desaturated fatty acids in seeds, *B. juncea* were transformed with the construct containing Fad5-2 cDNA behind a heterologous seed-specific promoter (*B. napus* napin promoter). Fatty acid analysis of transgenic seeds showed that there were two new fatty acids appearing in the gas chromatogram of transgenics compared with the wild type control (FIG. 19). They were identified as taxoleic acid (18:2-5,9) and pinolenic acids (18:3-5,9,12). Together, these fatty acids represent 9.4% of the seed fatty acids. Accumulation of Δ5-UPIFAs has no significant effect on the oleic acid content compared with the untransformed control.

Example 11

Expression of FAD5-2 in Flax

To produce Δ5 desaturated fatty acids in flax seeds, flax was transformed with Fad5-2 under the control of two seed-specific promoters, a heterologous *B. napus* napin promoter, and a flax endogenous promoter. As shown in FIG. 26, transgenic plants containing the napin promoter produced one Δ5 desaturated fatty acid, taxoleic acid in seeds at the level of less than 1% of the total fatty acids. Whereas transgenic plants containing the flax seed-specific promoter produced three Δ5 desaturated fatty acids: taxoleic, pinolenic, and coniferonic acid. Of these, taxoleic (18:2-5,9) was the most abundant and accounted for more than 9% of the total fatty acids in a elite line (FN-10-1), followed by coniferonic and pinolenic acids. Surprisingly, accumulation of Δ5 desaturated fatty acids in transgenic seeds has significant impact on the composition of other fatty acids, especially the oleic acid level. Accumulation of Δ5-UPIFAs was accompanied by a huge increase of the oleic acids in both types of transgenic plants expressing Fad5-2 desaturase under the control of the different promoters. The content of oleic acid in transgenic plants with the napin and flax seed-specific promoters, on the average, reached 44.7% and 24.3% of the total fatty acids, respectively, relative to the untransformed control at 17.4%.

Example 12

Expression of FAD6 in Flax

To produce Δ6 desaturated fatty acids in flax seeds, two types of flax were transformed with the construct that contains Fad6 cDNA under the control of a heterologous seed-specific promoter (*B. napus* napin promoter). Type I flax (Normandy) is a traditional industrial oilseed crop, whereas Type II (Solin) is an edible oilseed crop derived from chemical mutagenesis of Type I. A total of twelve transgenic plants were produced. The majority of transgenics exhibited two novel fatty acids whose retention times correspond to GLA and SDA and they constitute 0.1 to 4.3% of the total fatty acids (FIG. 27). The level of GLA in transgenic Solin type is higher than that of SDA, while GLA in transgenic Normandy is lower than SDA. This is understandable because linoleic acid is a major fatty acid in Solin type linseed while α-linolenic acid is a major fatty acid in Normandy seeds.

Example 13

Expression of FAD6 in *B. juncea*

Figure 20:
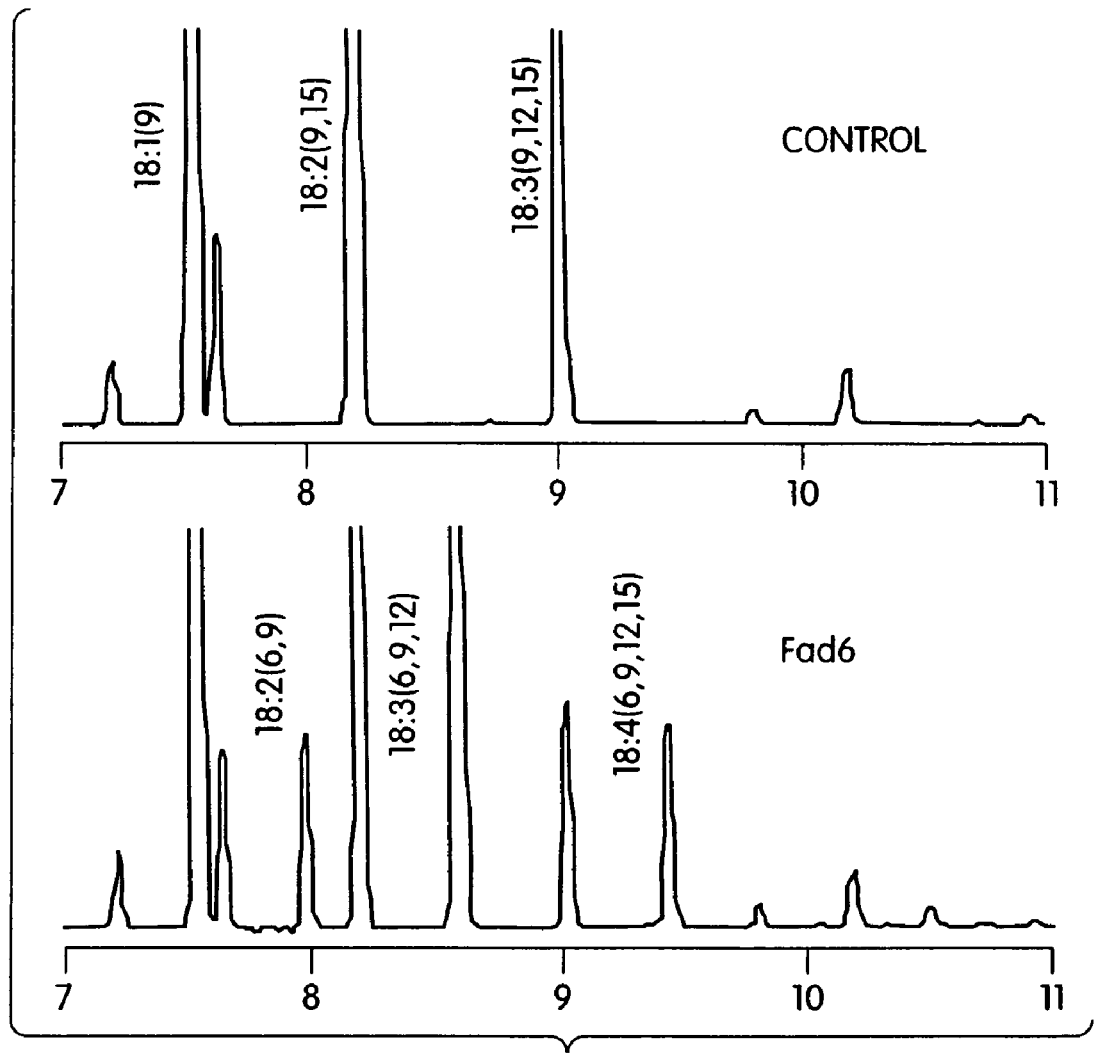
FIG. 20 is a GC analysis of seed FAMEs from *B. juncea* expressing Fad6. Three new peaks indicate three Δ6 desaturated fatty acids in transgenic seeds.
Figure 21:
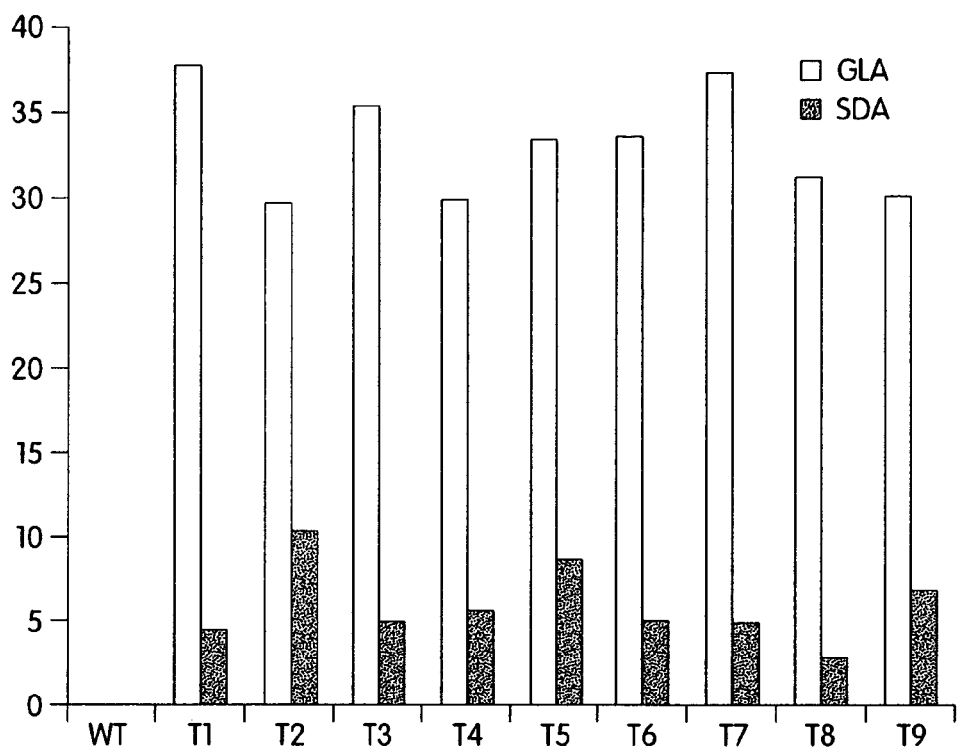
FIG. 21 shows the weight percentage of GLA (γ-linolenic acid) and SDA (stearidonic acid) accumulating in Fad6 transgenic seeds of *B. juncea*.

To produce Δ6 desaturated fatty acids in seeds of *B. juncea*, *B. juncea* were transformed with the same construct used in flax transformation, i.e., Fad6 under the control of the *B. napus* napin promoter. Fifteen independent transgenic plants were obtained. Fatty acid analysis of the transgenic seeds showed that there were three new fatty acids in the gas chromatogram of most transgenics compared with the wild type control (FIG. 20). The three fatty acids were identified as 18:2(6,9) and 18:3(6,9,12), and 18:4(6,9,12,15). *B. juncea*, like flax, can also functionally express Fad6 from *P. irregulare*, introducing a double bond at position 6 of endogenous substrate 18:1(9), 18:2(9,12), and 18:3(6,9,12) resulting in production of three corresponding Δ6 fatty acids in the transgenic seeds. Among the three new fatty acids produced in transgenic seeds, GLA is the most abundant one, with a level in transgenic seeds of 30% to 38% of the total fatty acids. The next most abundant component is SDA, which accounts for 3-10% of the total fatty acids in several transgenic lines (FIG. 21).

Figure 22:
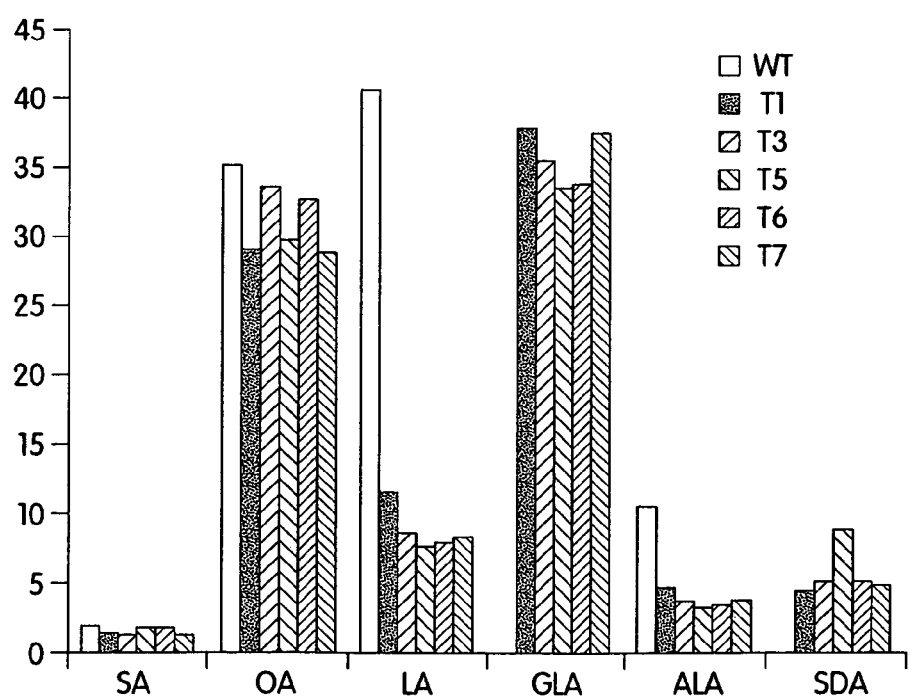
FIG. 22 shows the fatty acid compositions of the seed lipids from five transgenic lines expressing Fad6; SA=stearic acid; OA=oleic acid; LA=linoleic acid; GLA-γ-linolenic acid; ALA=α-linolenic acid; SDA=stearidonic acid.

The fatty acid compositions of transgenic seeds are shown in FIG. 22. It is clear that the high level production of Δ6 desaturated fatty acids is at the cost of two major fatty acids, linoleic and linolenic acids. Proportions of oleic and stearic acids in transgenics are slightly reduced, but not significantly compared to those in the wild type control. The content of linoleic acid in the transgenics was dramatically reduced. In the untransformed wild type, linoleic acid accounts for more than 40% of the total fatty acids in seeds. In transgenics, the level was reduced to less than 10%.

As compared to the reduction of linoleic acid in transgenics, the decrease in linolenic acid in transgenics is less dramatic, but still significant. In the untransformed wild type, linolenic acid accounts for more than 10% of the total fatty acids in seeds while in transgenics the level was reduced to less than 5%. The two dramatically reduced fatty acids in transgenic seeds are the substrates of the Δ6 desaturase, and the reduction is the cost for producing two corresponding Δ6 desaturated fatty acids.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. An isolated nucleic acid molecule selected from the group consisting of
    a) an isolated nucleic acid molecule comprising the nucleotide sequence set forth in SEQ ID NO: 7;
    b) an isolated nucleic acid molecule which encodes a polypeptide comprising the amino acid sequence set forth in SEQ ID NO: 8;
    c) an isolated nucleic acid molecule comprising a nucleotide sequence which is at least 95% identical to the nucleotide sequence set forth in SEQ ID NO: 7 and wherein the nucleic acid molecule encodes a Δ6 fatty acid desaturase molecule capable of converting linoleic acid (18:2) to gamma-linolenic acid;
    d) an isolated nucleic acid molecule comprising a nucleotide sequence which is at least 95% identical to the nucleotide sequence set forth in SEQ ID NO: 7 and wherein the nucleic acid molecule encodes a Δ6 fatty acid desaturase molecule capable of converting linolenic acid (18:3) to stearidonic acid;
    e) an isolated nucleic acid molecule which encodes a polypeptide comprising an amino acid sequence which is at least 95% identical to the amino acid sequence set forth in SEQ ID NO: 8 and wherein the polypeptide is a Δ6 fatty acid desaturase molecule capable of converting linoleic acid (18:2) to gamma-linolenic acid; and
    f) an isolated nucleic acid molecule which encodes a polypeptide comprising an amino acid sequence which is at least 95% identical to the amino acid sequence set forth in SEQ ID NO: 8 and wherein the polypeptide is a Δ6 fatty acid desaturase molecule capable of converting linolenic acid (18:3) to stearidonic acid.

2. The nucleic acid molecule of claim 1, wherein the desaturase molecule comprises at least one motif represented by the amino acid residues selected from the group consisting of residues 42-47, residues 178-183, residues 215-220, and residues 400-405 of SEQ ID NO: 8.

3. The nucleic acid molecule of claim 1 encoding a polypeptide comprising amino acid residues 42-47, 178-183, 215-220, and 400-405 of SEQ ID NO: 8.

4. A vector comprising the nucleic acid molecule of claim 1.

5. The vector of claim 4, wherein the vector is an expression vector.

6. A host cell comprising the expression vector of claim 5.

7. The host cell of claim 6, wherein the cell is selected from the group consisting of a plant cell, a microbial cell, and an animal cell.

8. The host cell of claim 7, wherein the plant cell is a cell obtained from an oilseed crop selected from the group consisting of flax (*Linum* sp.), *Brassica napus*, *Brassica juncea*, rapeseed (*Brassica* sp.), soybean (*Glycine* and *Soja* sp.), sunflower (*Helianthus* sp.), cotton (*Gossypium* sp.), corn (*Zea mays*), olive (*Olca* sp.), safflower (*Carthamus* sp.), cocoa (*Theobroma cacoa*), and peanut (*Arachis* sp.).

9. The host cell of claim 7, wherein the microbial cell is selected from the group consisting of *Thraustochytrium*, *Pythium irregulare*, *Schizochytrium*, and *Crythecodinium*.

10. A method of producing an unsaturated fatty acid comprising culturing or cultivating the cell of claim 6 under conditions such that the unsaturated fatty acid is produced.

11. The method of claim 10, wherein the unsaturated fatty acid is gamma-linolenic acid (GLA).

12. The method of claim 10, wherein the unsaturated fatty acid is stearidonic acid (SDA).

13. The method of claim 10, further comprising recovering the unsaturated fatty acid.

* * * * *